United States Patent
Chung et al.

(10) Patent No.: US 12,240,913 B2
(45) Date of Patent: *Mar. 4, 2025

(54) ANTI-HER2/ANTI-4-1BB BISPECIFIC ANTIBODY AND USE THEREOF

(71) Applicants: ABL Bio Inc., Seongnam-si (KR); YUHAN CORPORATION, Seoul (KR)

(72) Inventors: Hyejin Chung, Seongnam-si (KR); Yeryoung Yong, Seongnam-si (KR); Kyeongsu Park, Seongnam-si (KR); Eunyoung Park, Seongnam-si (KR); Ui-Jung Jung, Seongnam-si (KR); Yangsoon Lee, Seongnam-si (KR); Eunjung Kim, Seongnam-si (KR); Yong-Gyu Son, Seongnam-si (KR); Wonjun Son, Seongnam-si (KR); Seawon Ahn, Seongnam-si (KR); Donghoon Yeom, Seongnam-si (KR); Chanmoo Lee, Seongnam-si (KR); Junghyeon Hong, Gwacheon-si (KR); Moo Young Song, Seongnam-si (KR); Eun-Jung Lee, Yongin-si (KR); Na Rae Lee, Seoul (KR); Young Bong Park, Yongin-si (KR); Eun-Jung Lee, Yongin-si (KR); Taewang Kim, Yongin-si (KR)

(73) Assignees: ABL BIO INC., Seongnam-si (KR); YUHAN CORPORATION, Seoul (KR)

(*) Notice: Subject to any disclaimer, the term of this patent is extended or adjusted under 35 U.S.C. 154(b) by 0 days.

This patent is subject to a terminal disclaimer.

(21) Appl. No.: 16/939,536

(22) Filed: Jul. 27, 2020

(65) Prior Publication Data

US 2021/0024650 A1 Jan. 28, 2021

Related U.S. Application Data

(60) Provisional application No. 63/024,608, filed on May 14, 2020, provisional application No. 62/878,951, filed on Jul. 26, 2019.

(51) Int. Cl.
| | |
|---|---|
| *C07K 16/00* | (2006.01) |
| *A61P 35/00* | (2006.01) |
| *C07K 16/28* | (2006.01) |
| *C07K 16/32* | (2006.01) |
| *A61K 39/00* | (2006.01) |

(52) U.S. Cl.
CPC ............ *C07K 16/32* (2013.01); *A61P 35/00* (2018.01); *C07K 16/2878* (2013.01); *A61K 2039/505* (2013.01); *C07K 2317/21* (2013.01); *C07K 2317/31* (2013.01); *C07K 2317/51* (2013.01); *C07K 2317/515* (2013.01); *C07K 2317/56* (2013.01); *C07K 2317/565* (2013.01); *C07K 2317/622* (2013.01); *C07K 2317/92* (2013.01)

(58) Field of Classification Search
CPC ............... C07K 16/32; C07K 16/2878; C07K 2317/21; C07K 2317/31; C07K 2317/51; C07K 2317/515; C07K 2317/56; C07K 2317/565; C07K 2317/622; A61P 35/00; A61K 2039/505
See application file for complete search history.

(56) References Cited

U.S. PATENT DOCUMENTS

| 10,017,577 | B2 * | 7/2018 | Polakis | .................. C07K 16/28 |
|---|---|---|---|---|
| 2014/0178368 | A1 | 6/2014 | Sharp | |
| 2016/0152722 | A1 | 6/2016 | Sharp et al. | |
| 2018/0079824 | A1 | 3/2018 | Ahmed et al. | |
| 2019/0010248 | A1 | 1/2019 | Hinner et al. | |
| 2019/0169308 | A1 | 6/2019 | Dahlén et al. | |
| 2022/0242961 | A1 * | 8/2022 | Park | .................. C07K 16/2878 |

FOREIGN PATENT DOCUMENTS

| CN | 109310739 | 2/2019 |
|---|---|---|
| RU | 2664464 | 8/2018 |
| WO | 2016-149665 | 9/2016 |
| WO | 2017-173321 | 10/2017 |
| WO | 2018-085731 | 5/2018 |
| WO | 2018-156740 | 8/2018 |
| WO | 2019-016402 | 1/2019 |

OTHER PUBLICATIONS

Chester et al ( Blood, 131:49-57, 2018) (Year: 2018).*
NCT03330561 (clinical Trials.gov, Nov. 2017) (Year: 2017).*
KIPO, PCT Search Report & Written Opinion of PCT/KR2020/009871 dated Nov. 2, 2020.
Chen, Ching, et al. "Enhancement and destruction of antibody function by somatic mutation: unequal occurrence is controlled by V gene combinatorial associations." The EMBO journal 14.12 (1995): 2784-2794, Jun. 1995.
Diamond, Betty, et al., "Somatic mutation of the T15 heavy chain gives rise to an antibody with autoantibody specificity." Proceedings of the National Academy of Sciences 81.18 (1984): 5841-5844, Sep. 1984.

(Continued)

*Primary Examiner* — Lei Yao

(74) *Attorney, Agent, or Firm* — LEX IP MEISTER, PLLC

(57) ABSTRACT

Provided are an anti-4-1BB/anti-HER2 bispecific antibody, and a pharmaceutical composition and a method for treating and/or preventing a cancer using the same.

6 Claims, 19 Drawing Sheets

Specification includes a Sequence Listing.

(56) References Cited

OTHER PUBLICATIONS

On Solopova et al., "Bispecific Antibodies in Clinical Practice and Clinical Trials" (Literature Review). Clinical oncohematology. 2019;12(2):125-44, (2019).
Susumu Ohno et al., "Antigen-binding specificities of antibodies are primarily determined by seven residues of VH." Proceedings of the National Academy of Sciences 82.9 (1985): 2945-2949, May 1985.
Andrew A. Pakula et al., "Genetic analysis of protein stability and function." Annual review of genetics 23.1 (1989): 289-310, Dec. 1989.
A Royt et al., "Immunology", Mosby International Ltd., 1998, pp. 110-111.
Stuart Rudikoff et al., "Single amino acid substitution altering antigen-binding specificity." Proceedings of the National Academy of Sciences 79.6 (1982): 1979-1983, Mar. 1982.
Yarilin A.A., "Fundamentals of Immunology", Moscow, "Medicina", 1999, p. 172 English translation only the relevant part.
Rospatent, Office Action of the corresponding Russian Patent Application No. 2022101086., dated Jan. 24, 2024.
Rospatent, Office Action of RU 2022101086 dated Jun. 13, 2024.
Patrick W. B. Derksen et al., "Illegitimate WNT signaling promotes proliferation of multiple myeloma cells", PNAS, vol. 101, No. 16, 6122-6127, Apr. 20, 2004.
Peter B. Dirks, "Brain Tumor Stem Cells: Bringing Order to the Chaos of Brain Cancer", Journal of Clinical Oncology, vol. 26, No. 17, Jun. 10, 2008.
Miguel López-Lázaro, "The migration ability of stem cells can explain the existence of cancer of unknown primary site. Rethinking metastasis.", Oncoscience 2015, vol. 2, No. 5, May 1, 2015.
B. Tran et al., "Survival comparison between glioblastoma multiforme and other incurable cancers", Journal of Clinical Neuroscience, vol. 17, Issue 4, Apr. 2010, pp. 417-421.
Submitted A B et al: "History of Changes for Study: NCT03330561 Study Record Versions None (earliest Version on record) 2 Dec. 1, 2017 Contacts/Locations and Study Status 3 Feb. 13, 2018 Contacts/Locations and Study Status History of Changes for Study: NCT03330561 PRS-343 in HER2-Positive Solid Tumors Study NCT03", Recruitment Status, Study Status and Contacts/Locations Jan. 11, 2018, Apr. 23, 2019 (Apr. 23, 2019), pp. 1-6, XP093053393, Retrieved from the Internet: URL:https://clinicaltrials.gov/ct2/history /NCT0333056I?.
Chester Cariad et al: "Review Series Therapeutic Antibodies Immunotherapy targeting 4-IBB: mechanistic rationale, clinical results, and future strategies", Jan. 4, 2018 (Jan. 4, 2018), pp. 1-9, XP093053452, Retrieved from the Internet: URL:https://pubmed.ncbi.nim.nih.gov/29118009/ [retrieved on Jun. 12, 2023].
EPO, partial supplementary search report of EP 20848659.7 dated Jun. 21, 2023.

* cited by examiner

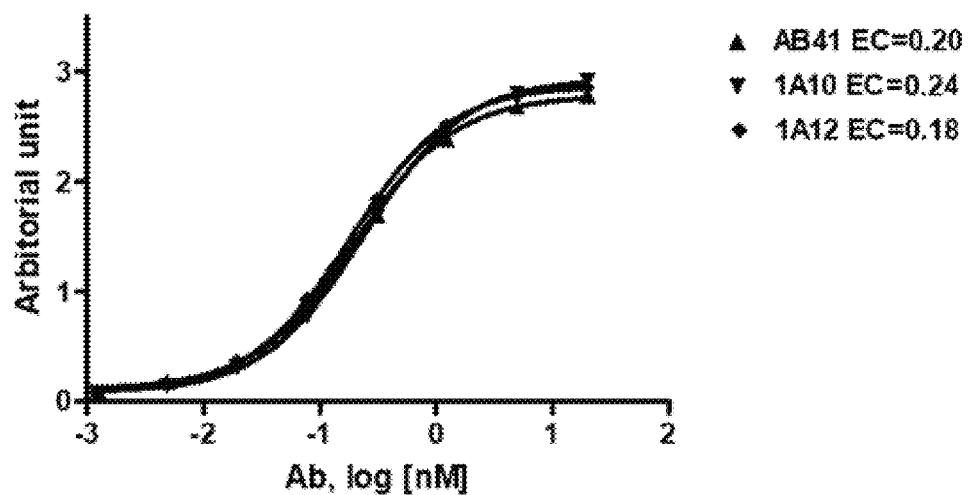
[FIG. 1a]
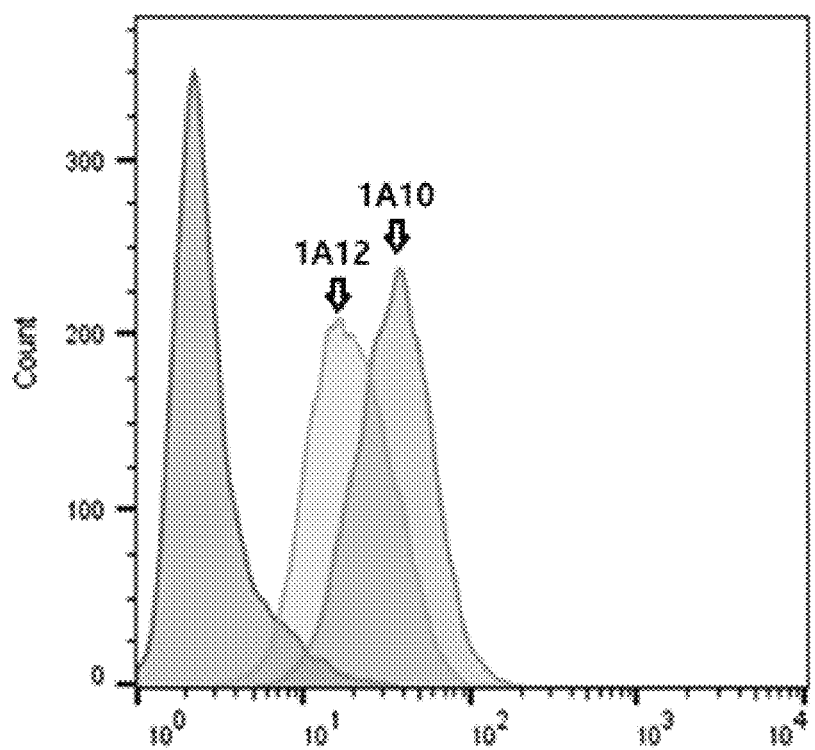
[FIG. 1b]

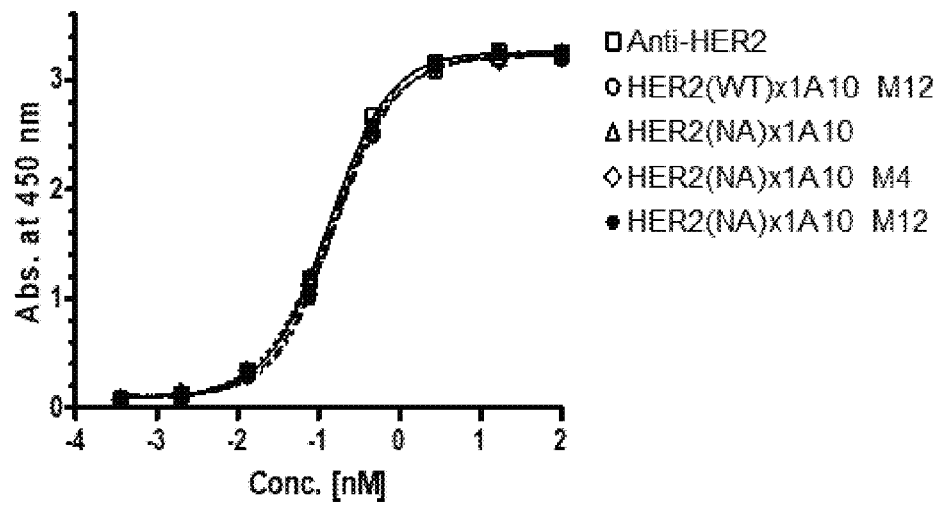
[FIG. 2a]
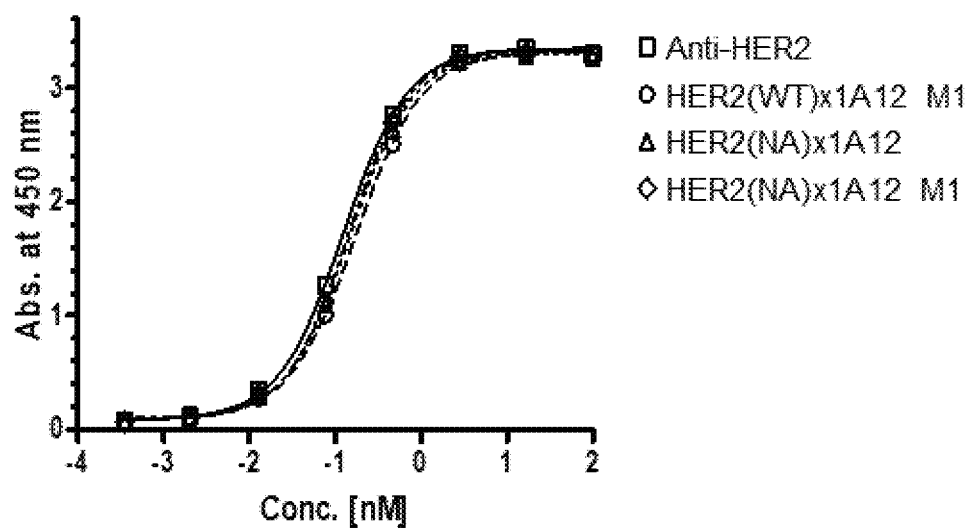
[FIG. 2b]

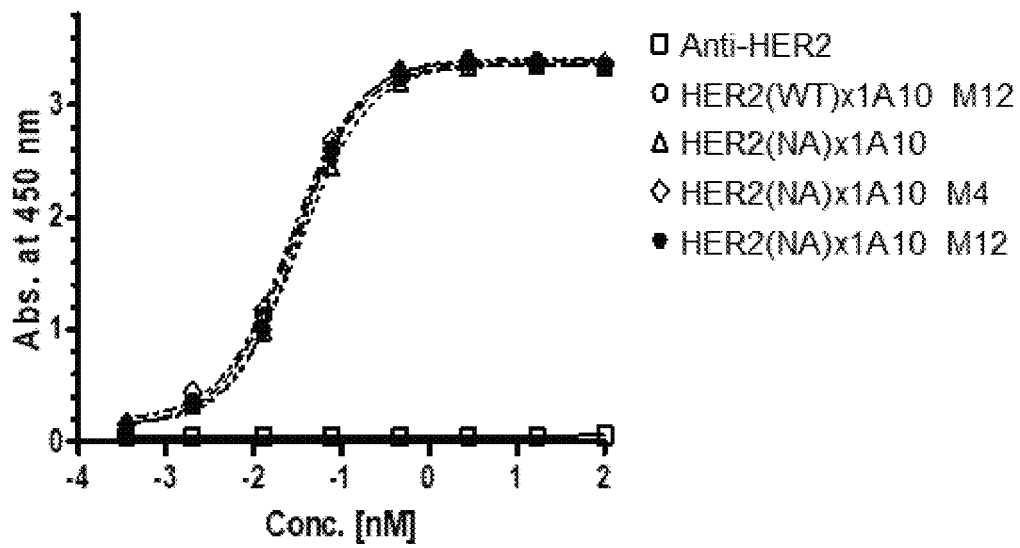
[FIG. 3a]
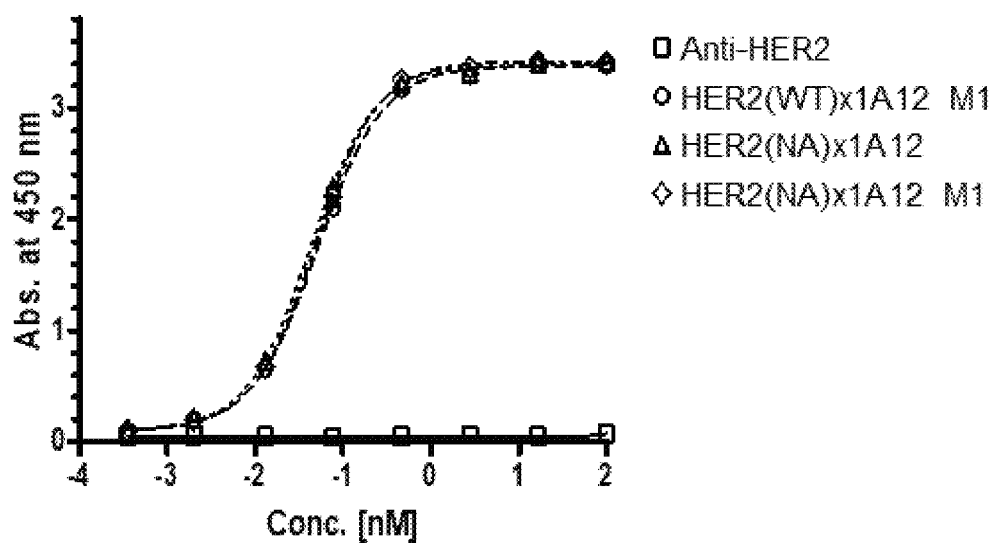
[FIG. 3b]

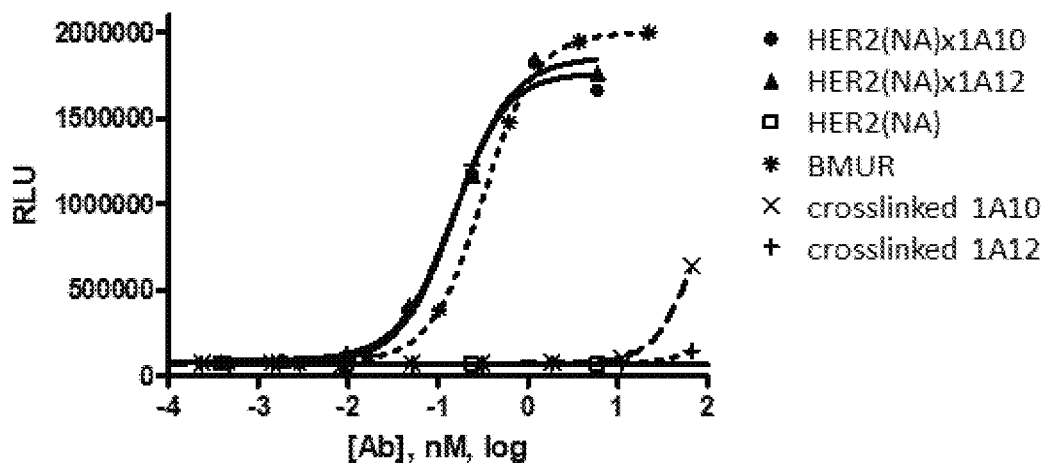
[FIG. 4a]
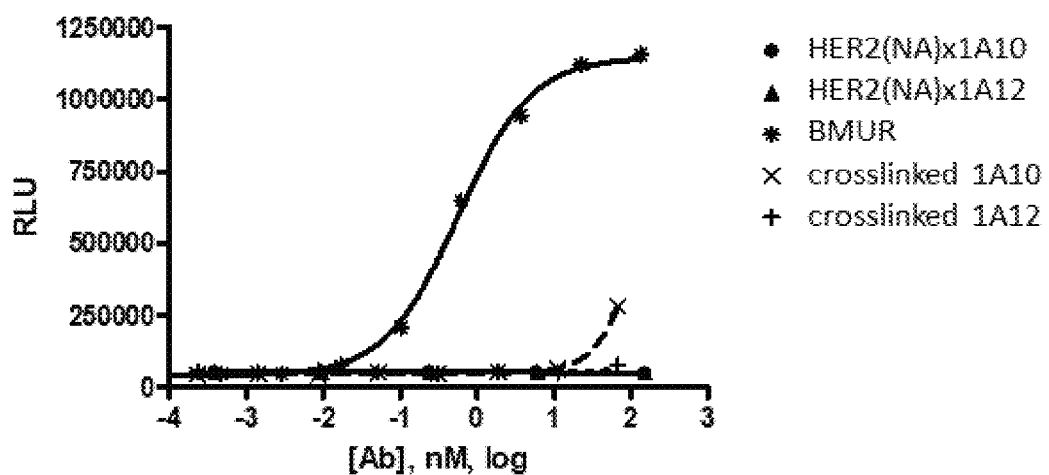
[FIG. 4b]

[FIG. 5a]
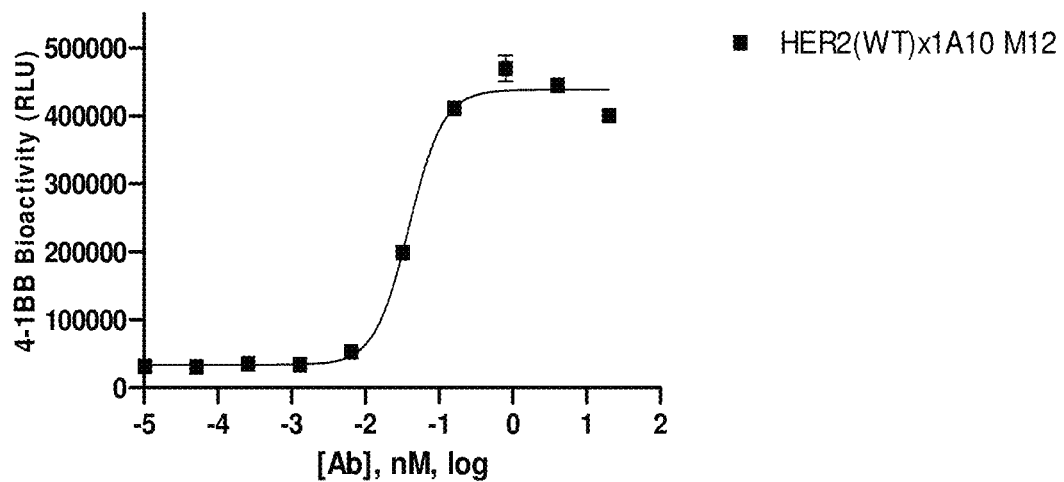
[FIG. 5b]
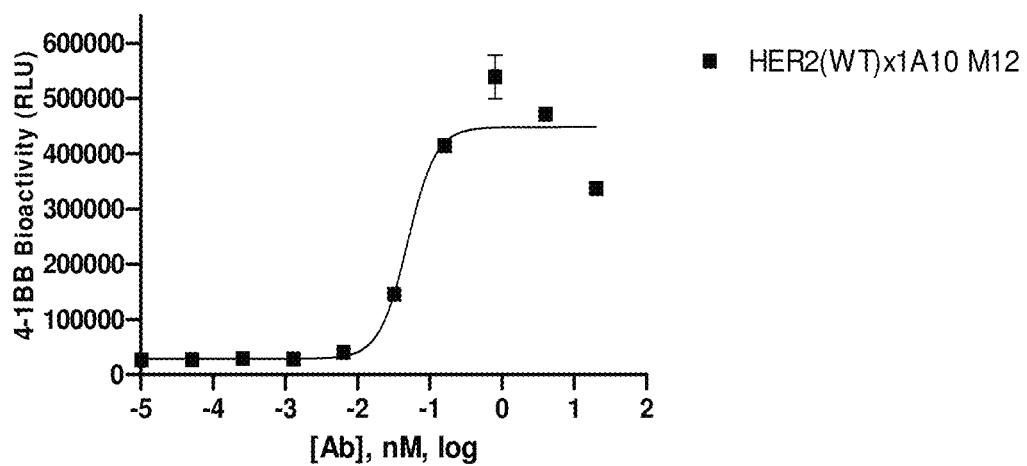

[FIG. 5c]
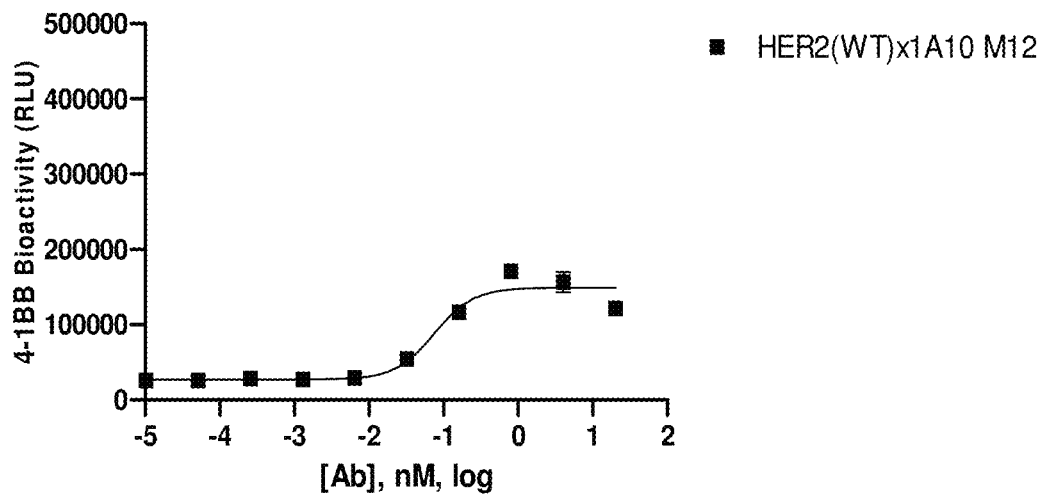
[FIG. 5d]
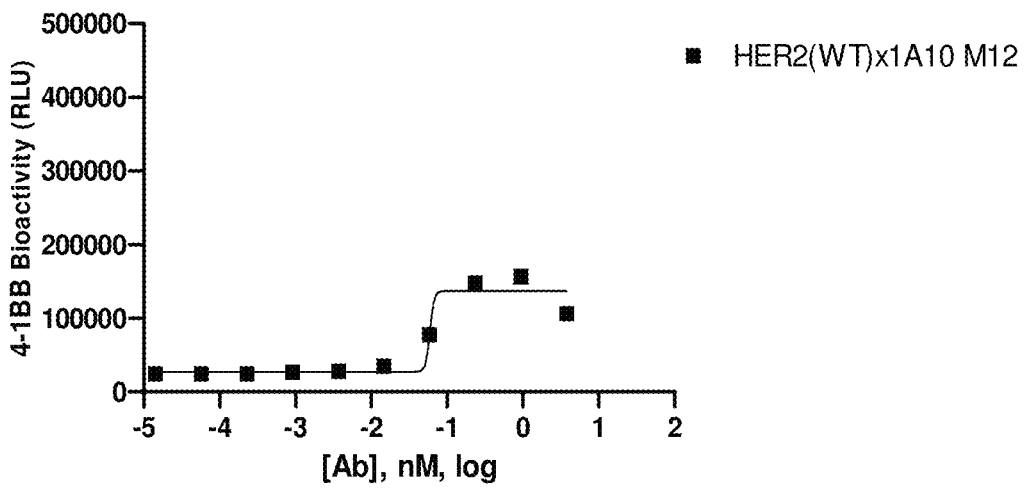

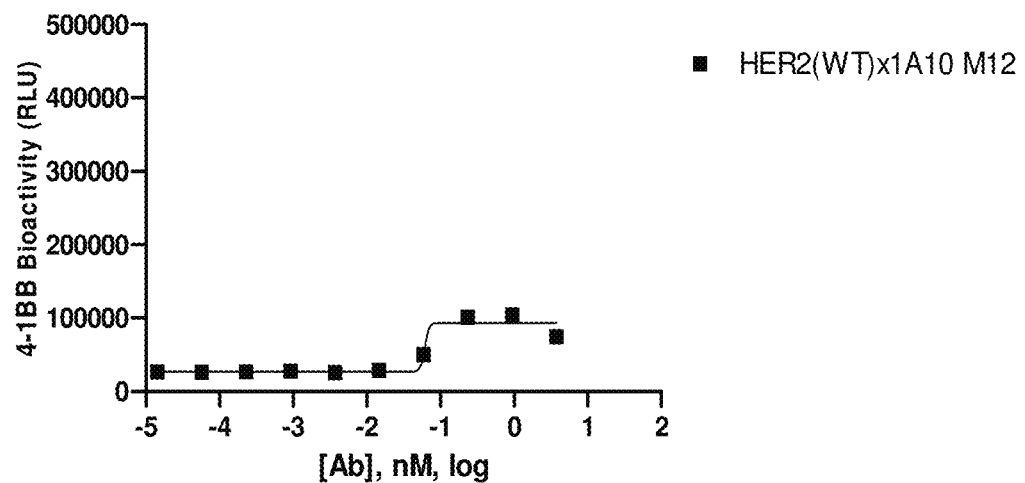
[FIG. 5e]
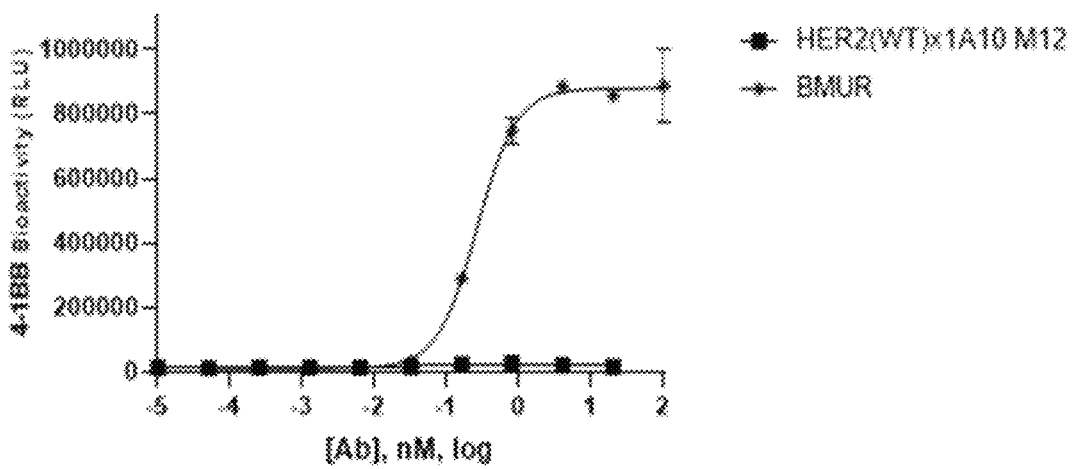
[FIG. 5f]

[FIG. 5g]
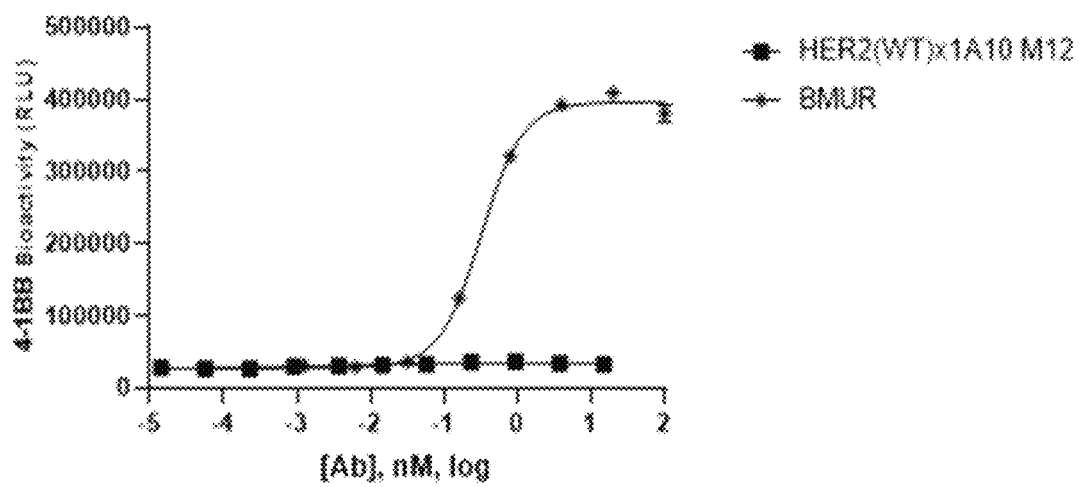
[FIG. 5h]
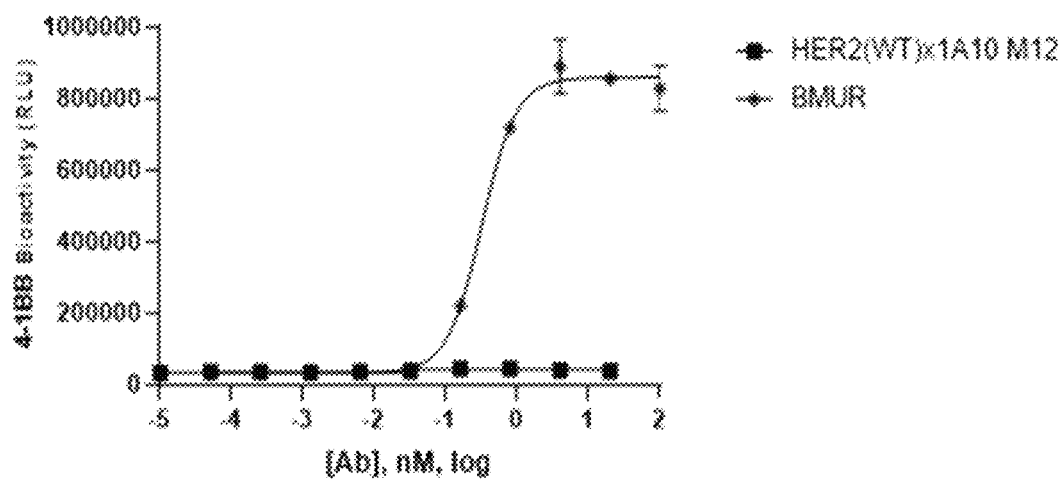

[FIG. 5i]
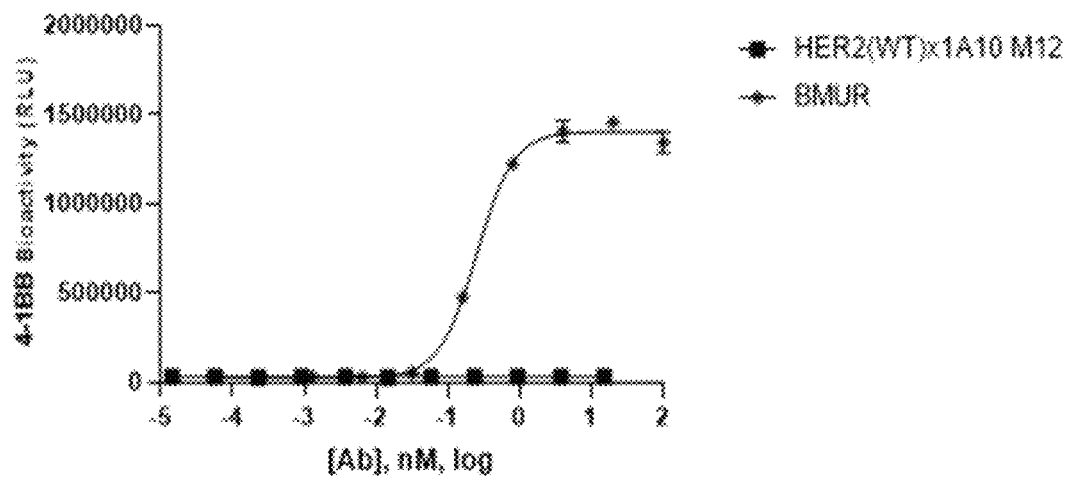
[FIG. 6a]
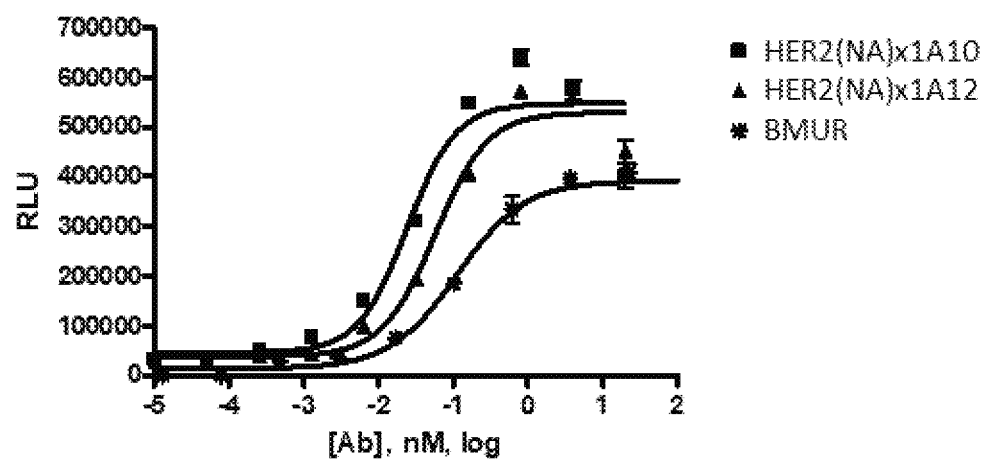

[FIG. 6b]
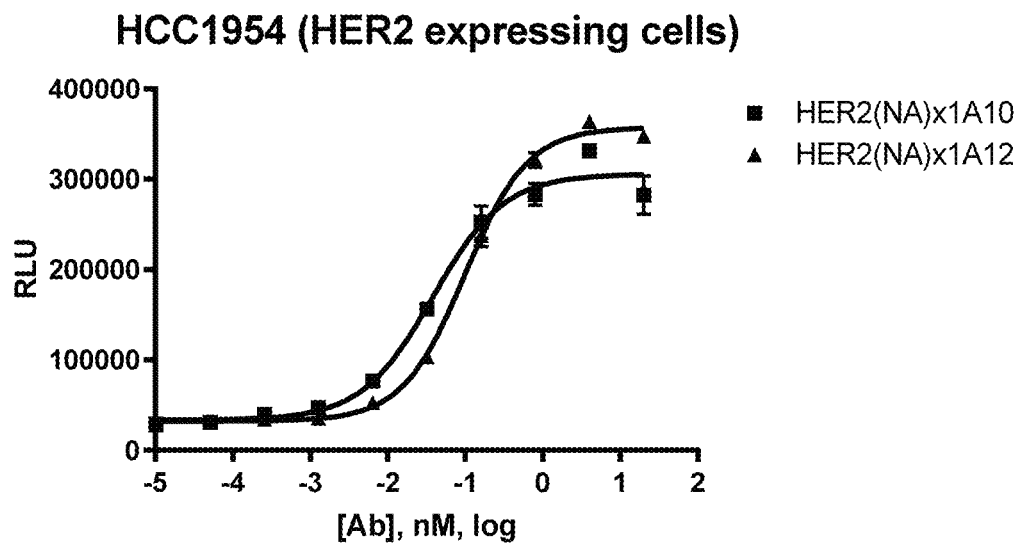
[FIG. 7]
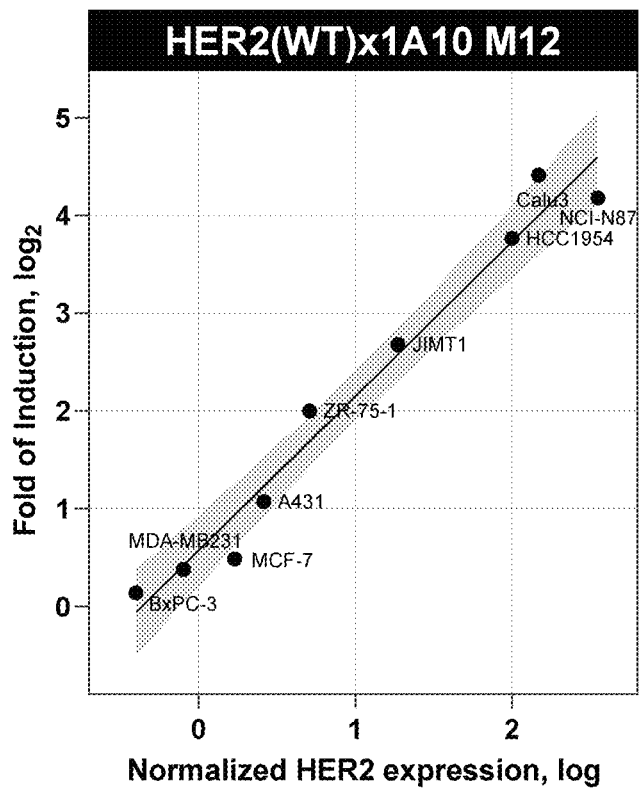

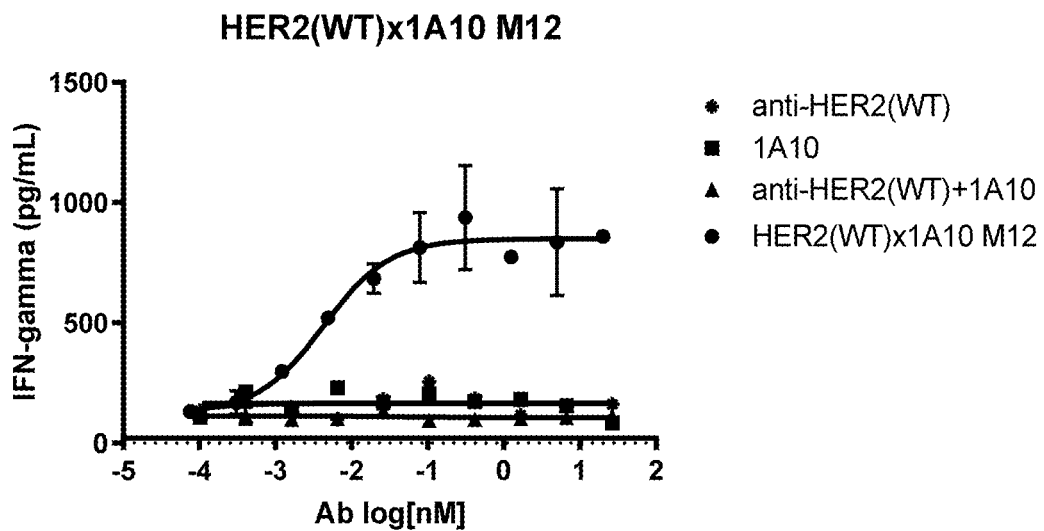
[FIG. 8a]
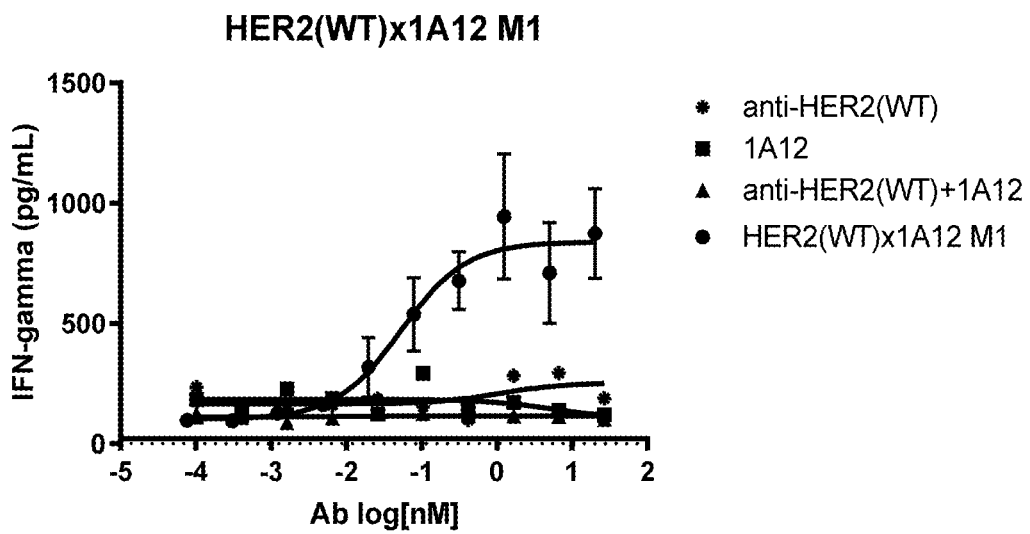
[FIG. 8b]

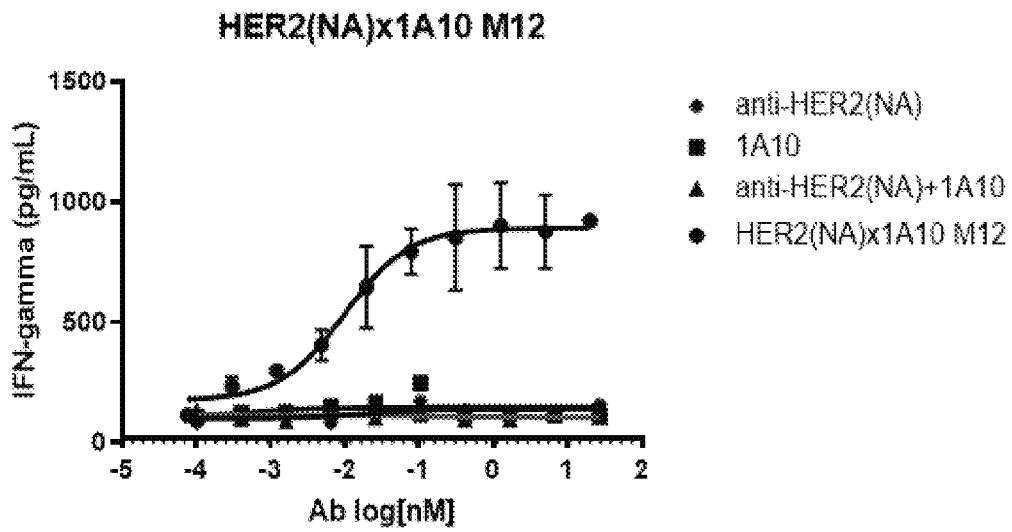
[FIG. 8c]
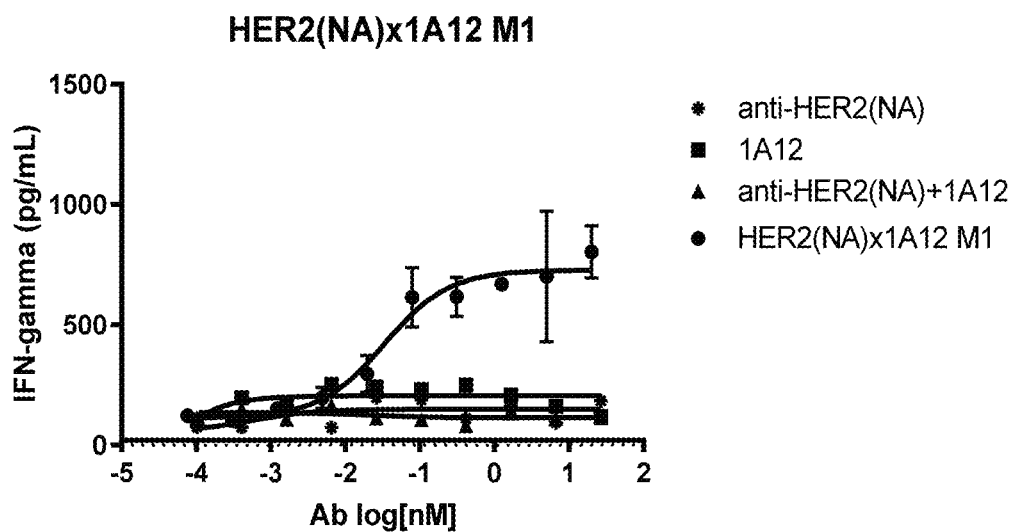
[FIG. 8d]

[FIG. 9a]
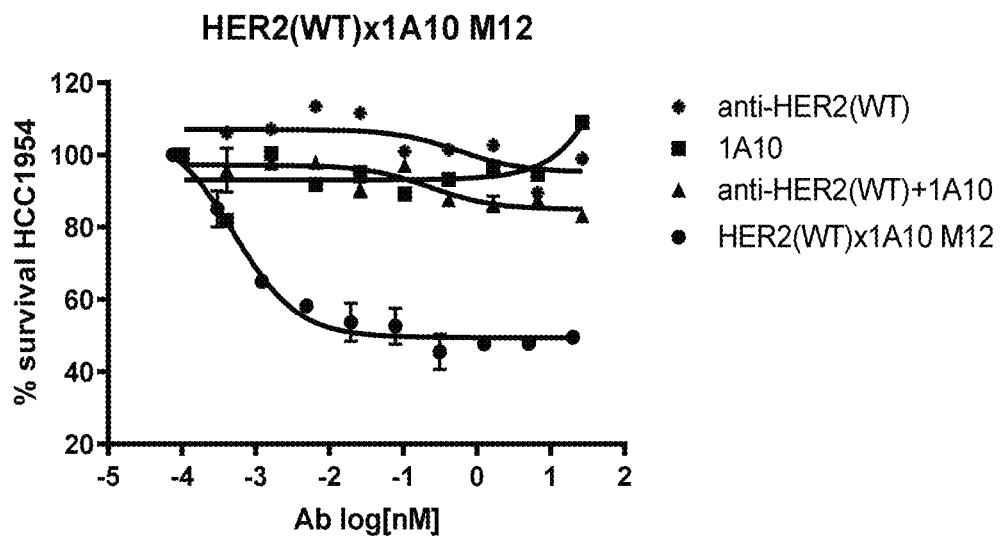
[FIG. 9b]
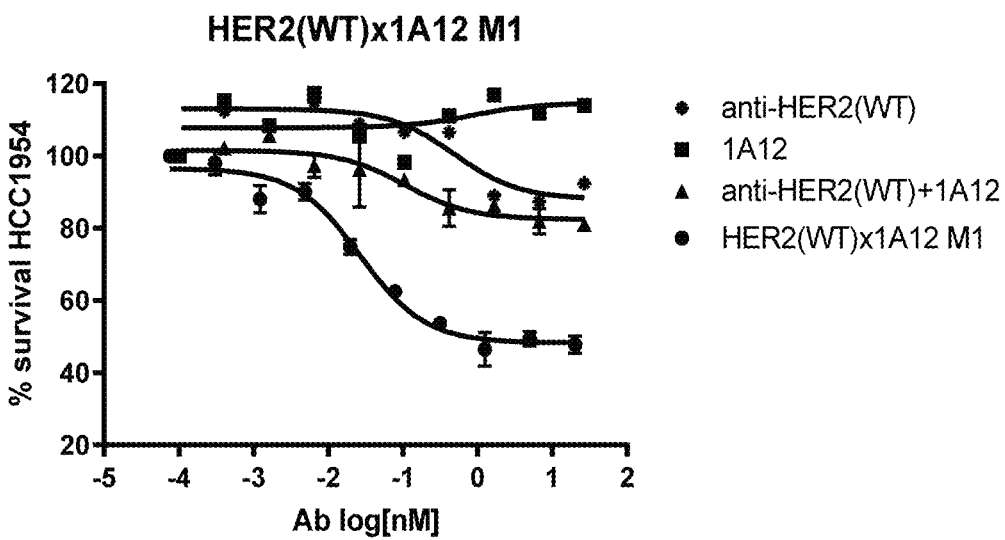

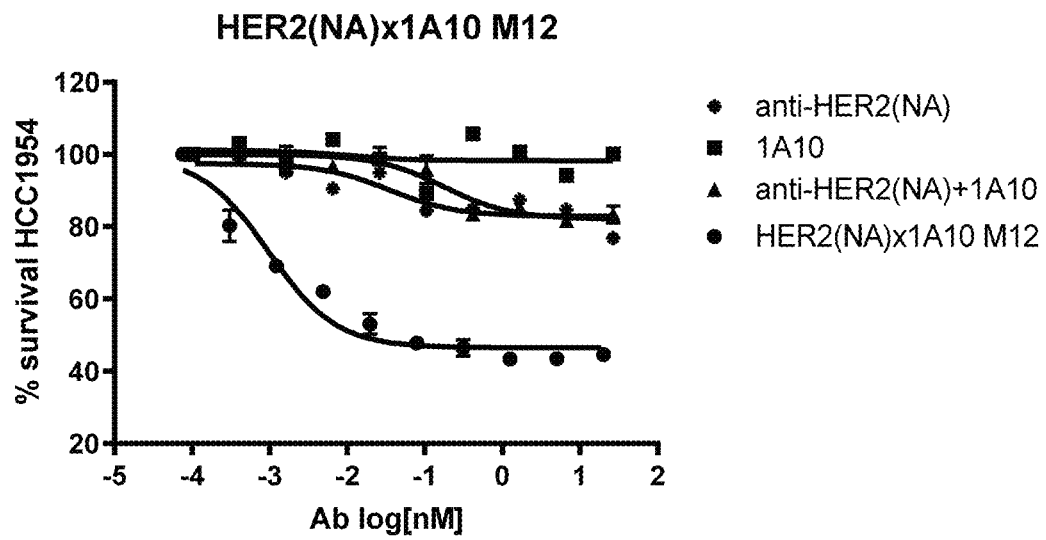
[FIG. 9c]
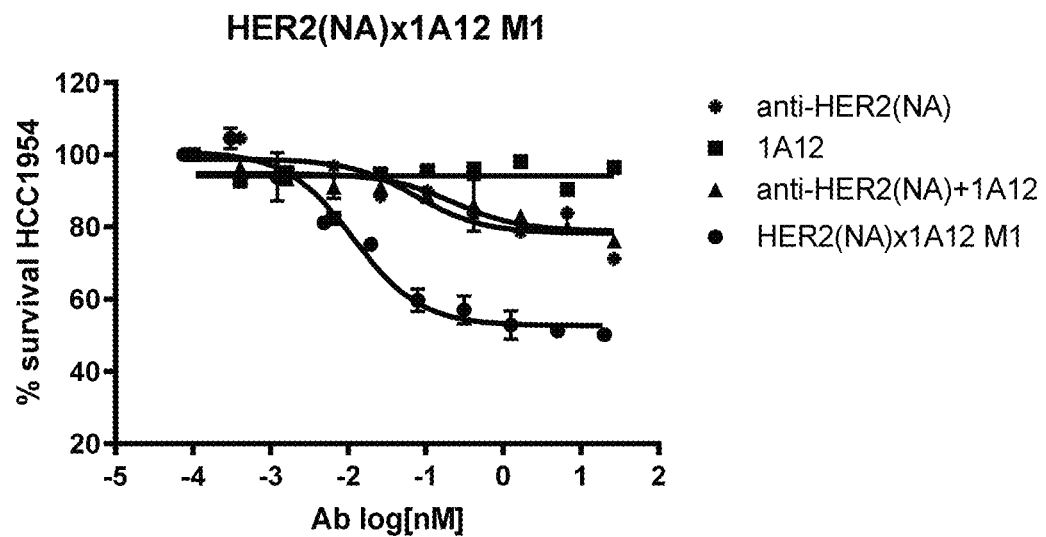
[FIG. 9d]

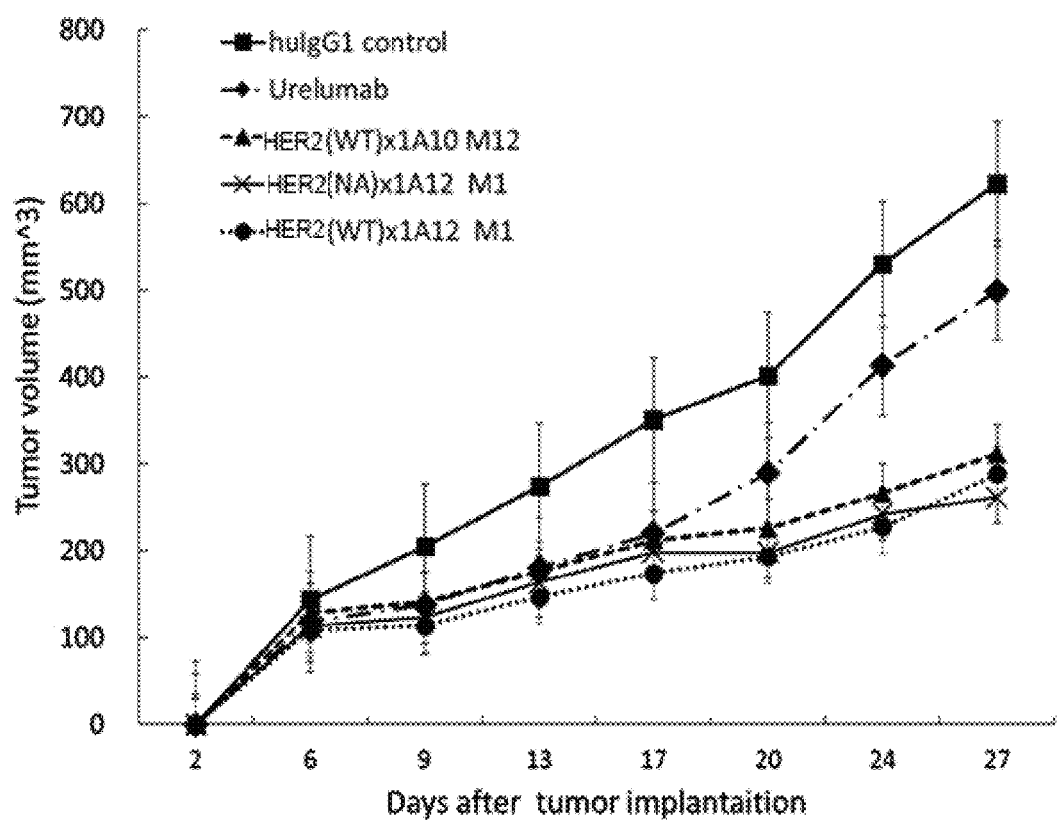
[FIG. 10]

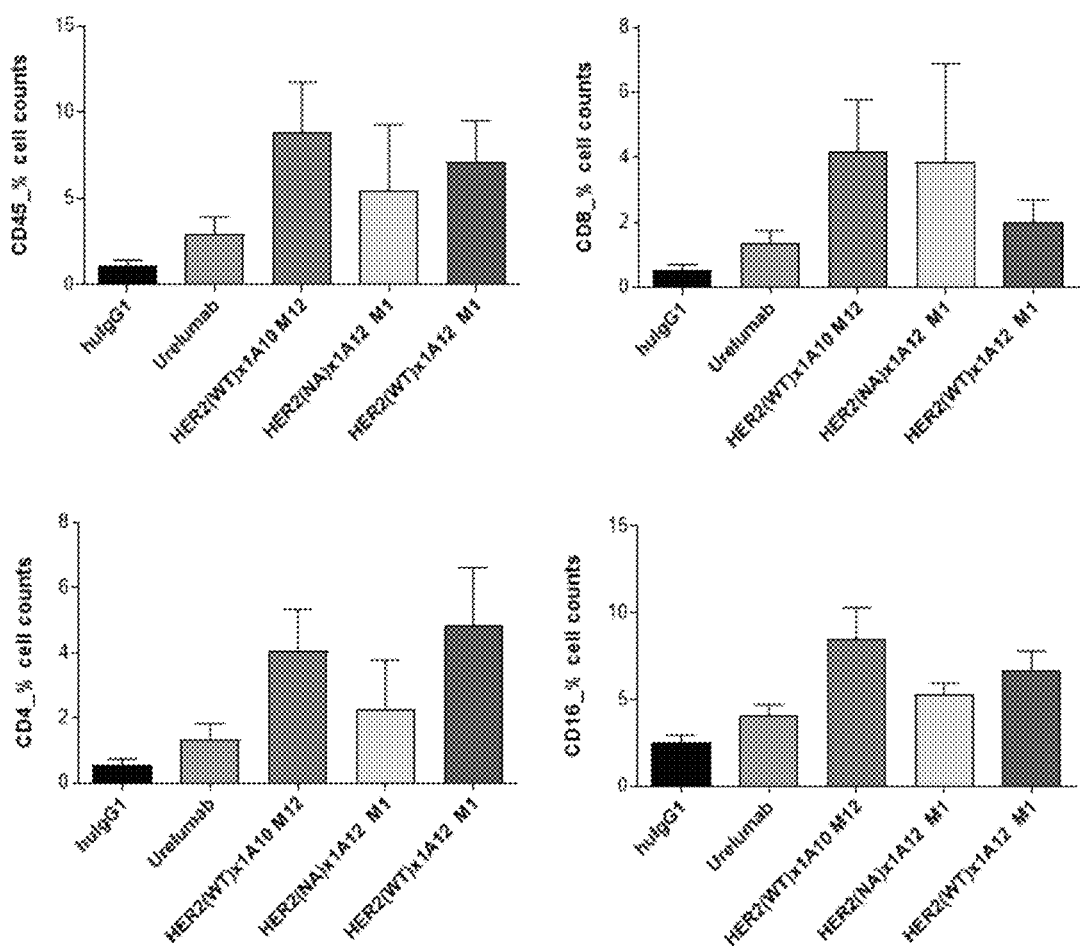
[FIG. 11]

[FIG. 12]
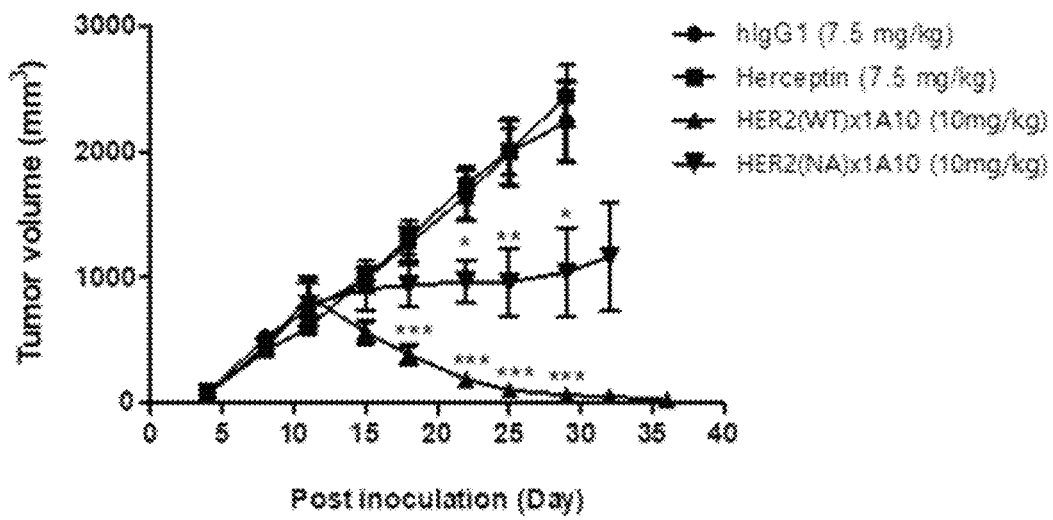
(Mean±SEM (n=5/group), *; p<0.01, ; p<0.01, *; p<0.001 vs hIgG1 control)
[FIG. 13]
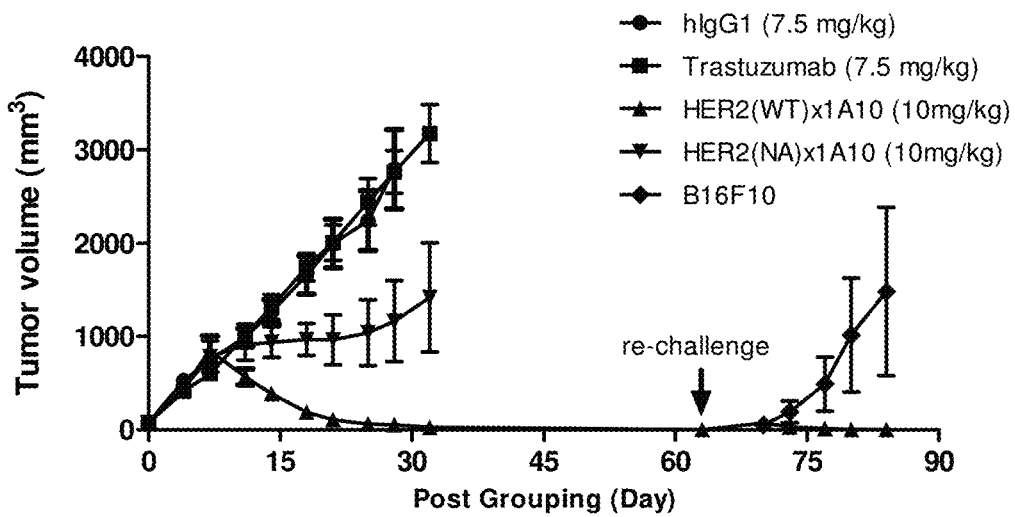

[FIG. 14]
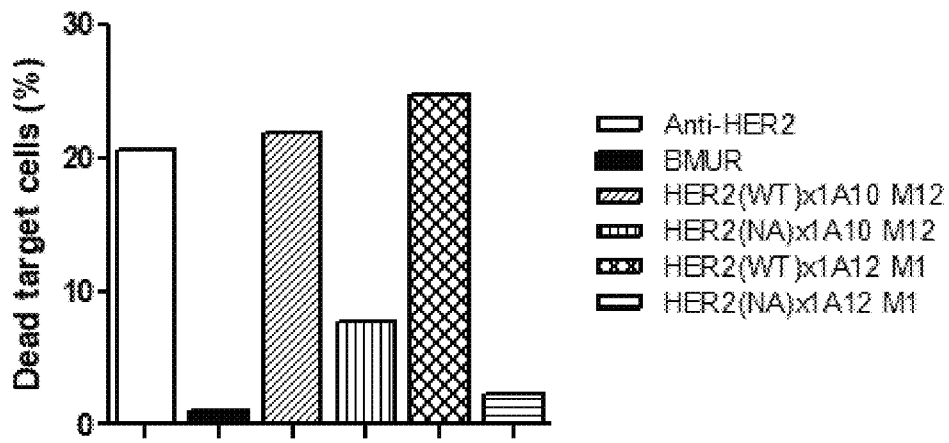
[FIG. 15a]
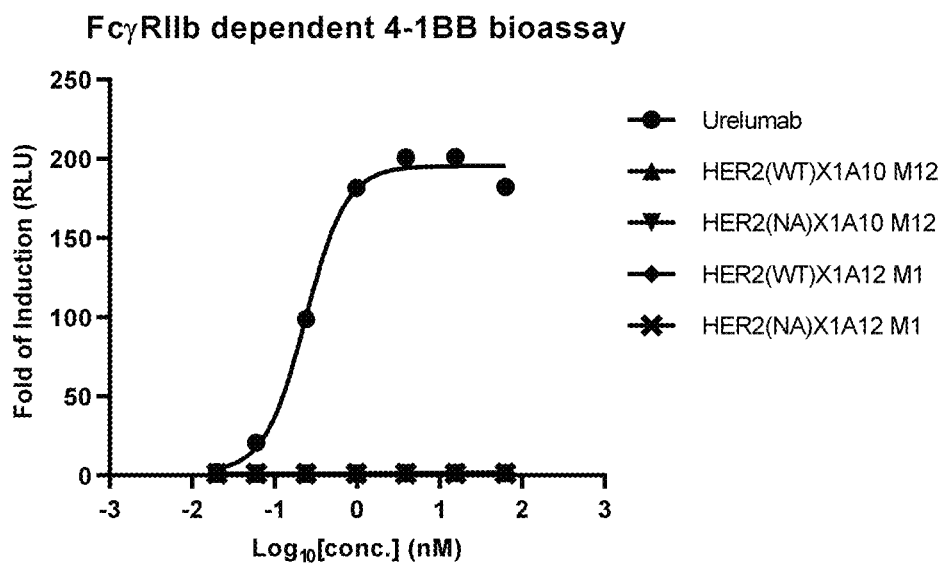

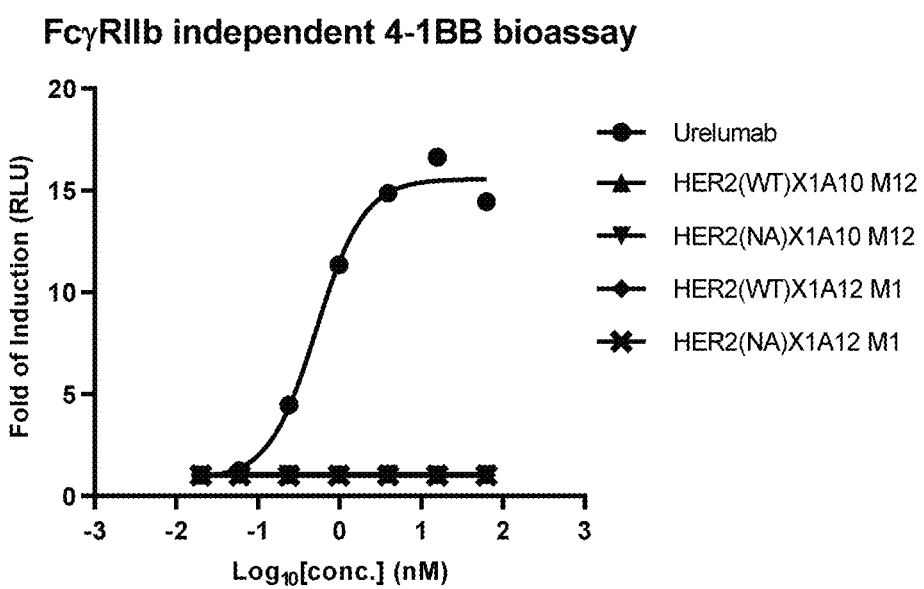
[FIG. 15b]

SEQUENCE LISTING

```
<160> NUMBER OF SEQ ID NOS: 89

<210> SEQ ID NO 1
<211> LENGTH: 5
<212> TYPE: PRT
<213> ORGANISM: Artificial Sequence
<220> FEATURE:
<223> OTHER INFORMATION: Synthetic_H-CDR1 of anti-4-1BB antibody

<400> SEQUENCE: 1

Ser Tyr Asp Met Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic_H-CDR1 of anti-4-1BB antibody

<400> SEQUENCE: 2

Gly Tyr Asp Met Ser
1               5

<210> SEQ ID NO 3
<211> LENGTH: 5
<212> TYPE: PRT
<213> ORGANISM: Artificial Sequence
<220> FEATURE:
<223> OTHER INFORMATION: Synthetic_H-CDR1 of anti-4-1BB antibody

<400> SEQUENCE: 3

Ser Tyr Trp Met His
1               5

<210> SEQ ID NO 4
<211> LENGTH: 17
<212> TYPE: PRT
<213> ORGANISM: Artificial Sequence
<220> FEATURE:
<223> OTHER INFORMATION: Synthetic_H-CDR2 of anti-4-1BB antibody

<400> SEQUENCE: 4

Trp Ile Ser Tyr Ser Gly Gly Ser Ile Tyr Tyr Ala Asp Ser Val Lys
1               5                   10                  15

Gly

<210> SEQ ID NO 5
<211> LENGTH: 17
<212> TYPE: PRT
<213> ORGANISM: Artificial Sequence
<220> FEATURE:
<223> OTHER INFORMATION: Synthetic_H-CDR2 of anti-4-1BB antibody
```

```
<400> SEQUENCE: 5

Val Ile Tyr Pro Asp Asp Gly Asn Thr Tyr Tyr Ala Asp Ser Val Lys
1               5                   10                  15

Gly

<210> SEQ ID NO 6
<211> LENGTH: 17
<212> TYPE: PRT
<213> ORGANISM: Artificial Sequence
<220> FEATURE:
<223> OTHER INFORMATION: Synthetic_H-CDR2 of anti-4-1BB antibody

<400> SEQUENCE: 6

Glu Ile Asn Pro Gly Asn Gly His Thr Asn Tyr Asn Glu Lys Phe Lys
1               5                   10                  15

Ser

<210> SEQ ID NO 7
<211> LENGTH: 12
<212> TYPE: PRT
<213> ORGANISM: Artificial Sequence
<220> FEATURE:
<223> OTHER INFORMATION: Synthetic_H-CDR3 of anti-4-1BB antibody

<400> SEQUENCE: 7

Asp Gly Gln Arg Asn Ser Met Arg Glu Phe Asp Tyr
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthetic_H-CDR3 of anti-4-1BB antibody

<400> SEQUENCE: 8

Asp Ala Gln Arg Asn Ser Met Arg Glu Phe Asp Tyr
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic_H-CDR3 of anti-4-1BB antibody

<400> SEQUENCE: 9

Asp Ala Gln Arg Gln Ser Met Arg Glu Phe Asp Tyr
1               5                   10

<210> SEQ ID NO 10
<211> LENGTH: 18
<212> TYPE: PRT
<213> ORGANISM: Artificial Sequence
<220> FEATURE:
<223> OTHER INFORMATION: Synthetic_H-CDR3 of anti-4-1BB antibody

<400> SEQUENCE: 10

His Gly Gly Gln Lys Pro Thr Thr Lys Ser Ser Ser Ala Tyr Gly Met
1               5                   10                  15

Asp Gly

<210> SEQ ID NO 11
```

```
<211> LENGTH: 10
<212> TYPE: PRT
<213> ORGANISM: Artificial Sequence
<220> FEATURE:
<223> OTHER INFORMATION: Synthetic_H-CDR3 of anti-4-1BB antibody

<400> SEQUENCE: 11

Ser Phe Thr Thr Ala Arg Ala Phe Ala Tyr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Synthetic_L-CDR1 of anti-4-1BB antibody

<400> SEQUENCE: 12

Ser Gly Ser Ser Ser Asn Ile Gly Asn Asn Tyr Val Thr
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Synthetic_L-CDR1 of anti-4-1BB antibody

<400> SEQUENCE: 13

Arg Ala Ser Gln Thr Ile Ser Asp Tyr Leu His
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic_L-CDR2 of anti-4-1BB antibody

<400> SEQUENCE: 14

Ala Asp Ser His Arg Pro Ser
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic_L-CDR2 of anti-4-1BB antibody

<400> SEQUENCE: 15

Tyr Ala Ser Gln Ser Ile Ser
1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic_L-CDR3 of anti-4-1BB antibody

<400> SEQUENCE: 16

Ala Thr Trp Asp Tyr Ser Leu Ser Gly Tyr Val
1               5                   10

<210> SEQ ID NO 17
<211> LENGTH: 9
```

```
<212> TYPE: PRT
<213> ORGANISM: Artificial Sequence
<220> FEATURE:
<223> OTHER INFORMATION: Synthetic_L-CDR3 of anti-4-1BB antibody

<400> SEQUENCE: 17

Gln Asp Gly His Ser Phe Pro Pro Thr
1               5

<210> SEQ ID NO 18
<211> LENGTH: 121
<212> TYPE: PRT
<213> ORGANISM: Artificial Sequence
<220> FEATURE:
<223> OTHER INFORMATION: Synthetic_heavy chain variable region of
      anti-4-1BB antibody (1A10)

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser
        115                 120

<210> SEQ ID NO 19
<211> LENGTH: 121
<212> TYPE: PRT
<213> ORGANISM: Artificial Sequence
<220> FEATURE:
<223> OTHER INFORMATION: Synthetic_heavy chain variable region of
      anti-4-1BB antibody (1A10 M4, 1A10 M12)

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser
        115                 120
```

<210> SEQ ID NO 20
<211> LENGTH: 121
<212> TYPE: PRT
<213> ORGANISM: Artificial Sequence
<220> FEATURE:
<223> OTHER INFORMATION: Synthetic_heavy chain variable region of
      anti-4-1BB antibody (1A10 M11, 1A10 M13)

<400> SEQUENCE: 20

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ser
        115                 120

<210> SEQ ID NO 21
<211> LENGTH: 127
<212> TYPE: PRT
<213> ORGANISM: Artificial Sequence
<220> FEATURE:
<223> OTHER INFORMATION: Synthetic_heavy chain variable region of
      anti-4-1BB antibody (1A12)

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 22
<211> LENGTH: 127
<212> TYPE: PRT
<213> ORGANISM: Artificial Sequence
<220> FEATURE:
<223> OTHER INFORMATION: Synthetic_heavy chain variable region of
      anti-4-1BB antibody (1A12M1)

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125

<210> SEQ ID NO 23
<211> LENGTH: 119
<212> TYPE: PRT
<213> ORGANISM: Artificial Sequence
<220> FEATURE:
<223> OTHER INFORMATION: Synthetic_heavy chain variable region of
    anti-4-1BB antibody (AB41)

<400> SEQUENCE: 23

Gln Val Gln Leu Gln Gln Ser Gly Ala Glu Val Ile Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Gly Asn Gly His Thr Asn Tyr Asn Glu Lys Phe
    50                  55                  60

Lys Ser Arg Ala Thr Leu Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Thr Thr Ala Arg Ala Phe Ala Tyr Trp Gly Gln Gly
            100                 105                 110

Thr Leu Val Thr Val Ser Ser
        115

<210> SEQ ID NO 24
<211> LENGTH: 121
<212> TYPE: PRT
<213> ORGANISM: Artificial Sequence
<220> FEATURE:
<223> OTHER INFORMATION: Synthetic_heavy chain variable region of
    anti-4-1BB antibody (mutated 1A10)

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Cys Leu Glu Trp Val
            35                  40                  45

Ser Trp Ile Ser Tyr Ser Gly Gly Ser Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Gly Gln Arg Asn Ser Met Arg Phe Asp Tyr Trp Gly
             100                 105                 110

Gln Gly Thr Leu Val Thr Val Ser Ser
         115                 120

<210> SEQ ID NO 25
<211> LENGTH: 121
<212> TYPE: PRT
<213> ORGANISM: Artificial Sequence
<220> FEATURE:
<223> OTHER INFORMATION: Synthetic_heavy chain variable region of
      anti-4-1BB antibody (mutated 1A10 M4, 1A10 M12)

<400> SEQUENCE: 25

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Asp Met Ser Trp Val Arg Gln Ala Pro Gly Lys Cys Leu Glu Trp Val
            35                  40                  45

Ser Trp Ile Ser Tyr Ser Gly Gly Ser Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Gln Arg Asn Ser Met Arg Glu Phe Asp Tyr Trp Gly
             100                 105                 110

Gln Gly Thr Leu Val Thr Val Ser Ser
         115                 120

<210> SEQ ID NO 26
<211> LENGTH: 121
<212> TYPE: PRT
<213> ORGANISM: Artificial Sequence
<220> FEATURE:
<223> OTHER INFORMATION: Synthetic_heavy chain variable region of
      anti-4-1BB antibody (mutated 1A10 M11, 1A10 M13)

<400> SEQUENCE: 26

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Asp Met Ser Trp Val Arg Gln Ala Pro Gly Lys Cys Leu Glu Trp Val
            35                  40                  45

Ser Trp Ile Ser Tyr Ser Gly Gly Ser Ile Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

```
Leu Gln Met Asn Ser Leu Arg Ala Glu Asp Thr Ala Val Tyr Tyr Cys
                85                  90                  95

Ala Arg Asp Ala Gln Arg Gln Ser Met Arg Glu Phe Tyr Trp Gly
            100                 105                 110

Gln Gly Thr Leu Val Thr Val Ser Ser
        115                 120
```

<210> SEQ ID NO 27
<211> LENGTH: 127
<212> TYPE: PRT
<213> ORGANISM: Artificial Sequence
<220> FEATURE:
<223> OTHER INFORMATION: Synthetic_heavy chain variable region of anti-4-1BB antibody (mutated 1A12)

<400> SEQUENCE: 27

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Cys Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125
```

<210> SEQ ID NO 28
<211> LENGTH: 127
<212> TYPE: PRT
<213> ORGANISM: Artificial Sequence
<220> FEATURE:
<223> OTHER INFORMATION: Synthetic_heavy chain variable region of anti-4-1BB antibody (mutated 1A12M1)

<400> SEQUENCE: 28

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Cys Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser
        115                 120                 125
```

```
<210> SEQ ID NO 29
<211> LENGTH: 119
<212> TYPE: PRT
<213> ORGANISM: Artificial Sequence
<220> FEATURE:
<223> OTHER INFORMATION: Synthetic_heavy chain variable region of
      anti-4-1BB antibody (mutated AB41)

<400> SEQUENCE: 29

Gln Val Gln Leu Gln Gln Ser Gly Ala Glu Val Ile Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Cys Leu Glu Trp Ile
        35                  40                  45

Gly Glu Ile Asn Pro Gly Asn Gly His Thr Asn Tyr Asn Glu Lys Phe
    50                  55                  60

Lys Ser Arg Ala Thr Leu Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Thr Thr Ala Arg Ala Phe Ala Tyr Trp Gly Gln Gly
            100                 105                 110

Thr Leu Val Thr Val Ser Ser
        115

<210> SEQ ID NO 30
<211> LENGTH: 110
<212> TYPE: PRT
<213> ORGANISM: Artificial Sequence
<220> FEATURE:
<223> OTHER INFORMATION: Synthetic_light chain variable region of
      anti-4-1BB antibody (1A10, 1A10 M4, 1A10 M11, 1A12)

<400> SEQUENCE: 30

Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
            20                  25                  30

Tyr Val Thr Trp Tyr Gln Gln Leu Pro Gly Thr Ala Pro Lys Leu Leu
        35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu
            100                 105                 110

<210> SEQ ID NO 31
<211> LENGTH: 110
<212> TYPE: PRT
<213> ORGANISM: Artificial Sequence
<220> FEATURE:
<223> OTHER INFORMATION: Synthetic_light chain variable region of
      anti-4-1BB antibody (1A10 M12, 1A10 M13, 1A12M1)

<400> SEQUENCE: 31

Gln Ser Val Leu Thr Gln Pro Pro Ser Ala Ser Gly Thr Pro Gly Gln
```

```
                1               5                  10                  15
            Arg Val Thr Ile Ser Cys Ser Gly Ser Ser Asn Ile Gly Asn Asn
                            20                  25                  30

Tyr Val Thr Trp Tyr Gln Gln Leu Pro Gly Thr Ala Pro Lys Leu Leu
                        35                  40                  45

Ile Tyr Ala Asp Ser His Arg Pro Ser Gly Val Pro Asp Arg Phe Ser
                    50                  55                  60

Gly Ser Lys Ser Gly Thr Ser Ala Ser Leu Ala Ile Ser Gly Leu Arg
            65                  70                  75                  80

Ser Glu Asp Glu Ala Asp Tyr Tyr Cys Ala Thr Trp Asp Tyr Ser Leu
                            85                  90                  95

Ser Gly Tyr Val Phe Gly Gly Gly Thr Lys Leu Thr Val Leu
                            100                 105                 110
```

<210> SEQ ID NO 32
<211> LENGTH: 108
<212> TYPE: PRT
<213> ORGANISM: Artificial Sequence
<220> FEATURE:
<223> OTHER INFORMATION: Synthetic_light chain variable region of
      anti-4-1BB antibody (AB41)

<400> SEQUENCE: 32

```
            Asp Ile Val Met Thr Gln Ser Pro Ala Phe Leu Ser Val Thr Pro Gly
            1               5                   10                  15

Glu Lys Val Thr Ile Thr Cys Arg Ala Ser Gln Thr Ile Ser Asp Tyr
                            20                  25                  30

Leu His Trp Tyr Gln Gln Lys Pro Asp Gln Ala Pro Lys Leu Leu Ile
                        35                  40                  45

Lys Tyr Ala Ser Gln Ser Ile Ser Gly Ile Pro Ser Arg Phe Ser Gly
                    50                  55                  60

Ser Gly Ser Gly Thr Asp Phe Thr Phe Thr Ile Ser Ser Leu Glu Ala
            65                  70                  75                  80

Glu Asp Ala Ala Thr Tyr Tyr Cys Gln Asp Gly His Ser Phe Pro Pro
                            85                  90                  95

Thr Phe Gly Gln Gly Thr Lys Leu Glu Ile Lys Arg
                            100                 105
```

<210> SEQ ID NO 33
<211> LENGTH: 110
<212> TYPE: PRT
<213> ORGANISM: Artificial Sequence
<220> FEATURE:
<223> OTHER INFORMATION: Synthetic_light chain variable region of
      anti-4-1BB antibody (mutated 1A10, 1A10 M4, 1A10 M11, 1A12)

<400> SEQUENCE: 33

```
            Gln Ser Val Leu Thr Gln Pro Pro Ser Ala Ser Gly Thr Pro Gly Arg
            1               5                   10                  15

Arg Val Thr Ile Ser Cys Ser Gly Ser Ser Asn Ile Gly Asn Asn
                            20                  25                  30

Tyr Val Thr Trp Tyr Gln Gln Leu Pro Gly Thr Ala Pro Lys Leu Leu
                        35                  40                  45

Ile Tyr Ala Asp Ser His Arg Pro Ser Gly Val Pro Asp Arg Phe Ser
                    50                  55                  60

Gly Ser Lys Ser Gly Thr Ser Ala Ser Leu Ala Ile Ser Gly Leu Arg
            65                  70                  75                  80

Ser Glu Asp Glu Ala Asp Tyr Tyr Cys Ala Thr Trp Asp Tyr Ser Leu
```

```
                        85                  90                  95

Ser Gly Tyr Val Phe Gly Cys Gly Thr Lys Leu Thr Val Leu
            100                 105                 110

<210> SEQ ID NO 34
<211> LENGTH: 110
<212> TYPE: PRT
<213> ORGANISM: Artificial Sequence
<220> FEATURE:
<223> OTHER INFORMATION: Synthetic_light chain variable region of
      anti-4-1BB antibody (mutated 1A10 M12, 1A10 M13, 1A12M1)

<400> SEQUENCE: 34

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
        50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Cys Gly Thr Lys Leu Thr Val Leu
            100                 105                 110

<210> SEQ ID NO 35
<211> LENGTH: 30
<212> TYPE: PRT
<213> ORGANISM: Artificial Sequence
<220> FEATURE:
<223> OTHER INFORMATION: Synthetic_H-FR1 of anti-4-1BB antibody

<400> SEQUENCE: 35

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 36
<211> LENGTH: 30
<212> TYPE: PRT
<213> ORGANISM: Artificial Sequence
<220> FEATURE:
<223> OTHER INFORMATION: Synthetic_H-FR1 of anti-4-1BB antibody

<400> SEQUENCE: 36

Gln Val Gln Leu Gln Gln Ser Gly Ala Glu Val Ile Lys Pro Gly Ala
1               5                   10                  15

Ser Val Lys Leu Ser Cys Lys Ala Ser Gly Tyr Thr Phe Ser
            20                  25                  30

<210> SEQ ID NO 37
<211> LENGTH: 14
<212> TYPE: PRT
<213> ORGANISM: Artificial Sequence
<220> FEATURE:
<223> OTHER INFORMATION: Synthetic_H-FR2 of anti-4-1BB antibody

<400> SEQUENCE: 37
```

-continued

Trp Val Arg Gln Ala Pro Gly Lys Gly Leu Glu Trp Val Ser
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic_H-FR2 of anti-4-1BB antibody

<400> SEQUENCE: 38

Trp Val Arg Gln Ala Pro Gly Gln Gly Leu Glu Trp Ile Gly
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic_H-FR2 of anti-4-1BB antibody

<400> SEQUENCE: 39

Trp Val Arg Gln Ala Pro Gly Lys Cys Leu Glu Trp Val Ser
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic_H-FR2 of anti-4-1BB antibody

<400> SEQUENCE: 40

Trp Val Arg Gln Ala Pro Gly Gln Cys Leu Glu Trp Ile Gly
1               5                   10

<210> SEQ ID NO 41
<211> LENGTH: 32
<212> TYPE: PRT
<213> ORGANISM: Artificial Sequence
<220> FEATURE:
<223> OTHER INFORMATION: Synthetic_H-FR3 of anti-4-1BB antibody

<400> SEQUENCE: 41

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
                20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic_H-FR3 of anti-4-1BB antibody

<400> SEQUENCE: 42

Arg Phe Thr Ile Ser Arg Asp Asn Ser Lys Asn Thr Leu Tyr Leu Gln
1               5                   10                  15

Met Asn Ser Leu Arg Ala Glu Asp Ala Ala Val Tyr Tyr Cys Ala Lys
                20                  25                  30

<210> SEQ ID NO 43
<211> LENGTH: 32
<212> TYPE: PRT
<213> ORGANISM: Artificial Sequence

```
<220> FEATURE:
<223> OTHER INFORMATION: Synthetic_H-FR3 of anti-4-1BB antibody

<400> SEQUENCE: 43

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 44
<211> LENGTH: 32
<212> TYPE: PRT
<213> ORGANISM: Artificial Sequence
<220> FEATURE:
<223> OTHER INFORMATION: Synthetic_H-FR3 of anti-4-1BB antibody

<400> SEQUENCE: 44

Arg Ala Thr Leu Thr Gly Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 45
<211> LENGTH: 11
<212> TYPE: PRT
<213> ORGANISM: Artificial Sequence
<220> FEATURE:
<223> OTHER INFORMATION: Synthetic_H-FR4 of anti-4-1BB antibody

<400> SEQUENCE: 45

Trp Gly Gln Gly Thr Leu Val Thr Val Ser Ser
1               5                   10

<210> SEQ ID NO 46
<211> LENGTH: 22
<212> TYPE: PRT
<213> ORGANISM: Artificial Sequence
<220> FEATURE:
<223> OTHER INFORMATION: Synthetic_L-FR1 of anti-4-1BB antibody

<400> SEQUENCE: 46

Gln Ser Val Leu Thr Gln Pro Pro Ser Ala Ser Gly Thr Pro Gly Arg
1               5                   10                  15

Arg Val Thr Ile Ser Cys
            20

<210> SEQ ID NO 47
<211> LENGTH: 22
<212> TYPE: PRT
<213> ORGANISM: Artificial Sequence
<220> FEATURE:
<223> OTHER INFORMATION: Synthetic_L-FR1 of anti-4-1BB antibody

<400> SEQUENCE: 47

Gln Ser Val Leu Thr Gln Pro Pro Ser Ala Ser Gly Thr Pro Gly Gln
1               5                   10                  15

Arg Val Thr Ile Ser Cys
            20

<210> SEQ ID NO 48
<211> LENGTH: 23
<212> TYPE: PRT
<213> ORGANISM: Artificial Sequence
<220> FEATURE:
<223> OTHER INFORMATION: Synthetic_L-FR1 of anti-4-1BB antibody
```

<400> SEQUENCE: 48

Asp Ile Val Met Thr Gln Ser Pro Ala Phe Leu Ser Val Thr Pro Gly
1               5                   10                  15

Glu Lys Val Thr Ile Thr Cys
            20

<210> SEQ ID NO 49
<211> LENGTH: 15
<212> TYPE: PRT
<213> ORGANISM: Artificial Sequence
<220> FEATURE:
<223> OTHER INFORMATION: Synthetic_L-FR2 of anti-4-1BB antibody

<400> SEQUENCE: 49

Trp Tyr Gln Gln Leu Pro Gly Thr Ala Pro Lys Leu Leu Ile Tyr
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Synthetic_L-FR2 of anti-4-1BB antibody

<400> SEQUENCE: 50

Trp Tyr Gln Gln Lys Pro Asp Gln Ala Pro Lys Leu Leu Ile Lys
1               5                   10                  15

<210> SEQ ID NO 51
<211> LENGTH: 32
<212> TYPE: PRT
<213> ORGANISM: Artificial Sequence
<220> FEATURE:
<223> OTHER INFORMATION: Synthetic_L-FR3 of anti-4-1BB antibody

<400> SEQUENCE: 51

Gly Val Pro Asp Arg Phe Ser Gly Ser Lys Ser Gly Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 52
<211> LENGTH: 32
<212> TYPE: PRT
<213> ORGANISM: Artificial Sequence
<220> FEATURE:
<223> OTHER INFORMATION: Synthetic_L-FR3 of anti-4-1BB antibody

<400> SEQUENCE: 52

Gly Ile Pro Ser Arg Phe Ser Gly Ser Gly Ser Gly Thr Asp Phe Thr
1               5                   10                  15

Phe Thr Ile Ser Ser Leu Glu Ala Glu Asp Ala Ala Thr Tyr Tyr Cys
            20                  25                  30

<210> SEQ ID NO 53
<211> LENGTH: 10
<212> TYPE: PRT
<213> ORGANISM: Artificial Sequence
<220> FEATURE:
<223> OTHER INFORMATION: Synthetic_L-FR4 of anti-4-1BB antibody

<400> SEQUENCE: 53

Phe Gly Gly Gly Thr Lys Leu Thr Val Leu
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Synthetic_L-FR4 of anti-4-1BB antibody

<400> SEQUENCE: 54

Phe Gly Gln Gly Thr Lys Leu Glu Ile Lys Arg
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic_L-FR4 of anti-4-1BB antibody

<400> SEQUENCE: 55

Phe Gly Cys Gly Thr Lys Leu Thr Val Leu
1               5                   10

<210> SEQ ID NO 56
<211> LENGTH: 448
<212> TYPE: PRT
<213> ORGANISM: Artificial Sequence
<220> FEATURE:
<223> OTHER INFORMATION: Synthetic_heavy chain of anti-4-1BB antibody

<400> SEQUENCE: 56

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gln Arg Asn Ser Met Arg Glu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

-continued

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
        260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 57
<211> LENGTH: 448
<212> TYPE: PRT
<213> ORGANISM: Artificial Sequence
<220> FEATURE:
<223> OTHER INFORMATION: Synthetic_heavy chain of anti-4-1BB antibody

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
        35                  40                  45

Ser Trp Ile Ser Tyr Ser Gly Gly Ser Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gln Arg Asn Ser Met Arg Glu Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
            195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
            405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
            435                 440                 445

<210> SEQ ID NO 58
<211> LENGTH: 448
<212> TYPE: PRT
<213> ORGANISM: Artificial Sequence
<220> FEATURE:
<223> OTHER INFORMATION: Synthetic_heavy chain of anti-4-1BB antibody

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Asp Met Ser Trp Val Arg Gln Ala Pro Gly Lys Gly Leu Glu Trp Val
            35                  40                  45

Ser Trp Ile Ser Tyr Ser Gly Ser Ile Tyr Tyr Ala Asp Ser Val
50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Ala Gln Arg Gln Ser Met Arg Glu Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 59
<211> LENGTH: 454
<212> TYPE: PRT
<213> ORGANISM: Artificial Sequence
<220> FEATURE:
<223> OTHER INFORMATION: Synthetic_heavy chain of anti-4-1BB antibody
```

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
        35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Ala Ala Val Tyr Tyr Cys
            85                  90                  95

Ala Lys His Gly Gly Gln Lys Pro Thr Thr Lys Ser Ser Ala Tyr
            100                 105                 110

Gly Met Asp Gly Trp Gly Gln Gly Thr Leu Val Thr Val Ser Ser Ala
        115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
            165                 170                 175

Val His Thr Phe Pro Ala Val Leu Gln Ser Ser Gly Leu Tyr Ser Leu
        180                 185                 190

Ser Ser Val Val Thr Val Pro Ser Ser Ser Leu Gly Thr Lys Thr Tyr
    195                 200                 205

Thr Cys Asn Val Asp His Lys Pro Ser Asn Thr Lys Val Asp Lys Arg
210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
            245                 250                 255

Thr Leu Met Ile Ser Arg Thr Pro Glu Val Thr Cys Val Val Val Asp
        260                 265                 270

Val Ser Gln Glu Asp Pro Glu Val Gln Phe Asn Trp Tyr Val Asp Gly
    275                 280                 285

Val Glu Val His Asn Ala Lys Thr Lys Pro Arg Glu Glu Gln Phe Asn
290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
            325                 330                 335

Ser Ser Ile Glu Lys Thr Ile Ser Lys Ala Lys Gly Gln Pro Arg Glu
        340                 345                 350

Pro Gln Val Tyr Thr Leu Pro Pro Ser Gln Glu Glu Met Thr Lys Asn
    355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg

```
                405                 410                 415
Leu Thr Val Asp Lys Ser Arg Trp Gln Glu Gly Asn Val Phe Ser Cys
            420                 425                 430

Ser Val Met His Glu Ala Leu His Asn His Tyr Thr Gln Lys Ser Leu
            435                 440                 445

Ser Leu Ser Leu Gly Lys
    450

<210> SEQ ID NO 60
<211> LENGTH: 454
<212> TYPE: PRT
<213> ORGANISM: Artificial Sequence
<220> FEATURE:
<223> OTHER INFORMATION: Synthetic_heavy chain of anti-4-1BB antibody

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Asp Met Ser Trp Val Arg Gln Ala Pro Gly Lys Gly Leu Glu Trp Val
            35                  40                  45

Ser Val Ile Tyr Pro Asp Asp Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Gly Gly Gln Lys Pro Thr Thr Lys Ser Ser Ser Ala Tyr
            100                 105                 110

Gly Met Asp Gly Trp Gly Gln Gly Thr Leu Val Thr Val Ser Ser Ala
            115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Lys Thr Tyr
            195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser Gln Glu Asp Pro Glu Val Gln Phe Asn Trp Tyr Val Asp Gly
            275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
```

```
            305                 310                 315                 320
Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
                340                 345                 350

Pro Gln Val Tyr Thr Leu Pro Pro Ser Gln Glu Glu Met Thr Lys Asn
                355                 360                 365

Gln Val Ser Leu Thr Cys Leu Val Lys Gly Phe Tyr Pro Ser Asp Ile
            370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
                420                 425                 430

Ser Val Met His Glu Ala Leu His Asn His Tyr Thr Gln Lys Ser Leu
                435                 440                 445

Ser Leu Ser Leu Gly Lys
    450

<210> SEQ ID NO 61
<211> LENGTH: 446
<212> TYPE: PRT
<213> ORGANISM: Artificial Sequence
<220> FEATURE:
<223> OTHER INFORMATION: Synthetic_heavy chain of anti-4-1BB antibody

<400> SEQUENCE: 61

Gln Val Gln Leu Gln Gln Ser Gly Ala Glu Val Ile Lys Pro Gly Ala
1               5                   10                  15

Ser Val Lys Leu Ser Cys Lys Ala Ser Gly Tyr Thr Phe Ser Ser Tyr
                20                  25                  30

Trp Met His Trp Val Arg Gln Ala Pro Gly Gln Gly Leu Glu Trp Ile
            35                  40                  45

Gly Glu Ile Asn Pro Gly Asn Gly His Thr Asn Tyr Asn Glu Lys Phe
        50                  55                  60

Lys Ser Arg Ala Thr Leu Thr Gly Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Phe Thr Thr Ala Arg Ala Phe Ala Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
```

```
            210                 215                 220
Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 62
<211> LENGTH: 216
<212> TYPE: PRT
<213> ORGANISM: Artificial Sequence
<220> FEATURE:
<223> OTHER INFORMATION: Synthetic_light chain of anti-4-1BB antibody

<400> SEQUENCE: 62

Gln Ser Val Leu Thr Gln Pro Pro Ser Ala Ser Gly Thr Pro Gly Arg
1               5                   10                  15

Arg Val Thr Ile Ser Cys Ser Gly Ser Ser Ser Asn Ile Gly Asn Asn
                20                  25                  30

Tyr Val Thr Trp Tyr Gln Gln Leu Pro Gly Thr Ala Pro Lys Leu Leu
            35                  40                  45

Ile Tyr Ala Asp Ser His Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
```

```
                130              135              140
Pro Gly Ala Val Thr Val Ala Trp Lys Ala Asp Ser Ser Pro Val Lys
145                 150              155                 160

Ala Gly Val Glu Thr Thr Thr Pro Ser Lys Gln Ser Asn Asn Lys Tyr
                165              170                 175

Ala Ala Ser Ser Tyr Leu Ser Leu Thr Pro Glu Gln Trp Lys Ser His
                180              185                 190

Arg Ser Tyr Ser Cys Gln Val Thr His Glu Gly Ser Thr Val Glu Lys
                195              200              205

Thr Val Ala Pro Ala Glu Cys Ser
        210              215

<210> SEQ ID NO 63
<211> LENGTH: 216
<212> TYPE: PRT
<213> ORGANISM: Artificial Sequence
<220> FEATURE:
<223> OTHER INFORMATION: Synthetic_light chain of anti-4-1BB antibody

<400> SEQUENCE: 63

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Asn Asn
            20                  25                  30

Tyr Val Thr Trp Tyr Gln Gln Leu Pro Gly Thr Ala Pro Lys Leu Leu
                35                  40                  45

Ile Tyr Ala Asp Ser His Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Tyr Ser Leu
                85                  90                  95

Ser Gly Tyr Val Phe Gly Gly Gly Thr Lys Leu Thr Val Leu Gly Gln
                100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
                180                 185                 190

Arg Ser Tyr Ser Cys Gln Val Thr His Glu Gly Ser Thr Val Glu Lys
                195                 200                 205

Thr Val Ala Pro Ala Glu Cys Ser
        210                 215

<210> SEQ ID NO 64
<211> LENGTH: 214
<212> TYPE: PRT
<213> ORGANISM: Artificial Sequence
<220> FEATURE:
<223> OTHER INFORMATION: Synthetic_light chain of anti-4-1BB antibody

<400> SEQUENCE: 64
```

-continued

```
Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30

Leu His Trp Tyr Gln Gln Lys Pro Asp Gln Ala Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Phe Pro Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 5
<212> TYPE: PRT
<213> ORGANISM: Artificial Sequence
<220> FEATURE:
<223> OTHER INFORMATION: Synthetic_H-CDR1 of anti-HER2 antibody

<400> SEQUENCE: 65

Asp Thr Tyr Ile His
1               5

<210> SEQ ID NO 66
<211> LENGTH: 17
<212> TYPE: PRT
<213> ORGANISM: Artificial Sequence
<220> FEATURE:
<223> OTHER INFORMATION: Synthetic_H-CDR2 of anti-HER2 antibody

<400> SEQUENCE: 66

Arg Ile Tyr Pro Thr Asn Gly Tyr Thr Arg Tyr Ala Asp Ser Val Lys
1               5                   10                  15

Gly

<210> SEQ ID NO 67
<211> LENGTH: 11
<212> TYPE: PRT
<213> ORGANISM: Artificial Sequence
<220> FEATURE:
<223> OTHER INFORMATION: Synthetic_H-CDR3 of anti-HER2 antibody

<400> SEQUENCE: 67
```

```
Trp Gly Gly Asp Gly Phe Tyr Ala Met Asp Tyr
1               5                   10
```

<210> SEQ ID NO 68
<211> LENGTH: 11
<212> TYPE: PRT
<213> ORGANISM: Artificial Sequence
<220> FEATURE:
<223> OTHER INFORMATION: Synthetic_L-CDR1 of anti-HER2 antibody

<400> SEQUENCE: 68

```
Arg Ala Ser Gln Asp Val Asn Thr Ala Val Ala
1               5                   10
```

<210> SEQ ID NO 69
<211> LENGTH: 7
<212> TYPE: PRT
<213> ORGANISM: Artificial Sequence
<220> FEATURE:
<223> OTHER INFORMATION: Synthetic_L-CDR2 of anti-HER2 antibody

<400> SEQUENCE: 69

```
Ser Ala Ser Phe Leu Tyr Ser
1               5
```

<210> SEQ ID NO 70
<211> LENGTH: 9
<212> TYPE: PRT
<213> ORGANISM: Artificial Sequence
<220> FEATURE:
<223> OTHER INFORMATION: Synthetic_L-CDR3 of anti-HER2 antibody

<400> SEQUENCE: 70

```
Gln Gln His Tyr Thr Thr Pro Pro Thr
1               5
```

<210> SEQ ID NO 71
<211> LENGTH: 119
<212> TYPE: PRT
<213> ORGANISM: Artificial Sequence
<220> FEATURE:
<223> OTHER INFORMATION: Synthetic_heavy chain variable region of
      anti-HER2 antibody

<400> SEQUENCE: 71

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser
        115
```

```
<210> SEQ ID NO 72
<211> LENGTH: 108
<212> TYPE: PRT
<213> ORGANISM: Artificial Sequence
<220> FEATURE:
<223> OTHER INFORMATION: Synthetic_light chain variable region of
      anti-HER2 antibody

<400> SEQUENCE: 72

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg
            100                 105

<210> SEQ ID NO 73
<211> LENGTH: 450
<212> TYPE: PRT
<213> ORGANISM: Artificial Sequence
<220> FEATURE:
<223> OTHER INFORMATION: Synthetic_heavy chain of anti-HER2 antibody

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 74
<211> LENGTH: 450
<212> TYPE: PRT
<213> ORGANISM: Artificial Sequence
<220> FEATURE:
<223> OTHER INFORMATION: Synthetic_heavy chain of anti-HER2 antibody
      (N297A)

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
```

100                 105                 110
Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 75
<211> LENGTH: 214
<212> TYPE: PRT
<213> ORGANISM: Artificial Sequence
<220> FEATURE:
<223> OTHER INFORMATION: Synthetic_light chain of anti-HER2 antibody

<400> SEQUENCE: 75

Asp Ile Gln Met Thr Gln Ser Pro Ser Ser Leu Ser Ala Ser Val Gly

```
  1               5                  10                 15
Asp Arg Val Thr Ile Thr Cys Arg Ala Ser Gln Asp Val Asn Thr Ala
                20                 25                 30

Val Ala Trp Tyr Gln Gln Lys Pro Gly Lys Ala Pro Lys Leu Leu Ile
                35                 40                 45

Tyr Ser Ala Ser Phe Leu Tyr Ser Gly Val Pro Ser Arg Phe Ser Gly
            50                 55                 60

Ser Arg Ser Gly Thr Asp Phe Thr Leu Thr Ile Ser Ser Leu Gln Pro
65                 70                 75                 80

Glu Asp Phe Ala Thr Tyr Tyr Cys Gln Gln His Tyr Thr Thr Pro Pro
                85                 90                 95

Thr Phe Gly Gln Gly Thr Lys Val Glu Ile Lys Arg Thr Val Ala Ala
                100                105                110

Pro Ser Val Phe Ile Phe Pro Pro Ser Asp Glu Gln Leu Lys Ser Gly
                115                120                125

Thr Ala Ser Val Val Cys Leu Leu Asn Asn Phe Tyr Pro Arg Glu Ala
            130                135                140

Lys Val Gln Trp Lys Val Asp Asn Ala Leu Gln Ser Gly Asn Ser Gln
145                150                155                160

Glu Ser Val Thr Glu Gln Asp Ser Lys Asp Ser Thr Tyr Ser Leu Ser
                165                170                175

Ser Thr Leu Thr Leu Ser Lys Ala Asp Tyr Glu Lys His Lys Val Tyr
            180                185                190

Ala Cys Glu Val Thr His Gln Gly Leu Ser Ser Pro Val Thr Lys Ser
                195                200                205

Phe Asn Arg Gly Glu Cys
            210

<210> SEQ ID NO 76
<211> LENGTH: 716
<212> TYPE: PRT
<213> ORGANISM: Artificial Sequence
<220> FEATURE:
<223> OTHER INFORMATION: Synthetic_heavy chain of bispecific antibody
      (HER2(NA)x1A10)

<400> SEQUENCE: 76

Glu Val Gln Leu Val Glu Ser Gly Gly Gly Leu Val Gln Pro Gly Gly
1               5                  10                 15

Ser Leu Arg Leu Ser Cys Ala Ala Ser Gly Phe Asn Ile Lys Asp Thr
                20                 25                 30

Tyr Ile His Trp Val Arg Gln Ala Pro Gly Lys Gly Leu Glu Trp Val
                35                 40                 45

Ala Arg Ile Tyr Pro Thr Asn Gly Tyr Thr Arg Tyr Ala Asp Ser Val
            50                 55                 60

Lys Gly Arg Phe Thr Ile Ser Ala Asp Thr Ser Lys Asn Thr Ala Tyr
65                 70                 75                 80

Leu Gln Met Asn Ser Leu Arg Ala Glu Asp Thr Ala Val Tyr Tyr Cys
                85                 90                 95

Ser Arg Trp Gly Gly Asp Gly Phe Tyr Ala Met Asp Tyr Trp Gly Gln
                100                105                110

Gly Thr Leu Val Thr Val Ser Ser Ala Ser Thr Lys Gly Pro Ser Val
            115                120                125

Phe Pro Leu Ala Pro Ser Ser Lys Ser Thr Ser Gly Gly Thr Ala Ala
            130                135                140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Ser Gly Gly Gly Gly
    450                 455                 460

Ser Gln Ser Val Leu Thr Gln Pro Pro Ser Ala Ser Gly Thr Pro Gly
465                 470                 475                 480

Arg Arg Val Thr Ile Ser Cys Ser Gly Ser Ser Ser Asn Ile Gly Asn
                485                 490                 495

Asn Tyr Val Thr Trp Tyr Gln Gln Leu Pro Gly Thr Ala Pro Lys Leu
            500                 505                 510

Leu Ile Tyr Ala Asp Ser His Arg Pro Ser Gly Val Pro Asp Arg Phe
        515                 520                 525

Ser Gly Ser Lys Ser Gly Thr Ser Ala Ser Leu Ala Ile Ser Gly Leu
    530                 535                 540

Arg Ser Glu Asp Glu Ala Asp Tyr Tyr Cys Ala Thr Trp Asp Tyr Ser
545                 550                 555                 560

Leu Ser Gly Tyr Val Phe Gly Cys Gly Thr Lys Leu Thr Val Leu Gly
```

```
                        565                 570                 575
Gly Gly Gly Ser Gly Gly Gly Ser Gly Gly Gly Ser Gly Gly
                580                 585                 590

Gly Gly Ser Glu Val Gln Leu Leu Glu Ser Gly Gly Leu Val Gln
            595                 600                 605

Pro Gly Gly Ser Leu Arg Leu Ser Cys Ala Ala Ser Gly Phe Thr Phe
    610                 615                 620

Ser Ser Tyr Asp Met Ser Trp Val Arg Gln Ala Pro Gly Lys Cys Leu
625                 630                 635                 640

Glu Trp Val Ser Trp Ile Ser Tyr Ser Gly Ser Ile Tyr Tyr Ala
                645                 650                 655

Asp Ser Val Lys Gly Arg Phe Thr Ile Ser Arg Asp Asn Ser Lys Asn
                660                 665                 670

Thr Leu Tyr Leu Gln Met Asn Ser Leu Arg Ala Glu Asp Thr Ala Val
                675                 680                 685

Tyr Tyr Cys Ala Arg Asp Gly Gln Arg Asn Ser Met Arg Glu Phe Asp
                690                 695                 700

Tyr Trp Gly Gln Gly Thr Leu Val Thr Val Ser Ser
705                 710                 715

<210> SEQ ID NO 77
<211> LENGTH: 719
<212> TYPE: PRT
<213> ORGANISM: Artificial Sequence
<220> FEATURE:
<223> OTHER INFORMATION: Synthetic_heavy chain of bispecific antibody
      (HER2 (NA)x1A10 GSLH)

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

```
Pro Ser Asn Thr Lys Val Asp Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Ser Gly Ser Gly Ser Gly Ser Gly Ser Gly Ser Gly Ser
    450                 455                 460

Gly Ser Gly Ser Gln Ser Val Leu Thr Gln Pro Pro Ser Ala Ser Gly
465                 470                 475                 480

Thr Pro Gly Arg Arg Val Thr Ile Ser Cys Ser Gly Ser Ser Ser Asn
            485                 490                 495

Ile Gly Asn Asn Tyr Val Thr Trp Tyr Gln Gln Leu Pro Gly Thr Ala
            500                 505                 510

Pro Lys Leu Leu Ile Tyr Ala Asp Ser His Arg Pro Ser Gly Val Pro
            515                 520                 525

Asp Arg Phe Ser Gly Ser Lys Ser Gly Thr Ser Ala Ser Leu Ala Ile
530                 535                 540

Ser Gly Leu Arg Ser Glu Asp Glu Ala Asp Tyr Tyr Cys Ala Thr Trp
545                 550                 555                 560

Asp Tyr Ser Leu Ser Gly Tyr Val Phe Gly Cys Gly Thr Lys Leu Thr
            565                 570                 575

Val Leu Gly Gly Gly Gly Ser Gly Gly Gly Gly Ser Gly Gly Gly Gly
            580                 585                 590

Ser Gly Gly Gly Gly Ser Glu Val Gln Leu Leu Glu Ser Gly Gly Gly
            595                 600                 605

Leu Val Gln Pro Gly Gly Ser Leu Arg Leu Ser Cys Ala Ala Ser Gly
610                 615                 620

Phe Thr Phe Ser Ser Tyr Asp Met Ser Trp Val Arg Gln Ala Pro Gly
```

```
                625                 630                 635                 640
Lys Cys Leu Glu Trp Val Ser Trp Ile Ser Tyr Ser Gly Gly Ser Ile
                        645                 650                 655

Tyr Tyr Ala Asp Ser Val Lys Gly Arg Phe Thr Ile Ser Arg Asp Asn
                660                 665                 670

Ser Lys Asn Thr Leu Tyr Leu Gln Met Asn Ser Leu Arg Ala Glu Asp
            675                 680                 685

Thr Ala Val Tyr Tyr Cys Ala Arg Asp Gly Gln Arg Asn Ser Met Arg
690                 695                 700

Glu Phe Asp Tyr Trp Gly Gln Gly Thr Leu Val Thr Val Ser Ser
705                 710                 715
```

<210> SEQ ID NO 78
<211> LENGTH: 719
<212> TYPE: PRT
<213> ORGANISM: Artificial Sequence
<220> FEATURE:
<223> OTHER INFORMATION: Synthetic_heavy chain of bispecific antibody
      (HER2(NA)x1A10 M4)

<400> SEQUENCE: 78

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
            275                 280                 285
Asn Ala Lys Thr Lys Pro Arg Glu Glu Gln Tyr Ala Ser Thr Tyr Arg
        290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
        355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys Gly Ser Gly Ser Ser Gly Ser Gly Ser Gly Ser Gly Ser Ser
450                 455                 460
Gly Ser Gly Ser Gln Ser Val Leu Thr Gln Pro Pro Ser Ala Ser Gly
465                 470                 475                 480
Thr Pro Gly Arg Arg Val Thr Ile Ser Cys Ser Gly Ser Ser Ser Asn
                485                 490                 495
Ile Gly Asn Asn Tyr Val Thr Trp Tyr Gln Gln Leu Pro Gly Thr Ala
            500                 505                 510
Pro Lys Leu Leu Ile Tyr Ala Asp Ser His Arg Pro Ser Gly Val Pro
        515                 520                 525
Asp Arg Phe Ser Gly Ser Lys Ser Gly Thr Ser Ala Ser Leu Ala Ile
530                 535                 540
Ser Gly Leu Arg Ser Glu Asp Glu Ala Asp Tyr Tyr Cys Ala Thr Trp
545                 550                 555                 560
Asp Tyr Ser Leu Ser Gly Tyr Val Phe Gly Cys Gly Thr Lys Leu Thr
                565                 570                 575
Val Leu Gly Gly Gly Gly Ser Gly Gly Gly Gly Ser Gly Gly Gly Gly
            580                 585                 590
Ser Gly Gly Gly Gly Ser Glu Val Gln Leu Leu Glu Ser Gly Gly Gly
        595                 600                 605
Leu Val Gln Pro Gly Gly Ser Leu Arg Leu Ser Cys Ala Ala Ser Gly
610                 615                 620
Phe Thr Phe Ser Ser Tyr Asp Met Ser Trp Val Arg Gln Ala Pro Gly
625                 630                 635                 640
Lys Cys Leu Glu Trp Val Ser Trp Ile Ser Tyr Ser Gly Gly Ser Ile
                645                 650                 655
Tyr Tyr Ala Asp Ser Val Lys Gly Arg Phe Thr Ile Ser Arg Asp Asn
            660                 665                 670
Ser Lys Asn Thr Leu Tyr Leu Gln Met Asn Ser Leu Arg Ala Glu Asp
        675                 680                 685
Thr Ala Val Tyr Tyr Cys Ala Arg Asp Ala Gln Arg Asn Ser Met Arg
```

```
                690                 695                 700
Glu Phe Asp Tyr Trp Gly Gln Gly Thr Leu Val Thr Val Ser Ser
705                 710                 715
```

<210> SEQ ID NO 79
<211> LENGTH: 719
<212> TYPE: PRT
<213> ORGANISM: Artificial Sequence
<220> FEATURE:
<223> OTHER INFORMATION: Synthetic heavy chain of bispecific antibody
      (HER2(NA)x1A10 M12)

<400> SEQUENCE: 79

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335
```

```
Lys Thr Ile Ser Lys Ala Lys Gly Gln Pro Arg Glu Pro Gln Val Tyr
                340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
        370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
        435                 440                 445
Gly Lys Gly Ser Gly Ser Gly Ser Gly Ser Gly Ser Gly Ser Gly Ser
    450                 455                 460
Gly Ser Gly Ser Gln Ser Val Leu Thr Gln Pro Pro Ser Ala Ser Gly
465                 470                 475                 480
Thr Pro Gly Gln Arg Val Thr Ile Ser Cys Ser Gly Ser Ser Ser Asn
                485                 490                 495
Ile Gly Asn Asn Tyr Val Thr Trp Tyr Gln Gln Leu Pro Gly Thr Ala
            500                 505                 510
Pro Lys Leu Leu Ile Tyr Ala Asp Ser His Arg Pro Ser Gly Val Pro
        515                 520                 525
Asp Arg Phe Ser Gly Ser Lys Ser Gly Thr Ser Ala Ser Leu Ala Ile
530                 535                 540
Ser Gly Leu Arg Ser Glu Asp Glu Ala Asp Tyr Tyr Cys Ala Thr Trp
545                 550                 555                 560
Asp Tyr Ser Leu Ser Gly Tyr Val Phe Gly Cys Gly Thr Lys Leu Thr
                565                 570                 575
Val Leu Gly Gly Gly Gly Ser Gly Gly Gly Gly Ser Gly Gly Gly Gly
            580                 585                 590
Ser Gly Gly Gly Gly Ser Glu Val Gln Leu Leu Glu Ser Gly Gly Gly
        595                 600                 605
Leu Val Gln Pro Gly Gly Ser Leu Arg Leu Ser Cys Ala Ala Ser Gly
610                 615                 620
Phe Thr Phe Ser Ser Tyr Asp Met Ser Trp Val Arg Gln Ala Pro Gly
625                 630                 635                 640
Lys Cys Leu Glu Trp Val Ser Trp Ile Ser Tyr Ser Gly Gly Ser Ile
                645                 650                 655
Tyr Tyr Ala Asp Ser Val Lys Gly Arg Phe Thr Ile Ser Arg Asp Asn
            660                 665                 670
Ser Lys Asn Thr Leu Tyr Leu Gln Met Asn Ser Leu Arg Ala Glu Asp
        675                 680                 685
Thr Ala Val Tyr Tyr Cys Ala Arg Asp Ala Gln Arg Asn Ser Met Arg
690                 695                 700
Glu Phe Asp Tyr Trp Gly Gln Gly Thr Leu Val Thr Val Ser Ser
705                 710                 715

<210> SEQ ID NO 80
<211> LENGTH: 722
<212> TYPE: PRT
<213> ORGANISM: Artificial Sequence
<220> FEATURE:
<223> OTHER INFORMATION: Synthetic_heavy chain of bispecific antibody
```

-continued (HER2(NA)x1A12)

<400> SEQUENCE: 80

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

```
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Gly Gly Gly Ser Gly Gly Gly Gly Ser Gly Gly Gly Gly
    450                 455                 460

Ser Gln Ser Val Leu Thr Gln Pro Pro Ser Ala Ser Gly Thr Pro Gly
465                 470                 475                 480

Arg Arg Val Thr Ile Ser Cys Ser Gly Ser Ser Ser Asn Ile Gly Asn
                485                 490                 495

Asn Tyr Val Thr Trp Tyr Gln Gln Leu Pro Gly Thr Ala Pro Lys Leu
            500                 505                 510

Leu Ile Tyr Ala Asp Ser His Arg Pro Ser Gly Val Pro Asp Arg Phe
        515                 520                 525

Ser Gly Ser Lys Ser Gly Thr Ser Ala Ser Leu Ala Ile Ser Gly Leu
    530                 535                 540

Arg Ser Glu Asp Glu Ala Asp Tyr Tyr Cys Ala Thr Trp Asp Tyr Ser
545                 550                 555                 560

Leu Ser Gly Tyr Val Phe Gly Cys Gly Thr Lys Leu Thr Val Leu Gly
                565                 570                 575

Gly Gly Gly Ser Gly Gly Gly Ser Gly Gly Gly Ser Gly Gly
            580                 585                 590

Gly Gly Ser Glu Val Gln Leu Leu Glu Ser Gly Gly Leu Val Gln
        595                 600                 605

Pro Gly Gly Ser Leu Arg Leu Ser Cys Ala Ala Ser Gly Phe Thr Phe
    610                 615                 620

Ser Gly Tyr Asp Met Ser Trp Val Arg Gln Ala Pro Gly Lys Cys Leu
625                 630                 635                 640

Glu Trp Val Ser Val Ile Tyr Pro Asp Asp Gly Asn Thr Tyr Tyr Ala
                645                 650                 655

Asp Ser Val Lys Gly Arg Phe Thr Ile Ser Arg Asp Asn Ser Lys Asn
            660                 665                 670

Thr Leu Tyr Leu Gln Met Asn Ser Leu Arg Ala Glu Asp Ala Ala Val
        675                 680                 685

Tyr Tyr Cys Ala Lys His Gly Gly Gln Lys Pro Thr Thr Lys Ser Ser
    690                 695                 700

Ser Ala Tyr Gly Met Asp Gly Trp Gly Gln Gly Thr Leu Val Thr Val
705                 710                 715                 720

Ser Ser

<210> SEQ ID NO 81
<211> LENGTH: 725
<212> TYPE: PRT
<213> ORGANISM: Artificial Sequence
<220> FEATURE:
<223> OTHER INFORMATION: Synthetic_heavy chain of bispecific antibody
      (HER2(NA)x1A12 GSLH)

<400> SEQUENCE: 81

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

-continued

```
Tyr Ile His Trp Val Arg Gln Ala Pro Gly Lys Gly Leu Glu Trp Val
         35                  40                  45
Ala Arg Ile Tyr Pro Thr Asn Gly Tyr Thr Arg Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ser Arg Trp Gly Gly Asp Gly Phe Tyr Ala Met Asp Tyr Trp Gly Gln
             100                 105                 110
Gly Thr Leu Val Thr Val Ser Ser Ala Ser Thr Lys Gly Pro Ser Val
         115                 120                 125
Phe Pro Leu Ala Pro Ser Ser Lys Ser Thr Ser Gly Gly Thr Ala Ala
130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                 165                 170                 175
Leu Gln Ser Ser Gly Leu Tyr Ser Leu Ser Ser Val Val Thr Val Pro
             180                 185                 190
Ser Ser Ser Leu Gly Thr Gln Thr Tyr Ile Cys Asn Val Asn His Lys
         195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                 245                 250                 255
Ser Arg Thr Pro Glu Val Thr Cys Val Val Val Asp Val Ser His Glu
             260                 265                 270
Asp Pro Glu Val Lys Phe Asn Trp Tyr Val Asp Gly Val Glu Val His
         275                 280                 285
Asn Ala Lys Thr Lys Pro Arg Glu Glu Gln Tyr Ala Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                 325                 330                 335
Lys Thr Ile Ser Lys Ala Lys Gly Gln Pro Arg Glu Pro Gln Val Tyr
             340                 345                 350
Thr Leu Pro Pro Ser Arg Glu Glu Met Thr Lys Asn Gln Val Ser Leu
         355                 360                 365
Thr Cys Leu Val Lys Gly Phe Tyr Pro Ser Asp Ile Ala Val Glu Trp
370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                 405                 410                 415
Lys Ser Arg Trp Gln Gln Gly Asn Val Phe Ser Cys Ser Val Met His
             420                 425                 430
Glu Ala Leu His Asn His Tyr Thr Gln Lys Ser Leu Ser Leu Ser Pro
         435                 440                 445
Gly Lys Gly Ser Gly Ser Gly Ser Gly Ser Gly Ser Gly Ser Gly Ser
```

```
              450                 455                 460
Gly Ser Gly Ser Gln Ser Val Leu Thr Gln Pro Ser Ala Ser Gly
465                 470                 475                 480

Thr Pro Gly Arg Arg Val Thr Ile Ser Cys Ser Gly Ser Ser Asn
                485                 490                 495

Ile Gly Asn Asn Tyr Val Thr Trp Tyr Gln Gln Leu Pro Gly Thr Ala
                500                 505                 510

Pro Lys Leu Leu Ile Tyr Ala Asp Ser His Arg Pro Ser Gly Val Pro
                515                 520                 525

Asp Arg Phe Ser Gly Ser Lys Ser Gly Thr Ser Ala Ser Leu Ala Ile
                530                 535                 540

Ser Gly Leu Arg Ser Glu Asp Glu Ala Asp Tyr Tyr Cys Ala Thr Trp
545                 550                 555                 560

Asp Tyr Ser Leu Ser Gly Tyr Val Phe Gly Cys Gly Thr Lys Leu Thr
                565                 570                 575

Val Leu Gly Gly Gly Gly Ser Gly Gly Gly Gly Ser Gly Gly Gly Gly
                580                 585                 590

Ser Gly Gly Gly Gly Ser Glu Val Gln Leu Leu Glu Ser Gly Gly Gly
                595                 600                 605

Leu Val Gln Pro Gly Gly Ser Leu Arg Leu Ser Cys Ala Ala Ser Gly
                610                 615                 620

Phe Thr Phe Ser Gly Tyr Asp Met Ser Trp Val Arg Gln Ala Pro Gly
625                 630                 635                 640

Lys Cys Leu Glu Trp Val Ser Val Ile Tyr Pro Asp Asp Gly Asn Thr
                645                 650                 655

Tyr Tyr Ala Asp Ser Val Lys Gly Arg Phe Thr Ile Ser Arg Asp Asn
                660                 665                 670

Ser Lys Asn Thr Leu Tyr Leu Gln Met Asn Ser Leu Arg Ala Glu Asp
                675                 680                 685

Ala Ala Val Tyr Tyr Cys Ala Lys His Gly Gly Gln Lys Pro Thr Thr
                690                 695                 700

Lys Ser Ser Ser Ala Tyr Gly Met Asp Gly Trp Gly Gln Gly Thr Leu
705                 710                 715                 720

Val Thr Val Ser Ser
                725

<210> SEQ ID NO 82
<211> LENGTH: 725
<212> TYPE: PRT
<213> ORGANISM: Artificial Sequence
<220> FEATURE:
<223> OTHER INFORMATION: Synthetic_heavy chain of bispecific antibody
      (HER2(NA)x1A12 M1)

<400> SEQUENCE: 82

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
                35                  40                  45

Ala Arg Ile Tyr Pro Thr Asn Gly Tyr Thr Arg Tyr Ala Asp Ser Val
                50                  55                  60

Lys Gly Arg Phe Thr Ile Ser Ala Asp Thr Ser Lys Asn Thr Ala Tyr
65                  70                  75                  80
```

-continued

```
Leu Gln Met Asn Ser Leu Arg Ala Glu Asp Thr Ala Val Tyr Tyr Cys
                 85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Ala Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Ser Gly Ser Gly Ser Gly Ser Gly Ser Gly Ser Gly Ser
450                 455                 460

Gly Ser Gly Ser Gln Ser Val Leu Thr Gln Pro Pro Ser Ala Ser Gly
465                 470                 475                 480

Thr Pro Gly Gln Arg Val Thr Ile Ser Cys Ser Gly Ser Ser Ser Asn
                485                 490                 495

Ile Gly Asn Asn Tyr Val Thr Trp Tyr Gln Gln Leu Pro Gly Thr Ala
```

```
                        500                 505                 510
Pro Lys Leu Leu Ile Tyr Ala Asp Ser His Arg Pro Ser Gly Val Pro
            515                 520                 525

Asp Arg Phe Ser Gly Ser Lys Ser Gly Thr Ser Ala Ser Leu Ala Ile
        530                 535                 540

Ser Gly Leu Arg Ser Glu Asp Glu Ala Asp Tyr Tyr Cys Ala Thr Trp
545                 550                 555                 560

Asp Tyr Ser Leu Ser Gly Tyr Val Phe Gly Cys Gly Thr Lys Leu Thr
                565                 570                 575

Val Leu Gly Gly Gly Gly Ser Gly Gly Gly Ser Gly Gly Gly Gly
                580                 585                 590

Ser Gly Gly Gly Ser Glu Val Gln Leu Leu Glu Ser Gly Gly Gly
            595                 600                 605

Leu Val Gln Pro Gly Gly Ser Leu Arg Leu Ser Cys Ala Ala Ser Gly
        610                 615                 620

Phe Thr Phe Ser Gly Tyr Asp Met Ser Trp Val Arg Gln Ala Pro Gly
625                 630                 635                 640

Lys Cys Leu Glu Trp Val Ser Val Ile Tyr Pro Asp Gly Asn Thr
                645                 650                 655

Tyr Tyr Ala Asp Ser Val Lys Gly Arg Phe Thr Ile Ser Arg Asp Asn
                660                 665                 670

Ser Lys Asn Thr Leu Tyr Leu Gln Met Asn Ser Leu Arg Ala Glu Asp
        675                 680                 685

Thr Ala Val Tyr Tyr Cys Ala Lys His Gly Gly Gln Lys Pro Thr Thr
        690                 695                 700

Lys Ser Ser Ser Ala Tyr Gly Met Asp Gly Trp Gly Gln Gly Thr Leu
705                 710                 715                 720

Val Thr Val Ser Ser
                725

<210> SEQ ID NO 83
<211> LENGTH: 719
<212> TYPE: PRT
<213> ORGANISM: Artificial Sequence
<220> FEATURE:
<223> OTHER INFORMATION: Synthetic_heavy chain of bispecific antibody
      (HER2(WT)x1A10 M12)

<400> SEQUENCE: 83

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Gly Ser Gly Ser Gly Ser Gly Ser Gly Ser Gly Ser Gly Ser
450                 455                 460

Gly Ser Gly Ser Gln Ser Val Leu Thr Gln Pro Pro Ser Ala Ser Gly
465                 470                 475                 480

Thr Pro Gly Gln Arg Val Thr Ile Ser Cys Ser Gly Ser Ser Ser Asn
                485                 490                 495

Ile Gly Asn Asn Tyr Val Thr Trp Tyr Gln Gln Leu Pro Gly Thr Ala
            500                 505                 510

Pro Lys Leu Leu Ile Tyr Ala Asp Ser His Arg Pro Ser Gly Val Pro
        515                 520                 525

Asp Arg Phe Ser Gly Ser Lys Ser Gly Thr Ser Ala Ser Leu Ala Ile
530                 535                 540

Ser Gly Leu Arg Ser Glu Asp Glu Ala Asp Tyr Tyr Cys Ala Thr Trp
```

```
545                 550                 555                 560
Asp Tyr Ser Leu Ser Gly Tyr Val Phe Gly Cys Gly Thr Lys Leu Thr
                565                 570                 575
Val Leu Gly Gly Gly Ser Gly Gly Gly Ser Gly Gly Gly Gly
            580                 585                 590
Ser Gly Gly Gly Ser Glu Val Gln Leu Leu Glu Ser Gly Gly
        595                 600                 605
Leu Val Gln Pro Gly Gly Ser Leu Arg Leu Ser Cys Ala Ala Ser Gly
    610                 615                 620
Phe Thr Phe Ser Ser Tyr Asp Met Ser Trp Val Arg Gln Ala Pro Gly
625                 630                 635                 640
Lys Cys Leu Glu Trp Val Ser Trp Ile Ser Tyr Ser Gly Gly Ser Ile
                645                 650                 655
Tyr Tyr Ala Asp Ser Val Lys Gly Arg Phe Thr Ile Ser Arg Asp Asn
                660                 665                 670
Ser Lys Asn Thr Leu Tyr Leu Gln Met Asn Ser Leu Arg Ala Glu Asp
                675                 680                 685
Thr Ala Val Tyr Tyr Cys Ala Arg Asp Ala Gln Arg Asn Ser Met Arg
    690                 695                 700
Glu Phe Asp Tyr Trp Gly Gln Gly Thr Leu Val Thr Val Ser Ser
705                 710                 715
```

```
<210> SEQ ID NO 84
<211> LENGTH: 725
<212> TYPE: PRT
<213> ORGANISM: Artificial Sequence
<220> FEATURE:
<223> OTHER INFORMATION: Synthetic_heavy chain of bispecific antibody
      (HER2(WT)x1A12)

<400> SEQUENCE: 84
```

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys Asp Thr
            20                  25                  30
Tyr Ile His Trp Val Arg Gln Ala Pro Gly Lys Gly Leu Glu Trp Val
        35                  40                  45
Ala Arg Ile Tyr Pro Thr Asn Gly Tyr Thr Arg Tyr Ala Asp Ser Val
    50                  55                  60
Lys Gly Arg Phe Thr Ile Ser Ala Asp Thr Ser Lys Asn Thr Ala Tyr
65                  70                  75                  80
Leu Gln Met Asn Ser Leu Arg Ala Glu Asp Thr Ala Val Tyr Tyr Cys
                85                  90                  95
Ser Arg Trp Gly Gly Asp Gly Phe Tyr Ala Met Asp Tyr Trp Gly Gln
            100                 105                 110
Gly Thr Leu Val Thr Val Ser Ser Ala Ser Thr Lys Gly Pro Ser Val
        115                 120                 125
Phe Pro Leu Ala Pro Ser Ser Lys Ser Thr Ser Gly Gly Thr Ala Ala
    130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205
Pro Ser Asn Thr Lys Val Asp Lys Lys Val Glu Pro Lys Ser Cys Asp
210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
            245                 250                 255
Ser Arg Thr Pro Glu Val Thr Cys Val Val Val Asp Val Ser His Glu
            260                 265                 270
Asp Pro Glu Val Lys Phe Asn Trp Tyr Val Asp Gly Val Glu Val His
            275                 280                 285
Asn Ala Lys Thr Lys Pro Arg Glu Glu Gln Tyr Asn Ser Thr Tyr Arg
290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
            325                 330                 335
Lys Thr Ile Ser Lys Ala Lys Gly Gln Pro Arg Glu Pro Gln Val Tyr
            340                 345                 350
Thr Leu Pro Pro Ser Arg Glu Glu Met Thr Lys Asn Gln Val Ser Leu
            355                 360                 365
Thr Cys Leu Val Lys Gly Phe Tyr Pro Ser Asp Ile Ala Val Glu Trp
            370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
            405                 410                 415
Lys Ser Arg Trp Gln Gln Gly Asn Val Phe Ser Cys Ser Val Met His
            420                 425                 430
Glu Ala Leu His Asn His Tyr Thr Gln Lys Ser Leu Ser Leu Ser Pro
            435                 440                 445
Gly Lys Gly Ser Gly Ser Gly Ser Gly Ser Gly Ser Gly Ser Gly Ser
450                 455                 460
Gly Ser Gly Ser Gln Ser Val Leu Thr Gln Pro Pro Ser Ala Ser Gly
465                 470                 475                 480
Thr Pro Gly Gln Arg Val Thr Ile Ser Cys Ser Gly Ser Ser Ser Asn
            485                 490                 495
Ile Gly Asn Asn Tyr Val Thr Trp Tyr Gln Gln Leu Pro Gly Thr Ala
            500                 505                 510
Pro Lys Leu Leu Ile Tyr Ala Asp Ser His Arg Pro Ser Gly Val Pro
            515                 520                 525
Asp Arg Phe Ser Gly Ser Lys Ser Gly Thr Ser Ala Ser Leu Ala Ile
            530                 535                 540
Ser Gly Leu Arg Ser Glu Asp Glu Ala Asp Tyr Tyr Cys Ala Thr Trp
545                 550                 555                 560
Asp Tyr Ser Leu Ser Gly Tyr Val Phe Gly Cys Gly Thr Lys Leu Thr
            565                 570                 575
Val Leu Gly Gly Gly Gly Ser Gly Gly Gly Ser Gly Gly Gly Gly Gly
            580                 585                 590
Ser Gly Gly Gly Gly Ser Glu Val Gln Leu Leu Glu Ser Gly Gly Gly
            595                 600                 605
Leu Val Gln Pro Gly Gly Ser Leu Arg Leu Ser Cys Ala Ala Ser Gly
```

```
                610              615              620
Phe Thr Phe Ser Gly Tyr Asp Met Ser Trp Val Arg Gln Ala Pro Gly
625                 630                 635                 640

Lys Cys Leu Glu Trp Val Ser Val Ile Tyr Pro Asp Gly Asn Thr
                645                 650                 655

Tyr Tyr Ala Asp Ser Val Lys Gly Arg Phe Thr Ile Ser Arg Asp Asn
                660                 665                 670

Ser Lys Asn Thr Leu Tyr Leu Gln Met Asn Ser Leu Arg Ala Glu Asp
            675                 680                 685

Thr Ala Val Tyr Tyr Cys Ala Lys His Gly Gly Gln Lys Pro Thr Thr
            690                 695                 700

Lys Ser Ser Ser Ala Tyr Gly Met Asp Gly Trp Gly Gln Gly Thr Leu
705                 710                 715                 720

Val Thr Val Ser Ser
                725

<210> SEQ ID NO 85
<211> LENGTH: 15
<212> TYPE: PRT
<213> ORGANISM: Artificial Sequence
<220> FEATURE:
<223> OTHER INFORMATION: Synthetic_peptide linker

<400> SEQUENCE: 85

Gly Gly Gly Gly Ser Gly Gly Gly Gly Ser Gly Gly Gly Gly Ser
1               5                   10                  15

<210> SEQ ID NO 86
<211> LENGTH: 18
<212> TYPE: PRT
<213> ORGANISM: Artificial Sequence
<220> FEATURE:
<223> OTHER INFORMATION: Synthetic_peptide linker

<400> SEQUENCE: 86

Gly Ser Gly Ser Gly Ser Gly Ser Gly Ser Gly Ser Gly Ser Gly Ser
1               5                   10                  15

Gly Ser

<210> SEQ ID NO 87
<211> LENGTH: 20
<212> TYPE: PRT
<213> ORGANISM: Artificial Sequence
<220> FEATURE:
<223> OTHER INFORMATION: Synthetic_peptide linker

<400> SEQUENCE: 87

Gly Gly Gly Gly Ser Gly Gly Gly Gly Ser Gly Gly Gly Gly Ser Gly
1               5                   10                  15

Gly Gly Gly Ser
                20

<210> SEQ ID NO 88
<211> LENGTH: 108
<212> TYPE: PRT
<213> ORGANISM: Artificial Sequence
<220> FEATURE:
<223> OTHER INFORMATION: Synthetic_light chain variable region of
      anti-4-1BB antibody (mutated AB41)

<400> SEQUENCE: 88

Asp Ile Val Met Thr Gln Ser Pro Ala Phe Leu Ser Val Thr Pro Gly
```

```
            1               5                  10                 15
Glu Lys Val Thr Ile Thr Cys Arg Ala Ser Gln Thr Ile Ser Asp Tyr
                20                  25                 30

Leu His Trp Tyr Gln Gln Lys Pro Asp Gln Ala Pro Lys Leu Leu Ile
                35                  40                 45

Lys Tyr Ala Ser Gln Ser Ile Ser Gly Ile Pro Ser Arg Phe Ser Gly
            50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Phe Pro Pro
                85                  90                  95

Thr Phe Gly Cys Gly Thr Lys Leu Glu Ile Lys Arg
                100                 105
```

<210> SEQ ID NO 89
<211> LENGTH: 255
<212> TYPE: PRT
<213> ORGANISM: Artificial Sequence
<220> FEATURE:
<223> OTHER INFORMATION: Synthetic_human 4-1BB (NP_001552.2)

<400> SEQUENCE: 89

```
Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly
                85                  90                  95

Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
        115                 120                 125

Lys Arg Gly Ile Cys Arg Pro Trp Thr Asn Cys Ser Leu Asp Gly Lys
        130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
                165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
        195                 200                 205

Arg Phe Ser Val Val Lys Arg Gly Arg Lys Lys Leu Leu Tyr Ile Phe
        210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
                245                 250                 255
```

ANTI-HER2/ANTI-4-1BB BISPECIFIC ANTIBODY AND USE THEREOF

CROSS-REFERENCE TO RELATED APPLICATIONS

This application claims the benefit of U.S. 62/878,951 filed on Jul. 26, 2019 and U.S. 63/024,608 filed on May 14, 2020, with the United States Patent and Trademark Office, the entire disclosure of which is herein incorporated by reference.

STATEMENT REGARDING JOINT RESEARCH AGREEMENT

The subject matter disclosed in U.S. application Ser. No. 17/296,752 was developed by and the claimed invention was made by, or on behalf of, one or more parties to a joint research agreement that was in effect on or before the effective filing date of the claimed invention. The claimed invention was made as a result of activities undertaken within the scope of the joint research agreement. The parties to the joint research agreement are: 1) Yuhan Corporation; and 2) ABL Bio Inc.

BACKGROUND OF THE INVENTION

1. Field

Provided are an anti-4-1BB/anti-HER2 bispecific antibody, and a pharmaceutical composition and a method for treating and/or preventing a cancer using the same.

2. Description of the Related Art 4-1 BB protein is a member of TNF-receptor superfamily (TNFRSF) and is a co-stimulatory molecule which is expressed following the activation of immune cells, both innate and adaptive immune cells. 4-1 BB plays important role in modulate the activity of various immune cells. 4-1BB agonists enhance proliferation and survival of immune cells, secretion of cytokines, and cytolytic activity CD8 T cells. Many other studies showed that activation of 4-1 BB enhances immune response to eliminate tumors in mice. Therefore, it suggests that 4-1 BB is a promising target molecule in cancer immunology. Despite of their anti-tumor efficacy, anti-4-1 BB antibody induced severe liver toxicity in clinical application.

HER2 protein is a member of epidermal growth factor receptor (EGFR) family and involved in various mechanisms related to tumors. HER2 is a typical receptor tyrosine kinase (RTK) present on the surface of cells, and thereby inducing proliferation and penetration of cancer cells, angiogenesis, etc.

Meanwhile, multispecific antibodies targeting two or more antigens have been developed in various kinds and forms and are expected as a new drug antibody having excellent therapeutic effects compared to a monoclonal antibody.

Therefore, there is a need to develop a multispecific antibody capable of recognizing two different antigens wherein one is present on a cancer cell and the other is present on other cell such as an immune cell, for more efficient cancer therapy.

SUMMARY OF THE INVENTION

One embodiment provides an anti-HER2/anti-4-1 BB bispecific antibody, comprising:
(1) an anti-HER2 antibody or an antigen-binding fragment thereof, as a HER2 targeting moiety, which is capable of specifically recognizing and/or binding to HER2 protein; and
(2) an anti-4-1 BB antibody or an antigen-binding fragment thereof, as a 4-1BB targeting moiety, which is capable of specifically recognizing and/or binding to 4-1 BB protein.

Another embodiment provides a pharmaceutical composition comprising the bispecific antibody. The pharmaceutical composition may further comprise a pharmaceutically acceptable carrier. The pharmaceutical composition may be used for treating and/or preventing a cancer and/or for enhancing immune response.

Another embodiment provides a pharmaceutical composition for treating and/or preventing a cancer and/or for enhancing immune response, the composition comprising the bispecific antibody.

Another embodiment provides a method of treating and/or preventing a cancer in a subject in need thereof, comprising administering to the subject a pharmaceutically effective amount of the bispecific antibody or the pharmaceutical composition to the subject. The method may further comprise a step of identifying the subject in need of treating and/or preventing a cancer, prior to the administering step.

Another embodiment provides a method of enhancing immune response in a subject in need thereof, comprising administering to the subject a pharmaceutically effective amount of the bispecific antibody or the pharmaceutical composition to the subject. The method may further comprise a step of identifying the subject in need of enhancing immune response, prior to the administering step.

Another embodiment provides a use of the bispecific antibody or the pharmaceutical composition in treating and/or preventing a cancer. Another embodiment provides a use of the bispecific antibody in preparing a medicament for treating and/or preventing a cancer.

Another embodiment provides a use of the bispecific antibody or the pharmaceutical composition in enhancing immune response. Another embodiment provides a use of the bispecific antibody in preparing a medicament for enhancing immune response.

An embodiment provides a polynucleotide encoding the bispecific antibody.

An embodiment provides a recombinant vector comprising the polynucleotide. The recombinant vector may be used as an expression vector of a polynucleotide encoding the bispecific antibody.

Another embodiment provides a cell comprising a polynucleotide encoding the bispecific antibody. The cell may be a recombinant cell transfected with a recombinant vector comprising the polynucleotide.

Another embodiment provides a method of preparing the bispecific antibody, comprising expressing the polynucleotide in a cell. The step of expressing the polynucleotide may be conducted by culturing the cell comprising the polynucleotide (for example, in a recombinant vector) under a condition allowing the expression of the polynucleotide.

BRIEF DESCRIPTION OF THE DRAWINGS

FIG. 1a is a graph showing antigen (human 4-1BB) binding activities of anti-4-1 BB antibodies measured by ELISA.

FIG. 1b is a graph showing cell binding activities of anti-4-1BB antibodies measured by ELISA.

FIG. 2a is a graph showing antigen (human HER2) binding activities of anti-HER2/anti-4-1 BB bispecific antibodies measured by ELISA.

FIG. 2b is a graph showing antigen (human HER2) binding activities of anti-HER2/anti-4-1 BB bispecific antibodies measured by ELISA.

FIG. 3a is a graph showing antigen (human 4-1 BB) binding activities of anti-HER2/anti-4-1 BB bispecific antibodies measured by ELISA.

FIG. 3b is a graph showing antigen (human 4-1 BB) binding activities of anti-HER2/anti-4-1 BB bispecific antibodies measured by ELISA.

FIG. 4a is a graph showing 4-1 BB signal activation level by anti-HER$^2$/anti-4-1 BB bispecific antibodies in NCI-N87 cell line (HER2 high expressing cells).

FIG. 4b is a graph showing 4-1 BB signal activation level by anti-HER2/anti-4-1 BB bispecific antibodies in MDA-MB-231 cell line (HER2 negative cells).

FIG. 5a is a graph showing 4-1BB signal activation level by an anti-HER2/anti-4-1 BB bispecific antibody in HER2-expressing NCI-N87 cell line.

FIG. 5b is a graph showing 4-1BB signal activation level by an anti-HER2/anti-4-1 BB bispecific antibody in HER2-expressing Calu-3 cell line.

FIG. 5c is a graph showing 4-1 BB signal activation level by an anti-HER2/anti-4-1 BB bispecific antibody in HER2-expressing HCC1954 cell line.

FIG. 5d is a graph showing 4-1BB signal activation level by an anti-HER2/anti-4-1 BB bispecific antibody in HER2-expressing JIMT1 cell line.

FIG. 5e is a graph showing 4-1BB signal activation level by an anti-HER2/anti-4-1 BB bispecific antibody in HER2-expressing ZR-75-1 cell line.

FIG. 5f is a graph showing 4-1 BB signal activation level by an anti-HER2/anti-4-1 BB bispecific antibody in HER2-non-expressing A431 cell line.

FIG. 5g is a graph showing 4-1BB signal activation level by an anti-HER2/anti-4-1 BB bispecific antibody in HER2-non-expressing MCF-7 cell line.

FIG. 5h is a graph showing 4-1BB signal activation level by an anti-HER2/anti-4-1 BB bispecific antibody in HER2-non-expressing MDA-MB231 cell line.

FIG. 5i is a graph showing 4-1 BB signal activation level by an anti-HER2/anti-4-1 BB bispecific antibody in HER2-non-expressing BxPC-3 cell line.

FIG. 6a is a graph showing 4-1 BB signal activation level by anti-HER$^2$/anti-4-1 BB bispecific antibodies in HER2-expressing Calu-3 cell line.

FIG. 6b is a graph showing 4-1 BB signal activation level by anti-HER$^2$/anti-4-1 BB bispecific antibodies in HER2-expressing HCC1954 cell line.

FIG. 7 is a graph showing correlation between the HER2 sABC and 4-1 BB-induced NF-kB signaling by an anti-HER2/anti-4-1 BB bispecific antibody in various cell lines.

FIGS. 8a-8d are graphs showing IFN-gamma level released from HER2-expressing HCC1954 cells treated with anti-HER2/anti-4-1 BB bispecific antibodies.

FIGS. 9a-9d are graphs showing % survival of HER2-expressing HCC1954 cells treated with anti-HER2/anti-4-1 BB bispecific antibodies.

FIG. 10 is a graph showing in vivo anti-tumor activities by anti-HER$^2$/anti-4-1 BB bispecific antibodies in HCC1954 bearing hPBMC engrafted mice.

FIG. 11 is a graph showing lymphocytes marker positive cell counts in HCC1954 bearing hPBMC engrafted mice treated with anti-HER2/anti-4-1 BB bispecific antibodies.

FIG. 12 is a graph showing in vivo anti-tumor activities by anti-HER$^2$/anti-4-1BB bispecific antibodies in human HER2/MC38 tumor bearing 4-1BB knock-in mice.

FIG. 13 is a graph showing in vivo anti-tumor activities by anti-HER$^2$/anti-4-1 BB bispecific antibodies in mice cured by anti-HER2/anti-4-1 BB bispecific antibody and re-challenged with human HER2/MC38 tumor cells and B16 F10 tumor cells.

FIG. 14 is a graph showing antibody-dependent cellular cytotoxicity (ADCC) effects of anti-HER2/anti-4-1 BB bispecific antibodies.

FIG. 15a is a graph showing results of FcγRIIb-dependent 4-1 BB bioassay for anti-HER2/anti-4-1 BB bispecific antibodies.

FIG. 15b is a graph showing results of FcγRIIb-independent 4-1BB bioassay for anti-HER2/anti-4-1 BB bispecific antibodies.

DETAILED DESCRIPTION OF THE INVENTION

The present disclosure relates to bispecific antibodies, each of which comprises an antibody specific to a tumor associated antigen (TAA; HER2) and an antibody specific to 4-1 BB, and uses thereof. These bispecific antibodies activate 4-1BB signaling and boost strong immune cell only in presence of HER2 expressing cells. Due to specific HER2-mediated immune response, it is expected to have much less liver toxicity by using bispecific antibodies compared to 4-1BB monoclonal antibody.

In the present disclosure, provided is an anti-HER2/anti-4-1BB bispecific antibody, and uses thereof, wherein the anti-HER2/anti-4-1 BB bispecific antibody may comprise:

(1) an anti-HER2 antibody or an antigen-binding fragment thereof, as a HER2 targeting moiety, which is capable of specifically recognizing and/or binding to HER2 protein, and (2) an anti-4-1 BB antibody or an antigen-binding fragment thereof, as a 4-1BB targeting moiety, which is capable of specifically recognizing and/or binding to 4-1 BB protein.

Hereinafter, the present invention is described in more detail.

Definition

As used herein, 'consisting of a sequence,' 'consisting essentially of a sequence,' or 'comprising a sequence' may refer to any case comprising the sequence, but it may not be intended to exclude a case comprising further sequence other than the sequence.

As used herein, the term 'a protein or polypeptide comprising or consisting of an amino acid sequence identified by SEQ ID NO' and 'a gene or polynucleotide comprising or consisting of a nucleic acid sequence identified by SEQ ID NO' may refer to a protein (or polypeptide) or gene (or polynucleotide), which consists essentially of the amino acid sequence or nucleic acid sequence, or which has at least 90%, at least 91%, at least 92%, at least 93%, at least 94%, at least 95%, at least 96%, at least 97%, at least 98%, or at least 99% sequence identity with the amino acid sequence or nucleic acid sequence with maintaining its inherent activity and/or function.

As used herein, the term "antibody" may encompass various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4), and light chains are classified as either kappa or lambda (κ, λ). It is the nature of this chain that determines the "class" of the antibody as IgG, IgM, IgA IgG, or IgE, respectively. The immunoglobulin subclasses (isotypes), e.g., IgG1, IgG2, IgG3, IgG4, IgG5, etc., are well characterized and are known to confer functional specialization.

An intact antibody includes two full-length light chains and two full-length heavy chains, in which each light chain is linked to a heavy chain by disulfide bonds. The antibody has a heavy chain constant region and a light chain constant region. The heavy chain constant region is of a gamma (γ), mu (μ), alpha (α), delta (δ), or epsilon (ε) type, which may be further categorized as gamma 1 (γ1), gamma 2(γ2), gamma 3(γ3), gamma 4(γ4), alpha 1(α1), or alpha 2(α2). The light chain constant region is of either a kappa (κ) or lambda (λ) type.

The term "heavy chain" refers to a full-length heavy chain or a fragment thereof, including a variable region $V_H$ that includes amino acid sequences sufficient to provide specificity to antigens, and three constant regions, $C_{H1}$, $C_{H2}$, and $C_{H3}$, and a hinge. The term "light chain" refers to a full-length light chain or a fragment thereof, including a variable region $V_L$ that includes amino acid sequences sufficient to provide specificity to antigens, and a constant region CL.

The term "complementarity determining region (CDR)" refers to an amino acid sequence found in a hyper variable region of a heavy chain or a light chain of immunoglobulin. The heavy and light chains may respectively include three CDRs (CDRH1, CDRH2, and CDRH3; and CDRL1, CDRL2, and CDRL3). The CDR may provide residues that play an important role in the binding of antibodies to an antigens or epitope. The terms "specifically binding" or "specifically recognized" is well known to one of ordinary skill in the art, and indicates that an antibody and an antigen specifically interact with each other to lead to an immunological activity.

In this disclosure, the antibody may include, but not be limited to, polyclonal or monoclonal; and/or human, humanized, animal (e.g., mouse, rabbit, etc.) derived antibody, or chimeric antibodies (e.g., mouse-human chimeric antibody).

An animal-derived antibody which is produced by immunizing an animal with a desired antigen may generally trigger an immune rejection response when administered to humans for treatment purpose, and a chimeric antibody has been developed to suppress such immune rejection response. A chimeric antibody is formed by replacing the constant region of an animal-derived antibody, which is a cause of anti-isotype response, with the constant region of a human antibody using genetic engineering methods. The chimeric antibody has considerably improved anti-isotype response in comparison with animal-derived antibodies, but animal-derived amino acids are still present in its variable regions and thus it still contains potential side effects resulting from an anti-idiotypic response. It is a humanized antibody that has been thus developed to improve such side effects. This is manufactured by grafting CDR (complementarity determining regions) which, of the variable regions of a chimeric antibody, has an important role in antigen binding into a human antibody framework.

As used herein, the term "antigen binding fragment" refers to a fragment derived from a full immunoglobulin structure including a portion capable of binding to an antigen such as CDRs. For example, the antigen binding fragment may be scFv, (scFv)$_2$, Fab, Fab', or F(ab')2, but not be limited thereto. In the present disclosure, the antigen binding fragment may be a fragment derived from an antibody, including at least one complementarity determining region, for example, selected from the group consisting of scFv, (scFv)$_2$, scFv-Fc, Fab, Fab' and F(ab')2.

Of the antigen binding fragments, Fab is a structure having variable regions of a light chain and a heavy chain, a constant region of the light chain, and the first constant region ($C_{H1}$) of the heavy chain, and it has one antigen binding site.

Fab' is different from Fab in that it has a hinge region including one or more cysteine residues at the C-terminal of heavy chain $C_{H1}$ domain. An F(ab')2 antibody is formed through disulfide bond of the cysteine residues at the hinge region of Fab'.

Fv is a minimal antibody piece having only a heavy chain variable region and light chain variable region, and a recombinant technique for producing the Fv fragment is well known in the pertinent art. Two-chain Fv may have a structure in which the heavy chain variable region is linked to the light chain variable region by a non-covalent bond, and single-chain Fv (scFv) may generally have a dimer structure as in the two-chain Fv in which the variable region of a heavy chain and the variable region of a light chain are covalently linked via a peptide linker or they are directly linked to each other at the C-terminal thereof.

The antigen binding fragments may be obtained using proteases (for example, a whole antibody is digested with papain to obtain Fab fragments, and is digested with pepsin to obtain F(ab')2 fragments), and may be prepared by a genetic recombinant technique.

Immunoglobulin (e.g., a human immunoglobulin) or antibody molecules of the disclosure can be of any type (e.g., IgG, IgE, IgM, IgD, IgA, IgY, etc.), class (e.g., IgG1, IgG2, IgG3, IgG4, IgG5, IgA1, IgA2, etc.), or subclass of immunoglobulin molecule.

In the antibody or antibody fragment, portions (e.g., constant regions) except the CDRs or variable regions may be derived from a human antibody and particularly, they may be derived from IgG, IgA, IgD, IgE, IgM, or IgY, for example, IgG1, IgG2, IgG 3, or IgG4.

The antibody or antigen binding fragment may be chemically or recombinantly synthesized (not naturally occurring).

4-1 BB Targeting Moiety

The anti-HER2/anti-4-1 BB bispecific antibody may comprise an anti-4-1 BB antibody or an antigen-binding fragment thereof, as a 4-1 BB targeting moiety.

The term "4-1BB", which is also called as CD137 or TNFRSF9 (TNF Receptor Superfamily Member 9), is a member of TNF-receptor superfamily (TNFRSF) and is a co-stimulatory molecule which is expressed following the activation of immune cells, both innate and adaptive immune cells. 4-1BB plays important role in modulate the activity of various immune cells. As used herein, 4-1 BB may be originated from a mammal, for example, Homo sapiens (human) (NCBI Accession No. NP_001552.2). For example, the human 4-1BB protein (NP_001552.2) may be represented by the amino acid sequence (SEQ ID NO: 89), as follows:

1 mgnscyniva tlllvlnfer trslqdpcsn cpagtfcdnn rnqicspcpp nsfssaggqr 61 tcdicrqckg vfrtrkecss tsnaecdctp gfhclgagcs mceqdckqgq eltkkgckdc 121 cfgtfndqkr gicrpwtncs ldgksvlvng tkerdvvcgp spadl-spgas svtppapare 181 pghspqiisf flaltstall fllffltlrf svvkrgrkkl lyifkqpfmr pvqttqeedg
241 cscrfpeeee ggcel In an embodiment, the anti-4-1 BB antibody or an antigen-binding fragment thereof may comprise:
- a CDR (complementarity determining region)-H1 (H-CDR1) comprising an amino acid sequence of SEQ ID NO: 1, 2, or 3;
- an H-CDR2 comprising an amino acid sequence of SEQ ID NO: 4, 5, or 6;
- an H-CDR3 comprising an amino acid sequence of SEQ ID NO: 7, 8, 9, 10, or 11;
- an L-CDR1 comprising an amino acid sequence of SEQ ID NO: 12 or 13;
- an L-CDR2 comprising an amino acid sequence of SEQ ID NO: 14 or 15; and
- an L-CDR3 comprising an amino acid sequence of SEQ ID NO: 16 or 17.

The amino acid sequences of the CDRs of the anti-4-1 BB antibody or an antigen-binding fragment are illustrated in Table 1:

TABLE 1

| SEQ ID NO | H-CDR1 | SEQ ID NO | H-CDR2 | SEQ ID NO | H-CDR3 |
|---|---|---|---|---|---|
| 1 | SYDMS | 4 | WISYSGGSIY YADSVKG | 7 | DGQRNSMREFDY |
|   |       |   |                     | 8 | DAQRNSMREFDY |
|   |       |   |                     | 9 | DAQRQSMREFDY |
| 2 | GYDMS | 5 | VIYPDDGNTY YADSVKG | 10 | HGGQKPTTKSSS AYGMDG |
| 3 | SYWMH | 6 | EINPGNGHTN YNEKFKS | 11 | SFTTARAFAY |

| SEQ ID NO | L-CDR1 | SEQ ID NO | L-CDR2 | SEQ ID NO | L-CDR3 |
|---|---|---|---|---|---|
| 12 | SGSSSNIGNNY VT | 14 | ADSHRPS | 16 | ATWDYSLSGYV |
| 13 | RASQTISDYLH | 15 | YASQSIS | 17 | QDGHSFPPT |

For example, the anti-4-1BB antibody or an antigen-binding fragment thereof may comprise:
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 7, an L-CDR1 comprising an amino acid sequence of SEQ ID NO: 12, an L-CDR2 comprising an amino acid sequence of SEQ ID NO: 14, and an L-CDR3 comprising an amino acid sequence of SEQ ID NO: 16;
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 8, an L-CDR1 comprising an amino acid sequence of SEQ ID NO: 12, an L-CDR2 comprising an amino acid sequence of SEQ ID NO: 14, and an L-CDR3 comprising an amino acid sequence of SEQ ID NO: 16;
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 9, an L-CDR1 comprising an amino acid sequence of SEQ ID NO: 12, an L-CDR2 comprising an amino acid sequence of SEQ ID NO: 14, and an L-CDR3 comprising an amino acid sequence of SEQ ID NO: 16;
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 7, an L-CDR1 comprising an amino acid sequence of SEQ ID NO: 13, an L-CDR2 comprising an amino acid sequence of SEQ ID NO: 15, and an L-CDR3 comprising an amino acid sequence of SEQ ID NO: 17;
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 8, an L-CDR1 comprising an amino acid sequence of SEQ ID NO: 13, an L-CDR2 comprising an amino acid sequence of SEQ ID NO: 15, and an L-CDR3 comprising an amino acid sequence of SEQ ID NO: 17;
- an H-CDR1 comprising an amino acid sequence of SEQ ID NO: 1, an H-CDR2 comprising an amino acid sequence of SEQ ID NO: 4, an H-CDR3 comprising an amino acid sequence of SEQ ID NO: 9, an L-CDR1 comprising an amino acid sequence of SEQ ID NO: 13, an L-CDR2 comprising an amino acid sequence of SEQ ID NO: 15, and an L-CDR3 comprising an amino acid sequence of SEQ ID NO: 17;
- an H-CDR1 comprising an amino acid sequence of SEQ ID NO: 2, an H-CDR2 comprising an amino acid sequence of SEQ ID NO: 5, an H-CDR3 comprising an amino acid sequence of SEQ ID NO: 10, an L-CDR1 comprising an amino acid sequence of SEQ ID NO: 12, an L-CDR2 comprising an amino acid sequence of SEQ ID NO: 14, and an L-CDR3 comprising an amino acid sequence of SEQ ID NO: 16;
- an H-CDR1 comprising an amino acid sequence of SEQ ID NO: 2, an H-CDR2 comprising an amino acid sequence of SEQ ID NO: 5, an H-CDR3 comprising an amino acid sequence of SEQ ID NO: 10, an L-CDR1 comprising an amino acid sequence of SEQ ID NO: 13, an L-CDR2 comprising an amino acid sequence of SEQ ID NO: 15, and an L-CDR3 comprising an amino acid sequence of SEQ ID NO: 17;
- an H-CDR1 comprising an amino acid sequence of SEQ ID NO: 3, an H-CDR2 comprising an amino acid sequence of SEQ ID NO: 6, an H-CDR3 comprising an amino acid sequence of SEQ ID NO: 11, an L-CDR1 comprising an amino acid sequence of SEQ ID NO: 12, an L-CDR2 comprising an amino acid sequence of SEQ ID NO: 14, and an L-CDR3 comprising an amino acid sequence of SEQ ID NO: 16; or
- an H-CDR1 comprising an amino acid sequence of SEQ ID NO: 3, an H-CDR2 comprising an amino acid sequence of SEQ ID NO: 6, an H-CDR3 comprising an amino acid sequence of SEQ ID NO: 11, an L-CDR1 comprising an amino acid sequence of SEQ ID NO: 13, an L-CDR2 comprising an amino acid sequence of SEQ ID NO: 15, and an L-CDR3 comprising an amino acid sequence of SEQ ID NO: 17.

In another embodiment, the anti-4-1 BB antibody or antigen-binding fragment thereof may comprise a heavy chain variable region comprising an H-CDR1 comprising an amino acid sequence of SEQ ID NO: 1, 2, or 3, an H-CDR2 comprising an amino acid sequence of SEQ ID NO: 4, 5, or 6, and an H-CDR3 comprising an amino acid sequence of SEQ ID NO: 7, 8, 9, 10, or 11; and a light chain variable region comprising an L-CDR1 comprising an amino acid sequence of SEQ ID NO: 12, or 13, an L-CDR2 comprising an amino acid sequence of SEQ ID NO: 14, or 15, and an L-CDR3 comprising an amino acid sequence of SEQ ID NO: 16, or 17.

In another embodiment, the anti-4-1BB antibody or antigen-binding fragment thereof may comprise a heavy chain variable region comprising an amino acid sequence of SEQ ID NO: 18, 19, 20, 21, 22, 23, 24, 25, 26, 27, 28, or 29; and a light chain variable region comprising or consisting essentially of an amino acid sequence of SEQ ID NO: 30, 31, 32, 33, 34, or 88.

The amino acid sequences of the variable regions of the anti-4-1 BB antibody or an antigen-binding fragment are illustrated in Table 2:

TABLE 2

| SEQ ID NO | Heavy chain variable region targeting 4-1BB |
|---|---|
| 18 | EVQLLESGGGLVQPGGSLRLSCAASGFTFSSYDMSWVRQAPGKGLE WVSWISYSGGSIYYADSVKGRFTISRDNSKNTLYLQMNSLRAEDTA VYYCARDGQRNSMREFDYWGQGTLVTVSS |
| 19 | EVQLLESGGGLVQPGGSLRLSCAASGFTFSSYDMSWVRQAPGKGLE WVSWISYSGGSIYYADSVKGRFTISRDNSKNTLYLQMNSLRAEDTA VYYCARDAQRNSMREFDYWGQGTLVTVSS |
| 20 | EVQLLESGGGLVQPGGSLRLSCAASGFTFSSYDMSWVRQAPGKGLE WVSWISYSGGSIYYADSVKGRFTISRDNSKNTLYLQMNSLRAEDTA VYYCARDAQRQSMREFDYWGQGTLVTVSS |
| 21 | EVQLLESGGGLVQPGGSLRLSCAASGFTFSGYDMSWVRQAPGKGLE WVSVIYPDDGNTYYADSVKGRFTISRDNSKNTLYLQMNSLRAEDAA VYYCAKHGGQKPTTKSSSAYGMDGWGQGTLVTVSS |
| 22 | EVQLLESGGGLVQPGGSLRLSCAASGFTFSGYDMSWVRQAPGKGLE WVSVIYPDDGNTYYADSVKGRFTISRDNSKNTLYLQMNSLRAEDTA VYYCAKHGGQKPTTKSSSAYGMDGWGQGTLVTVSS |
| 23 | QVQLQQSGAEVIKPGASVKLSCKASGYTFSSYWMHWVRQAPGQGLE WIGEINPGNGHTNYNEKFKSRATLTGDTSTSTVYMELSSLRSEDTA VYYCARSFTTARAFAYWGQGTLVTVSS |
| 24 | EVQLLESGGGLVQPGGSLRLSCAASGFTFSSYDMSWVRQAPGKCLE WVSWISYSGGSIYYADSVKGRFTISRDNSKNTLYLQMNSLRAEDTA VYYCARDGQRNSMREFDYWGQGTLVTVSS |
| 25 | EVQLLESGGGLVQPGGSLRLSCAASGFTFSSYDMSWVRQAPGKCLE WVSWISYSGGSIYYADSVKGRFTISRDNSKNTLYLQMNSLRAEDTA VYYCARDAQRNSMREFDYWGQGTLVTVSS |
| 26 | EVQLLESGGGLVQPGGSLRLSCAASGFTFSSYDMSWVRQAPGKCLE WVSWISYSGGSIYYADSVKGRFTISRDNSKNTLYLQMNSLRAEDTA VYYCARDAQRQSMREFDYWGQGTLVTVSS |
| 27 | EVQLLESGGGLVQPGGSLRLSCAASGFTFSGYDMSWVRQAPGKCLE WVSVIYPDDGNTYYADSVKGRFTISRDNSKNTLYLQMNSLRAEDAA VYYCAKHGGQKPTTKSSSAYGMDGWGQGTLVTVSS |
| 28 | EVQLLESGGGLVQPGGSLRLSCAASGFTFSGYDMSWVRQAPGKCLE WVSVIYPDDGNTYYADSVKGRFTISRDNSKNTLYLQMNSLRAEDTA VYYCAKHGGQKPTTKSSSAYGMDGWGQGTLVTVSS |
| 29 | QVQLQQSGAEVIKPGASVKLSCKASGYTFSSYWMHWVRQAPGQCLE WIGEINPGNGHTNYNEKFKSRATLTGDTSTSTVYMELSSLRSEDTA VYYCARSFTTARAFAYWGQGTLVTVSS |

| SEQ ID NO | Light chain variable region targeting 4-1BB |
|---|---|
| 30 | QSVLTQPPSASGTPGRRVTISCSGSSSNIGNNYVTWYQQLPGTAPK LLIYADSHRPSGVPDRFSGSKSGTSASLAISGLRSEDEADYYCATW DYSLSGYVFGGGTKLTVL |
| 31 | QSVLTQPPSASGTPGQRVTISCSGSSSNIGNNYVTWYQQLPGTAPK LLIYADSHRPSGVPDRFSGSKSGTSASLAISGLRSEDEADYYCATW DYSLSGYVFGGGTKLTVL |
| 32 | DIVMTQSPAFLSVTPGEKVTITCRASQTISDYLHWYQQKPDQAPKL LIKYASQSISGIPSRFSGSGSGTDFTFTISSLEAEDAATYYCQDGH SFPPTFGQGTKLEIKR |
| 33 | QSVLTQPPSASGTPGRRVTISCSGSSSNIGNNYVTWYQQLPGTAPK LLIYADSHRPSGVPDRFSGSKSGTSASLAISGLRSEDEADYYCATW DYSLSGYVFGCGTKLTVL |
| 34 | QSVLTQPPSASGTPGQRVTISCSGSSSNIGNNYVTWYQQLPGTAPK LLIYADSHRPSGVPDRFSGSKSGTSASLAISGLRSEDEADYYCATW DYSLSGYVFGCGTKLTVL |
| 88 | DIVMTQSPAFLSVTPGEKVTITCRASQTISDYLHWYQQKPDQAPKL LIKYASQSISGIPSRFSGSGSGTDFTFTISSLEAEDAATYYCQDGH SFPPTFGCGTKLEIKR |

For example, the anti-4-1BB antibody or an antigen-binding fragment thereof may comprise:
a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 30;
a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 31;
a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 32;
a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 33;
a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 34; or
a heavy chain variable region comprising an comprising an amino acid sequence of SEQ ID NO: 18, 19, 20, 21, 22, 23, 24, 25, 26, 27, 28, or 29, and a light chain variable region comprising an amino acid sequence of SEQ ID NO: 88.

The amino acid sequences of frameworks of the variable regions of the anti-4-1 BB antibody or an antigen-binding fragment are illustrated in Table 3:

TABLE 3

| SEQ ID NO | H-FR1 | SEQ ID NO | H-FR2 | SEQ ID NO | H-FR3 | SEQ ID NO | H-FR4 |
|---|---|---|---|---|---|---|---|
| 35 | EVQLLESGG GLVQPGGSL RLSCAASGF TFS | 37 | WVRQAP GKGLEWV S | 41 | RFTISRDNS KNTLYLQMN SLRAEDTAV YYCAR | 45 | WGQGT LVTVSS |
| 35 | EVQLLESGG GLVQPGGSL RLSCAASGF TFS | 37 | WVRQAP GKGLEWV S | 42 | RFTISRDNS KNTLYLQMN SLRAEDAAV YYCAK | 45 | WGQGT LVTVSS |

TABLE 3-continued

| | | | | | | | |
|---|---|---|---|---|---|---|---|
| 35 | EVQLLESGG GLVQPGGSL RLSCAASGF TFS | 37 | WVRQAP GKGLEWV S | 43 | RFTISRDNS KNTLYLQMN SLRAEDTAV YYCAK | 45 | WGQGT LVTVSS |
| 36 | QVQLQQSG AEVIKPGAS VKLSCKASG YTFS | 38 | WVRQAP GQGLEWI G | 44 | RATLTGDTS TSTVYMELS SLRSEDTAV YYCAR | 45 | WGQGT LVTVSS |
| 35 | EVQLLESGG GLVQPGGSL RLSCAASGF TFS | 39 | WVRQAP GKCLEWV S | 41 | RFTISRDNS KNTLYLQMN SLRAEDTAV YYCAR | 45 | WGQGT LVTVSS |
| 35 | EVQLLESGG GLVQPGGSL RLSCAASGF TFS | 39 | WVRQAP GKCLEWV S | 42 | RFTISRDNS KNTLYLQMN SLRAEDAAV YYCAK | 45 | WGQGT LVTVSS |
| 35 | EVQLLESGG GLVQPGGSL RLSCAASGF TFS | 39 | WVRQAP GKCLEWV S | 43 | RFTISRDNS KNTLYLQMN SLRAEDTAV YYCAK | 45 | WGQGT LVTVSS |
| 36 | QVQLQQSG AEVIKPGAS VKLSCKASG YTFS | 40 | WVRQAP GQCLEWI G | 44 | RATLTGDTS TSTVYMELS SLRSEDTAV YYCAR | 45 | WGQGT LVTVSS |

| SEQ ID NO | L-FR1 | SEQ ID NO | L-FR2 | SEQ ID NO | L-FR3 | SEQ ID NO | L-FR4 |
|---|---|---|---|---|---|---|---|
| 46 | QSVLTQPPS ASGTPGRR VTISC | 49 | WYQQLP GTAPKLLI Y | 51 | GVPDRFSG SKSGTSASL AISGLRSED EADYYC | 53 | FGGGT KLTVL |
| 47 | QSVLTQPPS ASGTPGQR VTISC | 49 | WYQQLP GTAPKLLI Y | 51 | GVPDRFSG SKSGTSASL AISGLRSED EADYYC | 53 | FGGGT KLTVL |
| 48 | DIVMTQSPA FLSVTPGEK VTITC | 50 | WYQQKP DQAPKLLI K | 52 | GIPSRFSGS GSGTDFTFT ISSLEAEDAA TYYC | 54 | FGQGT KLEIKR |
| 46 | QSVLTQPPS ASGTPGRR VTISC | 49 | WYQQLP GTAPKLLI Y | 51 | GVPDRFSG SKSGTSASL AISGLRSED EADYYC | 55 | FGCGT KLTVL |
| 47 | QSVLTQPPS ASGTPGQR VTISC | 49 | WYQQLP GTAPKLLI Y | 51 | GVPDRFSG SKSGTSASL AISGLRSED EADYYC | 55 | FGCGT KLTVL |

In another embodiment, the anti-4-1 BB antibody or antigen-binding fragment thereof may comprise a heavy chain comprising or consisting essentially of an amino acid sequence of SEQ ID NO: 56, 57, 58, 59, 60, or 61; and a light chain comprising or consisting essentially of an amino acid sequence of SEQ ID NO: 62, 63, or 64.

For example, the anti-4-1BB antibody or an antigen-binding fragment thereof may comprise:
a heavy chain comprising or consisting essentially of an amino acid sequence of SEQ ID NO: 56, 57, 58, 59, 60, or 61; and a light chain comprising or consisting essentially of an amino acid sequence of SEQ ID NO: 62;
a heavy chain comprising or consisting essentially of an amino acid sequence of SEQ ID NO: 56, 57, 58, 59, 60, or 61; and a light chain comprising or consisting essentially of an amino acid sequence of SEQ ID NO: 63; or
a heavy chain comprising or consisting essentially of an amino acid sequence of SEQ ID NO: 56, 57, 58, 59, 60, or 61; and a light chain comprising or consisting essentially of an amino acid sequence of SEQ ID NO: 64.

In another embodiment, the anti-4-1 BB antibody or antigen-binding fragment thereof may be a scFv (single chain variable fragment), comprising:
a heavy chain variable region comprising an H-CDR1 comprising an amino acid sequence of SEQ ID NO: 1, 2, or 3, an H-CDR2 comprising an amino acid sequence of SEQ ID NO: 4, 5, or 6, and an H-CDR3 comprising an amino acid sequence of SEQ ID NO: 7, 8, 9, 10, or 11; and
a light chain variable region comprising an L-CDR1 comprising an amino acid sequence of SEQ ID NO: 12, or 13, an L-CDR2 comprising an amino acid sequence of SEQ ID NO: 14, or 15, and an L-CDR3 comprising an amino acid sequence of SEQ ID NO: 16, or 17,
wherein the heavy chain variable region and the light chain variable region may be linked to each other in any order directly (i.e., without a linker) or via a peptide linker.

For example, the anti-4-1 BB scFv may comprise:
a heavy chain variable region comprising an amino acid sequence of SEQ ID NO: 18, 19, 20, 21, 22, 23, 24, 25, 26, 27, 28, or 29; and
a light chain variable region comprising or consisting essentially of an amino acid sequence of SEQ ID NO: 30, 31, 32, 33, 34, or 88,
wherein the heavy chain variable region and the light chain variable region may be linked to each other in any order directly or via a peptide linker.

For example, the anti-4-1 BB scFv may comprise:
a heavy chain variable region comprising or consisting essentially of an amino acid sequence of SEQ ID NO: 24, 25, 26, 27, 28, or 29; and a light chain variable region comprising or consisting essentially of an amino acid sequence of SEQ ID NO: 33;
a heavy chain variable region comprising or consisting essentially of an amino acid sequence of SEQ ID NO: 24, 25, 26, 27, 28, or 29; and a light chain variable region comprising or consisting essentially of an amino acid sequence of SEQ ID NO: 34; or
a heavy chain variable region comprising an comprising an amino acid sequence of SEQ ID NO: 24, 25, 26, 27, 28, or 29, and a light chain variable region comprising an amino acid sequence of SEQ ID NO: 88,
wherein the heavy chain variable region and the light chain variable region may be linked to each other in any order directly or via a peptide linker.

In the present disclosure, the anti-4-1BB scFv comprise a heavy chain variable region and a light chain variable region, in any order. For example, the anti-4-1BB scFv may comprise a light chain variable region and a heavy chain variable region, in a direction from N-terminus to C-terminus. Alternatively, the anti-4-1BB scFv may comprise a heavy chain variable region and a light chain variable region, in a direction from N-terminus to C-terminus.

HER2 Targeting Moiety

The anti-HER2/anti-4-1 BB bispecific antibody may comprise an anti-HER2 antibody or an antigen-binding fragment thereof as a HER2 targeting moiety.

The "HER2 (human epidermal growth factor receptor 2)" is encoded by ERBB2 gene, and is a member of the epidermal growth factor receptor (EGFR/ErbB). HER2 has been known to play an essential role in regulating cell proliferation and differentiation. Particularly, when bound to extracellular growth factors, it has a strong tendency of being assembled into homo- and/or heterodimers along with other HER receptors, which results in the activation of several forms of signal transduction pathway and induces apoptosis, survival, or cell proliferation. For instance, the HER2 protein may be polypeptides deposited under GenBank Accession Number NP_004439.2, NP_001005862.1, etc. which are encoded by the nucleotide sequences (mRNA) deposited under GenBank Accession Number NM_004448.4, NM_001005862.3, etc., respectively.

In one embodiment, the anti-HER2 antibody may be selected from the group consisting of Trastuzumab, Pertuzumab, and Trastuzumab emtansine (T-DM1).

The antigen binding region of the anti-HER2 antibody recognizing HER2 as an antigen may be scFv, (scFv)$_2$, Fab, Fab' or F(ab')2 of an anti-HER2 antibody selected from the group consisting of Trastuzumab, Pertuzumab, and Trastuzumab emtansine (T-DM1).

The anti-HER2 antibody or an antigen-binding fragment thereof may be an anti-HER2 antibody or an antigen-binding fragment thereof comprising 6 CDRs of Trastuzumab, Pertuzumab, or Trastuzumab emtansine (T-DM1).

In an embodiment, the anti-HER2 antibody or antigen-binding fragment thereof may be trastuzumab or an antigen-binding fragment thereof, or a variant thereof.

For example, the anti-HER2 antibody or antigen-binding fragment thereof may comprise:
an H-CDR1 comprising an amino acid sequence of SEQ ID NO: 65;
an H-CDR2 comprising an amino acid sequence of SEQ ID NO: 66;
an H-CDR3 comprising an amino acid sequence of SEQ ID NO: 67;
an L-CDR1 comprising an amino acid sequence of SEQ ID NO: 68;
an L-CDR2 comprising an amino acid sequence of SEQ ID NO: 69; and
an L-CDR3 comprising an amino acid sequence of SEQ ID NO: 70.

The amino acid sequences of the CDRs of the anti-HER2 antibody or an antigen-binding fragment are illustrated in Table 4:

TABLE 4

| SEQ ID NO | VH_CDR1 | SEQ ID NO | VH_CDR2 | SEQ ID NO | VH_CDR3 |
|---|---|---|---|---|---|
| 65 | DTYIH | 66 | RIYPTNGYTRYADSVKG | 67 | WGGDGFYAMDY |

| SEQ ID NO | L-CDR1 | SEQ ID NO | L-CDR2 | SEQ ID NO | L-CDR3 |
|---|---|---|---|---|---|
| 68 | RASQDVNTAVA | 69 | SASFLYS | 70 | QQHYTTPPT |

In another embodiment, the anti-HER2 antibody or antigen-binding fragment thereof may comprise a heavy chain variable region comprising an H-CDR1 comprising an amino acid sequence of SEQ ID NO: 65, an H-CDR2 comprising an amino acid sequence of SEQ ID NO: 66, and an H-CDR3 comprising an amino acid sequence of SEQ ID NO: 67; and a light chain variable region comprising an L-CDR1 comprising an amino acid sequence of SEQ ID NO: 68, an L-CDR2 comprising an amino acid sequence of SEQ ID NO: 69, and an L-CDR3 comprising an amino acid sequence of SEQ ID NO: 70.

In another embodiment, the anti-HER2 antibody or antigen-binding fragment thereof may comprise a heavy chain variable region comprising or consisting essentially of an amino acid sequence of SEQ ID NO: 71, and a light chain variable region comprising or consisting essentially of an amino acid sequence of SEQ ID NO: 72.

The amino acid sequences of the variable regions of the anti-HER2 antibody or an antigen-binding fragment are illustrated in Table 5:

TABLE 5

| SEQ ID NO | Heavy chain variable region targeting HER2 |
|---|---|
| 71 | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVS |

| SEQ ID NO | Light chain variable region targeting HER2 |
|---|---|
| 72 | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKR |

In another embodiment, the anti-HER2 antibody or antigen-binding fragment thereof may comprise a heavy chain comprising or consisting essentially of an amino acid sequence of SEQ ID NO: 73, or 74; and a light chain comprising or consisting essentially of an amino acid sequence of SEQ ID NO: 75.

In another embodiment, the anti-HER2 antibody or antigen-binding fragment thereof may be a scFv (single chain variable fragment), comprising:
a heavy chain variable region comprising an H-CDR1 comprising an amino acid sequence of SEQ ID NO: 65, an H-CDR2 comprising an amino acid sequence of SEQ ID NO: 66, and an H-CDR3 comprising an amino acid sequence of SEQ ID NO: 67; and
a light chain variable region comprising an L-CDR1 comprising an amino acid sequence of SEQ ID NO: 68, an L-CDR2 comprising an amino acid sequence of SEQ ID NO: 69, and an L-CDR3 comprising an amino acid sequence of SEQ ID NO: 70,
wherein the heavy chain variable region and the light chain variable region may be linked to each other in any order directly (i.e., without a linker) or via a peptide linker.

In another embodiment, the anti-HER2 antibody or antigen-binding fragment thereof may be a scFv (single chain variable fragment), comprising:
a heavy chain variable region comprising or consisting essentially of an amino acid sequence of SEQ ID NO: 71; and
a light chain variable region comprising or consisting essentially of an amino acid sequence of SEQ ID NO: 72,
wherein the heavy chain variable region and the light chain variable region may be linked to each other in any order directly or via a peptide linker.

In the present disclosure, the anti-HER2 scFv comprise a heavy chain variable region and a light chain variable region, in any order. For example, the anti-HER2 scFv may comprise a light chain variable region and a heavy chain variable region, in a direction from N-terminus to C-terminus. Alternatively, the anti-HER2 scFv may comprise a heavy chain variable region and a light chain variable region, in a direction from N-terminus to C-terminus.

Bispecific Antibody

The present disclosure provides an anti-HER2/anti-4-1 BB bispecific antibody comprising:

(1) an anti-HER2 antibody or an antigen-binding fragment thereof, as a HER2 targeting moiety, which is capable of specifically recognizing and/or binding to HER2 protein, and (2) an anti-4-1 BB antibody or an antigen-binding fragment thereof, as a 4-1 BB targeting moiety, which is capable of specifically recognizing and/or binding to 4-1 BB protein.

The anti-HER2/anti-4-1BB bispecific antibody may activate 4-1 BB signaling only when crosslinked by HER2-expressing tumor cells. In addition, the anti-4-1BB antibody or an antigen-binding fragment thereof contained in the bispecific antibody may be characterized by localizing and/or activating only in tumor microenvironment (TME), and/or considerably reducing liver toxicities compared to pre-existing anti-4-1 BB antibodies, with maintaining the efficacies of immune response enhancement and/or tumor treatment.

In an embodiment, the bispecific antibody may comprise a full-length anti-HER2 antibody and an antigen-binding fragment (e.g., scFv) of an anti-4-1BB antibody, wherein the antigen-binding fragment of an anti-4-1 BB antibody may be linked to N-terminus, C-terminus, or both thereof of a full-length anti-HER2 antibody, directly or via a peptide linker. In another embodiment, the bispecific antibody may comprise a full-length anti-4-1BB antibody and an antigen-binding fragment (e.g., scFv) of an anti-HER2 antibody, wherein the antigen-binding fragment of an anti-HER2 antibody may be linked to N-terminus, C-terminus, or both thereof of a full-length anti-4-1 BB antibody, directly or via a peptide linker.

In an embodiment, the scFv contained in the bispecific antibody may comprise a heavy chain variable region and a light chain variable region in any order. For example, the scFv contained in the bispecific antibody may comprise a light chain variable region and a heavy chain variable region, in a direction from N-terminus to C-terminus, and optionally a peptide linker therebetween, or alternatively, the scFv contained in the bispecific antibody may comprise a heavy chain variable region and a light chain variable region, in a direction from N-terminus to C-terminus, and optionally a peptide linker therebetween.

When the bispecific antibody comprises a full-length anti-HER2 antibody and an anti-4-1 BB scFv, the bispecific antibody may comprise:

(i) a first polypeptide comprising, in a direction from N-terminus to C-terminus:
a heavy chain of an anti-HER2 antibody,
optionally, a peptide linker (a first peptide linker), and
an anti-4-1 BB scFv; and
(ii) a second polypeptide comprising a light chain of the anti-HER2 antibody,
wherein the anti-4-1 BB scFv may comprise, in a direction from N-terminus to C-terminus:
a light chain variable region of an anti-4-1 BB antibody,
optionally, a peptide linker (a second peptide linker), and
a heavy chain variable region of the anti-4-1 BB antibody.
Alternatively, the bispecific antibody may comprise:
(i) a first polypeptide comprising, in a direction from N-terminus to C-terminus:
an anti-4-1 BB scFv,
optionally, a peptide linker (a first peptide linker), and
a heavy chain of an anti-HER2 antibody; and
(ii) a second polypeptide comprising a light chain of the anti-HER2 antibody,
wherein the anti-4-1 BB scFv may comprise, in a direction from N-terminus to C-terminus:
a light chain variable region of an anti-4-1 BB antibody,
optionally, a peptide linker (a second peptide linker), and
a heavy chain variable region of the anti-4-1 BB antibody.
Alternatively, the bispecific antibody may comprise:
(i) a first polypeptide comprising, in a direction from N-terminus to C-terminus:
a heavy chain of an anti-HER2 antibody,
optionally, a peptide linker (a first peptide linker), and
an anti-4-1 BB scFv; and
(ii) a second polypeptide comprising a light chain of the anti-HER2 antibody,
wherein the anti-4-1 BB scFv may comprise, in a direction from N-terminus to C-terminus:
a heavy chain variable region of the anti-4-1 BB antibody,
optionally, a peptide linker (a second peptide linker), and
a light chain variable region of an anti-4-1 BB antibody.
Alternatively, the bispecific antibody may comprise:
(i) a first polypeptide comprising, in a direction from N-terminus to C-terminus:
an anti-4-1 BB scFv,
optionally, a peptide linker (a first peptide linker), and
a heavy chain of an anti-HER2 antibody; and
(ii) a second polypeptide comprising a light chain of the anti-HER2 antibody,
wherein the anti-4-1 BB scFv may comprise, in a direction from N-terminus to C-terminus:
a heavy chain variable region of the anti-4-1 BB antibody,
optionally, a peptide linker (a second peptide linker), and
a light chain variable region of an anti-4-1 BB antibody.

When the bispecific antibody comprises a full-length anti-4-1 BB antibody and an anti-HER2 scFv, the bispecific antibody may comprise:
(i) a first polypeptide comprising, in a direction from N-terminus to C-terminus:
a heavy chain of an anti-4-1 BB antibody,
optionally, a peptide linker (a first peptide linker), and
an anti-HER2 scFv; and
(ii) a second polypeptide comprising a light chain of the anti-4-1 BB antibody,
wherein the anti-HER2 scFv may comprise, in a direction from N-terminus to C-terminus:
a light chain variable region of an anti-HER2 antibody,
optionally, a peptide linker (a second peptide linker), and
a heavy chain variable region of the anti-HER2 antibody.
Alternatively, the bispecific antibody may comprise:
(i) a first polypeptide comprising, in a direction from N-terminus to C-terminus:
an anti-HER2 scFv,
optionally, a peptide linker (a first peptide linker), and
a heavy chain of an anti-4-1 BB antibody; and
(ii) a second polypeptide comprising a light chain of the anti-4-1 BB antibody,
wherein the anti-HER2 scFv may comprise, in a direction from N-terminus to C-terminus:
a light chain variable region of an anti-HER2 antibody,
optionally, a peptide linker (a second peptide linker), and
a heavy chain variable region of the anti-HER2 antibody.
Alternatively, the bispecific antibody may comprise:
(i) a first polypeptide comprising, in a direction from N-terminus to C-terminus:
a heavy chain of an a anti-4-1 BB antibody,
optionally, a peptide linker (a first peptide linker), and
an anti-HER2 scFv; and
(ii) a second polypeptide comprising a light chain of the anti-4-1 BB antibody, wherein the anti-HER2 scFv may comprise, in a direction from N-terminus to C-terminus:
a heavy chain variable region of the anti-HER2 antibody, optionally, a peptide linker (a second peptide linker), and a light chain variable region of an anti-HER2 antibody.
Alternatively, the bispecific antibody may comprise:
(i) a first polypeptide comprising, in a direction from N-terminus to C-terminus:
an anti-HER2 scFv,
optionally, a peptide linker (a first peptide linker), and
a heavy chain of an anti-4-1 BB antibody; and
(ii) a second polypeptide comprising a light chain of the anti-4-1 BB antibody,
wherein the anti-HER2 scFv may comprise, in a direction from N-terminus to C-terminus:
a heavy chain variable region of the anti-HER2 antibody, optionally, a peptide linker (a second peptide linker), and a light chain variable region of an anti-HER2 antibody.

The first peptide linker and the second peptide linker may be, independently, present or absent in the bispecific antibody, and the same with or different from each other.

In another embodiment, both of the HER2 targeting moiety and the 4-1 BB targeting moiety contained in the bispecific antibody may be a full-length antibody or an antigen-binding fragment comprising heavy chain CDRs, light chain CDRs, or a combination thereof, which are linked to each other directly or via a peptide linker.

Given that each of antibodies can bind to both of 4-1BB (such as, human 4-1BB) and HER2 (such as, human HER2), the CDR sequences, or $V_H$ (heavy chain variable region) and $V_L$ (light chain variable region) sequences as disclosed herein can be "mixed and matched" to create other anti-HER2/anti-4-1 BB binding bispecific molecules.

Peptide Linker

For high purity of the antibody, the bispecific antibody may comprise a peptide linker between a heavy chain and scFv in a first polypeptide (a first peptide linker), and/or between heavy and light variable regions in scFv (a second peptide linker).

As used herein, the term "peptide linker" may refer to an oligopeptide including 1 to 100 amino acids, particularly 2 to 50 amino acids, each of which may be any kind of amino acids without any restrictions. Any conventional peptide linker may be used with or without an appropriate modification to comply with specific purposes. In a specific embodiment, the peptide linker may comprise, for example, Gly, Asn and/or Ser residues, and/or comprise neutral amino acids such as Thr and/or Ala. The amino acid sequences suitable for the peptide linker may be known in the relevant art. The length of the peptide linker can be properly determined within such a limit that the functions of the polypeptide and/or scFv will not be affected. For instance, the peptide linker may be formed by including a total of about 1 to about 100 amino acids, about 2 to about 50 amino acids, or about 5 to about 25 (e.g., 1, 2, 3, 4, 5, 6, 7, 8, 9, 10, 11, 12, 13, 14, 15, 16, 17, 18, 19, 20, 21, 22, 23, 24, or 25) amino acids, each of which is independently selected from the group consisting of Gly, Asn, Ser, Thr, and Ala. In one embodiment, the peptide linker may be represented as $(Gl_mS_l)_n$ (m, l, and n are the number of "G", "S", and "$(Gl_mS_l)$", respectively, and independently selected from integers of about 1 to about 10, particularly, 1, 2, 3, 4, 5, 6, 7, 8, 9, or 10). In one embodiment, the peptide linker can be amino acids of (GGGGS)2, (GGGGS)3, (GGGGS)4, or (GS)9, but not be limited thereto.

Medical Use

Provided is a medical use of the bispecific antibody for enhancing immune response, and/or treating and/or preventing a cancer.

More specifically, an embodiment provides a pharmaceutical composition comprising the bispecific antibody as an active ingredient. The pharmaceutical composition may further comprise a pharmaceutically acceptable carrier. The pharmaceutical composition may be used for enhancing immune response, and/or for treating and/or preventing a cancer.

Another embodiment provides a pharmaceutical composition for treating and/or preventing a cancer, the composition comprising the bispecific antibody as an active ingredient.

Another embodiment provides a method of treating and/or preventing a cancer in a subject in need thereof, comprising administering to the subject a pharmaceutically effective amount of the bispecific antibody or the pharmaceutical composition. The method may further step of identifying the subject in need of treating and/or preventing a cancer, prior to the administering step.

Another embodiment provides a use of the bispecific antibody or the pharmaceutical composition in treating and/or preventing a cancer. Another embodiment provides a use of the bispecific antibody in preparing a medicament for treating and/or preventing a cancer.

In some embodiment, the cancer may be characterized by HER2 expression or HER2 overexpression (compared to normal).

Another embodiment provides a pharmaceutical composition for enhancing immune response, the composition comprising the bispecific antibody as an active ingredient.

Another embodiment provides a method of enhancing immune response in a subject in need thereof, comprising administering to the subject a pharmaceutically effective amount of the bispecific antibody or the pharmaceutical composition to the subject. The method may further comprise a step of identifying the subject in need of enhancing immune response, prior to the administering step.

Another embodiment provides a use of the bispecific antibody or the pharmaceutical composition in enhancing immune response. Another embodiment provides a use of the bispecific antibody in preparing a medicament for enhancing immune response.

In some embodiment, the bispecific antibody or the pharmaceutical composition may enhance immune response with the proviso of the presence of HER2. For example, in the method of enhancing immune response, the subject may have a HER2-expressing or HER2-overexpressing cell (e.g., a HER2-expressing or HER2-overexpressing cancer cell).

The cancer to be prevented and/or treated by the bispecific antibody or the pharmaceutical composition may be associated with 4-1BB and/or HER2, especially, HER2-expressed or HER2-overexpressed cancer. The cancer may be selected from solid cancers and blood cancers. The cancer may be, but not limited to, one or more selected from the group consisting of breast cancer, colon cancer, gastric cancer, lung cancer (e.g., squamous cell carcinoma of the lung, small-cell lung cancer, non-small-cell lung cancer, adenocarcinoma of the lung), peritoneal carcinoma, skin cancer, squamous cell carcinoma, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, large intestine cancer, endometrial carcinoma or uterine carcinoma, salivary gland tumor, kidney cancer, cervix cancer, prostate cancer, vulvar cancer, thyroid cancer, head and neck cancer, brain cancer, biliary tract cancer, gallbladder cancer, and the like. The cancer may be a primary cancer or a metastatic cancer.

As used herein, the term "prevention and/or treatment of cancer" may refer to cancer cell death, inhibition of cancer cell proliferation, alleviation of symptoms associated with cancer, inhibition of metastasis of cancer, etc.

As used herein, the term "enhancement of immune response" may refer to 4-1 BB signal activation, enhancement in any immune response associated with 4-1BB, such as 4-1BB-induced signal activation (e.g., 4-1BB-induced NF-kB signal activation, increase in release of cytokine, target cell killing by immune cells, such as T cells, and the like, but not be limited thereto). In some embodiment, the enhancement of immune response by the bispecific antibody provided by this disclosure may occur be in the presence of HER2.

The pharmaceutical composition may further comprise a pharmaceutically acceptable carrier, diluent, and/or excipient, in addition to the bispecific antibody as an active ingredient. The pharmaceutically acceptable carrier, diluent, and/or excipient may be anyone selected from those commonly used for the formulation of antibodies. For example, the pharmaceutically acceptable carrier may be one or more selected from the group consisting of lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and mineral oil, but are not limited thereto.

The pharmaceutical composition may further comprise one or more selected from the group consisting of a lubricant, a wetting agent, a sweetener, a flavor enhancer, an emulsifying agent, a suspension agent, preservative, and the like.

The bispecific antibody or the pharmaceutical composition may be administered to the subject orally or parenterally. The parenteral administration may be intravenous injection, subcutaneous injection, muscular injection, intraperitoneal injection, endothelial administration, local administration, intranasal administration, intrapulmonary administration, or rectal administration. Since oral administration leads to digestion of proteins or peptides, an active ingredient in the compositions for oral administration must be coated or formulated to prevent digestion in stomach. In addition, the compositions may be administered using an optional device that enables the active ingredient to be delivered to target cells (e.g., cancer cells).

As used herein, the term "the pharmaceutically effective amount" may refer to an amount at which the active ingredient, bispecific antibody, can exert pharmaceutically meaningful effects in preventing or treating cancer. The pharmaceutically effective amount of the bispecific antibody, or a suitable dosage of the pharmaceutical composition indicated by an amount of the bispecific antibody, may be prescribed in a variety of ways, depending on various factors, such as age, body weight, gender, pathologic conditions, diets, excretion speed, and/or reaction sensitivity of a patient, formulation types, administration time, administration route, administration manner, and the like. For example, the pharmaceutically effective amount of the bispecific antibody, or a suitable dosage of the pharmaceutical composition, may be in the range from about 0.001 to about 1000 mg (amount of the bispecific antibody)/kg (body weight), about 0.01 to about 100 mg/kg, or 0.1 to 50 mg/kg per day for an adult.

The subject to which the bispecific antibody or the pharmaceutical composition is administered may be one selected from mammals, for example, humans, monkeys, rats, mice, dogs, cats, guinea pigs, rabbits, rats, mice, horses, cattle, cows, and so on, or a cell or tissue obtained therefrom, but are not limited thereto, and it may be one suffering from cancer.

The pharmaceutical composition may be formulated with a pharmaceutically acceptable carrier and/or excipient into a unit or a multiple dosage form by a method easily carried out by a skilled person in the pertinent art. The dosage form may be a solution in oil or an aqueous medium, a suspension, syrup, an emulsifying solution, an extract, powder, granules, a tablet, or a capsule, and may further include a dispersing or a stabilizing agent.

Polynucleotide, Recombinant Vector, and Preparation of Antibody

An embodiment provides a polynucleotide encoding the bispecific antibody. For example, the polypeptide may comprise a first polynucleotide encoding a heavy chain of an anti-Her2 antibody as described herein and a scFv of an anti-4-1 BB antibody as described herein, which are linked directly or via a peptide linker; and a second polynucleotide encoding a light chain of the anti-HER2 antibody. Alternatively, the polypeptide may comprise a first polynucleotide encoding a heavy chain of an anti-4-1 BB antibody as described herein and a scFv of an anti-HER2 antibody as described herein, which are linked directly or via a peptide linker; and a second polynucleotide encoding a light chain of the anti-4-1 BB antibody.

Another embodiment provides a recombinant vector comprising the polynucleotide. For example, the recombinant vector may comprise the first polynucleotide and the second polynucleotide together in one vector or separately in two vectors. Another embodiment provides a recombinant cell comprising the first polynucleotide and the second polynucleotide. For example, the recombinant cell may be a cell transfected with the recombinant vector.

Another embodiment provides a method of preparing the bispecific antibody, comprising expressing the polynucleotide, for example the first polynucleotide and the second polynucleotide, in a cell. The step of expressing the polynucleotide may be conducted by culturing the cell comprising the polynucleotide (for example, in a recombinant vector) under a condition allowing the expression of the polynucleotide. The method may further comprise isolating and/or purifying the anti-4-1 BB antibody or an antigen-binding fragment thereof from the cell culture, after the step of expressing or culturing.

The term "vector" refers to a means for expressing a target gene in a host cell, as exemplified by a plasmid vector, a cosmid vector, and a viral vector such as a bacteriophage vector, an adenovirus vector, a retrovirus vector, and an adeno-associated virus vector. The recombinant vector may be constructed from plasmids frequently used in the art (for example, pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19), phages (for example, Δgt4λB, λ-Charon, λΔz1, and M13) or by manipulating viruses (for example, SV40, etc.).

In the recombinant vector, the polynucleotide may be operatively linked to a promoter. The term "operatively linked" is intended to pertain to a functional linkage between a nucleotide sequence of interest and an expression regulatory sequence (for example, a promoter sequence). When being "operatively linked", the regulatory element can control the transcription and/or translation of the nucleotide of interest.

The recombinant vector may be constructed typically as a cloning vector or an expression vector. For recombinant expression vectors, a vector generally available in the relevant art for expressing a foreign protein in plant, animal, or microbial cells may be employed. Various methods well known in the art may be used for the construction of recombinant vectors.

For use in hosts, such as prokaryotic or eukaryotic cells, the recombinant vector may be constructed accordingly. For example, when a vector is constructed as an expression vector for use in a prokaryotic host, the vector typically includes a strong promoter for transcription (e.g., a pLκλ promoter, a CMV promoter, a trp promoter, a lac promoter, a tac promoter, a T7 promoter, etc.), a ribosomal binding site for initiating translation, and transcriptional/translational termination sequences. On the other hand, an expression vector for use in a eukaryotic host includes an origin of replication operable in a eukaryotic cell, such as an f1 origin of replication, an SV40 origin of replication, a pMB1 origin of replication, an adeno origin of replication, an AAV origin of replication, and a BBV origin of replication, but is not limited thereto. In addition, the expression vector typically includes a promoter derived from genomes of mammalian cells (for example, metallothionein promoter) or from mammalian viruses (for example, adenovirus late promoter, vaccinia virus 7.5K promoter, SV40 promoter, cytomegalovirus promoter, and tk promoter of HSV), and a polyadenylation sequence as a transcription termination sequence.

The recombinant cell may be prepared by introducing the recombinant vector into a suitable host cell. As long as it allows the sequential cloning and expression of the recombinant vector in a stable manner, any host cell known in the art may be employed in the present disclosure. Examples of the prokaryotic host cell available for the present disclosure may be selected from *E. coli, Bacillus* spp. such as *Bacillus subtilis* and *Bacillus thuringiensis*, and enterobacteriaceae strains such as *Salmonella typhimurium, Serratia marcescens* and various *Pseudomonas* species. Eukaryotic host cells that may be used for transformation may selected from, but are not limited to, *Saccharomyce cerevisiae*, insect cells, and animal cells, such as Sp2/0, CHO (Chinese hamster ovary) K1, CHO DG44, PER.C6, W138, BHK, COS-7, 293, HepG2, Huh7, 3T3, RIN, and MDCK.

The polynucleotide or a recombinant vector carrying the same may be introduced (transfected) into a host cell using a method well known in the relevant art. For example, this transfection may be carried out using a CaCl$_2$) or electroporation method when the host cell is prokaryotic. For eukaryotic host cells, the genetic introduction may be achieved using, but not limited to, microinjection, calcium phosphate precipitation, electroporation, liposome-mediated transfection, or particle bombardment.

To select a transformed host cell, advantage may be taken of a phenotype associated with a selection marker according to methods well known in the art. For example, when the selection marker is a gene conferring resistance to a certain antibiotic, the host cells may be grown in the presence of the antibiotic in a medium to select a transformant of interest.

Another embodiment provides a method for production of the bispecific antibody, the method comprising a step of expressing the polynucleotide or the recombinant vector in a host cell. In one embodiment, the production method may comprise culturing a recombinant cell harboring the polynucleotide or the recombinant vector thereat, and optionally isolating and/or purifying the antibody from the culture medium.

EXAMPLES

Hereafter, the present invention will be described in detail by examples.

The following examples are intended merely to illustrate the invention and are not construed to restrict the invention.

Example 1. Anti-4-1BB Antibodies 1.1 Preparation of Full Human Monoclonal Antibodies Against 4-1 BB Full human monoclonal anti-4-1 BB antibodies in a full-length IgG form were screened by phage library immunotube panning against 4-1 BB. For panning of the phage library (obtained from KBio Health and CUREBIO) against target molecules, four rounds of panning were carried out in total using 4-1 BB (NCBI Accession No. NP_001552.2) coated immunotubes.

Bacterial colonies from the 3 rounds of panning output were grown in SB-Carbenicillin (Biomatik cat #A2311-5g) in 96 deepwell plate until turbid, at which point $10^{11}$ pfu of VCSM13 helper phage (K-Bio Health) was added to each well. After 1 h infection at 37° C. with gentle shaking (80 rpm), 70 μg/mL of kanamycin was added and the cells were cultured overnight at 30° C. with shaking at 200 rpm.

Next day, the plates were centrifuged and the supernatants containing the phages were added to 4-1 BB antigen-coated ELISA plates blocked with 3% (v/v) BSA (bovine serum albumin) in PBST (Phosphate Buffered Saline with Tween 20). After 1 h incubation at room temperature, the plates were washed three times with PBST and anti M13 antibody (Sino Biological cat #11973-MM05) was added. The plates were incubated for 1 h, washed three times with PBST, and the binding activity was measured using tetramethylbenzidine (TMB).

The 4-1 BB specific binders were amplified for plasmid DNA sequencing. The light chain- and heavy chain-variable region (VL and VH) sequences were analyzed to identify unique sequences and determine sequence diversity, as shown in Tables 6 to 13 (Underline: CDR1, CDR2, and CDR3, in order). The anti-4-1BB antibody indicated as BMUR (BMS's Urelumab, U.S. Pat. No. 7,288,638) is used for comparing agonistic activity in following examples.

TABLE 6

| 1A10 | | |
|---|---|---|
| 1A10 | Amino acid sequence (N' → C') | |
| Heavy Chain | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDGQRNSMREFDYWGQGTLVTVSSASTK GPSVFPLAPCSRSTSESTAALGCLVKDYFPEPVTVSWNSGALT | |

TABLE 6-continued

1A10

| 1A10 | Amino acid sequence (N' → C') |
|---|---|
| | SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLGK (SEQ ID NO: 56) |
| Heavy Chain Variable Region (VH) | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDGQRNSMREFDYWGQGTLVTVSS (SEQ ID NO: 18) |
| H-CDR1 | SYDMS (SEQ ID NO: 1) |
| H-CDR2 | WISYSGGSIYYADSVKG (SEQ ID NO: 4) |
| H-CDR3 | DGQRNSMREFDY (SEQ ID NO: 7) |
| Light Chain | QSVLTQPPSASGTPGRRVTISCSGSSSNIGNNYVTWYQQLPG TAPKLLIYADSHRPSGVPDRFSGSKSGTSASLAISGLRSEDEAD YYCATWDYSLSGYVFGGGTKLTVLGQPKAAPSVTLFPPSSEEL QANKATLVCLISDFYPGAVTVAWKADSSPVKAGVETTTPSKQS NNKYAASSYLSLTPEQWKSHRSYSCQVTHEGSTVEKTVAPAE CS (SEQ ID NO: 62) |
| Light Chain Variable Region (VL) | QSVLTQPPSASGTPGRRVTISCSGSSSNIGNNYVTWYQQLPGT APKLLIYADSHRPSGVPDRFSGSKSGTSASLAISGLRSEDEADY YCATWDYSLSGYVFGGGTKLTVL (SEQ ID NO: 30) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 7

1A10 M4

| 1A10 M4 | Amino acid sequence (N' → C') |
|---|---|
| Heavy Chain | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRNSMREFDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLGK (SEQ ID NO: 57) |
| Heavy Chain Variable Region (VH) | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRNSMREFDYWGQGTLVTVSS (SEQ ID NO: 19) |
| H-CDR1 | SYDMS (SEQ ID NO: 1) |
| H-CDR2 | WISYSGGSIYYADSVKG (SEQ ID NO: 4) |
| H-CDR3 | DAQRNSMREFDY (SEQ ID NO: 8) |
| Light Chain | QSVLTQPPSASGTPGRRVTISCSGSSSNIGNNYVTWYQQLPGT APKLLIYADSHRPSGVPDRFSGSKSGTSASLAISGLRSEDEADY YCATWDYSLSGYVFGGGTKLTVLGQPKAAPSVTLFPPSSEELQ ANKATLVCLISDFYPGAVTVAWKADSSPVKAGVETTTPSKQSN NKYAASSYLSLTPEQWKSHRSYSCQVTHEGSTVEKTVAPAECS (SEQ ID NO: 62) |

TABLE 7-continued

1A10 M4

| 1A10 M4 | Amino acid sequence (N' → C') |
|---|---|
| Light Chain Variable Region (VL) | QSVLTQPPSASGTPGRRVTISCSGSSSNIGNNYVTWYQQLPGT APKLLIYADSHRPSGVPDRFSGSKSGTSASLAISGLRSEDEADY YCATWDYSLSGYVFGGGTKLTVL (SEQ ID NO: 30) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 8

1A10 M11

| 1A10 M11 | Amino acid sequence (N' → C') |
|---|---|
| Heavy Chain | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRQSMREFDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI SRTPEVTCVVVDVSQEDPEVQFNWYVDGVEVHNAKTKPREE QFNSTYRVVSVLTVLHQDWLNGKEYKCKVSNKGLPSSIEKTIS KAKGQPREPQVYTLPPSQEEMTKNQVSLTCLVKGFYPSDIAVE WESNGQPENNYKTTPPVLDSDGSFFLYSRLTVDKSRWQEGN VFSCSVMHEALHNHYTQKSLSLSLGK (SEQ ID NO: 58) |
| Heavy Chain Variable Region (VH) | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRQSMREFDYWGQGTLVTVSS (SEQ ID NO: 20) |
| H-CDR1 | SYDMS (SEQ ID NO: 1) |
| H-CDR2 | WISYSGGSIYYADSVKG (SEQ ID NO: 4) |
| H-CDR3 | DAQRQSMREFDY (SEQ ID NO: 9) |
| Light Chain | QSVLTQPPSASGTPGRRVTISCSGSSSNIGNNYVTWYQQLPGT APKLLIYADSHRPSGVPDRFSGSKSGTSASLAISGLRSEDEADY YCATWDYSLSGYVFGGGTKLTVLGQPKAAPSVTLFPPSSEELQ ANKATLVCLISDFYPGAVTVAWKADSSPVKAGVETTTPSKQSN NKYAASSYLSLTPEQWKSHRSYSCQVTHEGSTVEKTVAPAECS (SEQ ID NO: 62) |
| Light Chain Variable Region (VL) | QSVLTQPPSASGTPGRRVTISCSGSSSNIGNNYVTWYQQLPGT APKLLIYADSHRPSGVPDRFSGSKSGTSASLAISGLRSEDEADY YCATWDYSLSGYVFGGGTKLTVL (SEQ ID NO: 30) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 9

1A10 M12

| 1A10 M12 | Amino acid sequence (N' → C') |
|---|---|
| Heavy Chain | EVQLLESGGGLVQPGGSLRLSCAASGFTFSSYDMSWVRQAP GKGLEWVSWISYSGGSIYYADSVKGRFTISRDNSKNTLYLQMN SLRAEDTAVYYCARDAQRNSMREFDYWGQGTLVTVSSASTK GPSVFPLAPCSRSTSESTAALGCLVKDYFPEPVTVSWNSGALT SGVHTFPAVLQSSGLYSLSSVVTVPSSSLGTKTYTCNVDHKPS NTKVDKRVESKYGPPCPPCPAPEFLGGPSVFLFPPKPKDTLMI |

TABLE 9-continued

| 1A10 M12 | |
|---|---|
| 1A10 M12 | Amino acid sequence (N' → C') |
| | SRTPEVTCVVVDVSQEDPEVQFNWYVDGVEVHNAKTKPREE<br>QFNSTYRVVSVLTVLHQDWLNGKEYKCKVSNKGLPSSIEKTIS<br>KAKGQPREPQVYTLPPSQEEMTKNQVSLTCLVKGFYPSDIAVE<br>WESNGQPENNYKTTPPVLDSDGSFFLYSRLTVDKSRWQEGN<br>VFSCSVMHEALHNHYTQKSLSLSLGK (SEQ ID NO: 57) |
| Heavy Chain<br>Variable<br>Region (VH) | EVQLLESGGGLVQPGGSLRLSCAASGFTFSSYDMSWVRQAP<br>GKGLEWVSWISYSGGSIYYADSVKGRFTISRDNSKNTLYLQMN<br>SLRAEDTAVYYCARDAQRNSMREFDYWGQGTLVTVSS (SEQ<br>ID NO: 19) |
| H-CDR1 | SYDMS (SEQ ID NO: 1) |
| H-CDR2 | WISYSGGSIYYADSVKG (SEQ ID NO: 4) |
| H-CDR3 | DAQRNSMREFDY (SEQ ID NO: 8) |
| Light Chain | QSVLTQPPSASGTPGQRVTISCSGSSSNIGNNYVTWYQQLPGT<br>APKLLIYADSHRPSGVPDRFSGSKSGTSASLAISGLRSEDEADY<br>YCATWDYSLSGYVFGGGTKLTVLGQPKAAPSVTLFPPSSEELQ<br>ANKATLVCLISDFYPGAVTVAWKADSSPVKAGVETTTPSKQSN<br>NKYAASSYLSLTPEQWKSHRSYSCQVTHEGSTVEKTVAPAECS<br>(SEQ ID NO: 63) |
| Light Chain<br>Variable<br>Region (VL) | QSVLTQPPSASGTPGQRVTISCSGSSSNIGNNYVTWYQQLPG<br>TAPKLLIYADSHRPSGVPDRFSGSKSGTSASLAISGLRSEDEAD<br>YYCATWDYSLSGYVFGGGTKLTVL (SEQ ID NO: 31) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 10

| 1A10 M13 | |
|---|---|
| 1A10 M13 | Amino acid sequence (N' → C') |
| Heavy Chain | EVQLLESGGGLVQPGGSLRLSCAASGFTFSSYDMSWVRQAP<br>GKGLEWVSWISYSGGSIYYADSVKGRFTISRDNSKNTLYLQMN<br>SLRAEDTAVYYCARDAQRSMREFDYWGQGTLVTVSSASTK<br>GPSVFPLAPCSRSTSESTAALGCLVKDYFPEPVTVSWNSGALT<br>SGVHTFPAVLQSSGLYSLSSVVTVPSSSLGTKTYTCNVDHKPS<br>NTKVDKRVESKYGPPCPPCPAPEFLGGPSVFLFPPKPKDTLMI<br>SRTPEVTCVVVDVSQEDPEVQFNWYVDGVEVHNAKTKPREE<br>QFNSTYRVVSVLTVLHQDWLNGKEYKCKVSNKGLPSSIEKTIS<br>KAKGQPREPQVYTLPPSQEEMTKNQVSLTCLVKGFYPSDIAVE<br>WESNGQPENNYKTTPPVLDSDGSFFLYSRLTVDKSRWQEGN<br>VFSCSVMHEALHNHYTQKSLSLSLGK (SEQ ID NO: 58) |
| Heavy Chain<br>Variable<br>Region (VH) | EVQLLESGGGLVQPGGSLRLSCAASGFTFSSYDMSWVRQAP<br>GKGLEWVSWISYSGGSIYYADSVKGRFTISRDNSKNTLYLQMN<br>SLRAEDTAVYYCARDAQRSMREFDYWGQGTLVTVSS (SEQ<br>ID NO: 20) |
| H-CDR1 | SYDMS (SEQ ID NO: 1) |
| H-CDR2 | WISYSGGSIYYADSVKG (SEQ ID NO: 4) |
| H-CDR3 | DAQRSMREFDY (SEQ ID NO: 9) |
| Light Chain | QSVLTQPPSASGTPGQRVTISCSGSSSNIGNNYVTWYQQLPGT<br>APKLLIYADSHRPSGVPDRFSGSKSGTSASLAISGLRSEDEADY<br>YCATWDYSLSGYVFGGGTKLTVLGQPKAAPSVTLFPPSSEELQ<br>ANKATLVCLISDFYPGAVTVAWKADSSPVKAGVETTTPSKQSN<br>NKYAASSYLSLTPEQWKSHRSYSCQVTHEGSTVEKTVAPAECS<br>(SEQ ID NO: 63) |

TABLE 10-continued

1A10 M13

| 1A10 M13 | Amino acid sequence (N' → C') |
|---|---|
| Light Chain Variable Region (VL) | QSVLTQPPSASGTPGQRVTISCSGSSSNIGNNYVTWYQQLPG TAPKLLIYADSHRPSGVPDRFSGSKSGTSASLAISGLRSEDEAD YYCATWDYSLSGYVFGGGTKLTVL (SEQ ID NO: 31) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 11

1A12

| 1A12 | Amino acid sequence (N' → C') |
|---|---|
| Heavy Chain | EVQLLESGGGLVQPGGSLRLSCAASGFTFSGYDMSWVRQAP GKGLEWVSVIYPDDGNTYYADSVKGRFTISRDNSKNTLYLQMN SLRAEDAAVYYCAKHGGQKPTTKSSSAYGMDGWGQGTLVTV SSASTKGPSVFPLAPCSRSTSESTAALGCLVKDYFPEPVTVSW NSGALTSGVHTFPAVLQSSGLYSLSSVVTVPSSSLGTKTYTCN VDHKPSNTKVDKRVESKYGPPCPPCPAPEFLGGPSVFLFPPK PKDTLMISRTPEVTCVVVDVSQEDPEVQFNWYVDGVEVHNAK TKPREEQFNSTYRVVSVLTVLHQDWLNGKEYKCKVSNKGLPS SIEKTISKAKGQPREPQVYTLPPSQEEMTKNQVSLTCLVKGFY PSDIAVEWESNGQPENNYKTTPPVLDSDGSFFLYSRLTVDKSR WQEGNVFSCSVMHEALHNHYTQKSLSLSLGK (SEQ ID NO: 59) |
| Heavy Chain Variable Region (VH) | EVQLLESGGGLVQPGGSLRLSCAASGFTFSGYDMSWVRQAP GKGLEWVSVIYPDDGNTYYADSVKGRFTISRDNSKNTLYLQMN SLRAEDAAVYYCAKHGGQKPTTKSSSAYGMDGWGQGTLVTV SS (SEQ ID NO: 21) |
| H-CDR1 | GYDMS (SEQ ID NO: 2) |
| H-CDR2 | VIYPDDGNTYYADSVKG (SEQ ID NO: 5) |
| H-CDR3 | HGGQKPTTKSSSAYGMDG (SEQ ID NO: 10) |
| Light Chain | QSVLTQPPSASGTPGRRVTISCSGSSSNIGNNYVTWYQQLPGT APKLLIYADSHRPSGVPDRFSGSKSGTSASLAISGLRSEDEADY YCATWDYSLSGYVFGGGTKLTVLGQPKAAPSVTLFPPSSEELQ ANKATLVCLISDFYPGAVTVAWKADSSPVKAGVETTTPSKQSN NKYAASSYLSLTPEQWKSHRSYSCQVTHEGSTVEKTVAPAECS (SEQ ID NO: 62) |
| Light Chain Variable Region (VL) | QSVLTQPPSASGTPGRRVTISCSGSSSNIGNNYVTWYQQLPGT APKLLIYADSHRPSGVPDRFSGSKSGTSASLAISGLRSEDEADY YCATWDYSLSGYVFGGGTKLTVL (SEQ ID NO: 30) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 12

1A12 M1

| 1A12 M1 | Amino acid sequence (N' → C') |
|---|---|
| Heavy Chain | EVQLLESGGGLVQPGGSLRLSCAASGFTFSGYDMSWVRQAP GKGLEWVSVIYPDDGNTYYADSVKGRFTISRDNSKNTLYLQMN SLRAEDTAVYYCAKHGGQKPTTKSSSAYGMDGWGQGTLVTV SSASTKGPSVFPLAPCSRSTSESTAALGCLVKDYFPEPVTVSW |

TABLE 12-continued

1A12 M1

| | |
|---|---|
| 1A12 M1 | Amino acid sequence (N' → C') |
| | NSGALTSGVHTFPAVLQSSGLYSLSSVVTVPSSSLGTKTYTCN VDHKPSNTKVDKRVESKYGPPCPPCPAPEFLGGPSVFLFPPK PKDTLMISRTPEVTCVVVDVSQEDPEVQFNWYVDGVEVHNAK TKPREEQFNSTYRVVSVLTVLHQDWLNGKEYKCKVSNKGLPS SIEKTISKAKGQPREPQVYTLPPSQEEMTKNQVSLTCLVKGFY PSDIAVEWESNGQPENNYKTTPPVLDSDGSFFLYSRLTVDKSR WQEGNVFSCSVMHEALHNHYTQKSLSLSLGK (SEQ ID NO: 60) |
| Heavy Chain Variable Region (VH) | EVQLLESGGGLVQPGGSLRLSCAASGFTFSGYDMSWVRQAP GKGLEWVSVIYPDDGNTYYADSVKGRFTISRDNSKNTLYLQMN SLRAEDTAVYYCAKHGGQKPTTKSSSAYGMDGWGQGTLVTV SS (SEQ ID NO: 22) |
| H-CDR1 | GYDMS (SEQ ID NO: 2) |
| H-CDR2 | VIYPDDGNTYYADSVKG (SEQ ID NO: 5) |
| H-CDR3 | HGGQKPTTKSSSAYGMDG (SEQ ID NO: 10) |
| Light Chain | QSVLTQPPSASGTPGQRVTISCSGSSSNIGNNYVTWYQQLPGT APKLLIYADSHRPSGVPDRFSGSKSGTSASLAISGLRSEDEADY YCATWDYSLSGYVFGGGTKLTVLGQPKAAPSVTLFPPSSEELQ ANKATLVCLISDFYPGAVTVAWKADSSPVKAGVETTTPSKQSN NKYAASSYLSLTPEQWKSHRSYSCQVTHEGSTVEKTVAPAECS (SEQ ID NO: 63) |
| Light Chain Variable Region (VL) | QSVLTQPPSASGTPGQRVTISCSGSSSNIGNNYVTWYQQLPG TAPKLLIYADSHRPSGVPDRFSGSKSGTSASLAISGLRSEDEAD YYCATWDYSLSGYVFGGGTKLTVL (SEQ ID NO: 31) |
| L-CDR1 | SGSSSNIGNNYVT (SEQ ID NO: 12) |
| L-CDR2 | ADSHRPS (SEQ ID NO: 14) |
| L-CDR3 | ATWDYSLSGYV (SEQ ID NO: 16) |

TABLE 13

AB41

| | |
|---|---|
| AB41 | Amino acid sequence (N' → C') |
| Heavy Chain | QVQLQQSGAEVIKPGASVKLSCKASGYTFSSYWMHWVRQAP GQGLEWIGEINPGNGHTNYNEKFKSRATLTGDTSTSTVYMELS SLRSEDTAVYYCARSFTTARAFAYWGQGTLVTVSSASTKGPS VFPLAPCSRSTSESTAALGCLVKDYFPEPVTVSWNSGALTSGV HTFPAVLQSSGLYSLSSVVTVPSSSLGTKTYTCNVDHKPSNTK VDKRVESKYGPPCPPCPAPEFLGGPSVFLFPPKPKDTLMISRT PEVTCVVVDVSQEDPEVQFNWYVDGVEVHNAKTKPREEQFN STYRVVSVLTVLHQDWLNGKEYKCKVSNKGLPSSIEKTISKAK GQPREPQVYTLPPSQEEMTKNQVSLTCLVKGFYPSDIAVEWE SNGQPENNYKTTPPVLDSDGSFFLYSRLTVDKSRWQEGNVFS CSVMHEALHNHYTQKSLSLSLGK (SEQ ID NO: 61) |
| Heavy Chain Variable Region (VH) | QVQLQQSGAEVIKPGASVKLSCKASGYTFSSYWMHWVRQAP GQGLEWIGEINPGNGHTNYNEKFKSRATLTGDTSTSTVYMELS SLRSEDTAVYYCARSFTTARAFAYWGQGTLVTVSS (SEQ ID NO: 23) |
| H-CDR1 | SYWMH (SEQ ID NO: 3) |
| H-CDR2 | EINPGNGHTNYNEKFKS (SEQ ID NO: 6) |
| H-CDR3 | SFTTARAFAY (SEQ ID NO: 11) |

TABLE 13-continued

AB41

| AB41 | Amino acid sequence (N' → C') |
|---|---|
| Light Chain | DIVMTQSPAFLSVTPGEKVTITCRASQTISDYLHWYQQKPDQA PKLLIKYASQSISGIPSRFSGSGSGTDFTFTISSLEAEDAATYYC QDGHSFPPTFGQGTKLEIKRTVAAPSVFIFPPSDEQLKSGTASV VCLLNNFYPREAKVQWKVDNALQSGNSQESVTEQDSKDSTYS LSSTLTLSKADYEKHKVYACEVTHQGLSSPVTKSFNRGEC (SEQ ID NO: 64) |
| Light Chain Variable Region (VL) | DIVMTQSPAFLSVTPGEKVTITCRASQTISDYLHWYQQKPDQA PKLLIKYASQSISGIPSRFSGSGSGTDFTFTISSLEAEDAATYYC QDGHSFPPTFGQGTKLEIKR (SEQ ID NO: 32) |
| L-CDR1 | RASQTISDYLH (SEQ ID NO: 13) |
| L-CDR2 | YASQSIS (SEQ ID NO: 15) |
| L-CDR3 | QDGHSFPPT (SEQ ID NO: 17) |

1.2. Preparation of scFv Antibodies Against 4-1BB

Anti-4-1 BB scFv antibodies with a structure of (N')-VL-linker-VH-(C') were prepared using the variable regions of the full human monoclonal antibodies against 4-1BB shown in Tables 6 to 13 of Example 1.1, wherein the amino acid residue "G" at the position 44 of a heavy chain variable region was substituted with "C", and the amino acid residue "G" at the position 103 of a light chain variable region was substituted with "C". Such amino acid substitution from "G" to "C" in scFv can contribute to increase in stabilities of bispecific antibodies comprising the scFv as one target-specific moiety. The amino acid sequences of the prepared anti-4-1BB scFvs were illustrated in following Tables 14 to 19, while skilled persons in the art may apply changes or modifications of amino acid sequences in the following embodiments to meet specific purposes, including applying various types of peptide linkers such as (GGGGS)2, (GGGGS)3, (GGGGS)4, or (GS)9.

TABLE 14

1A10 (scFv)

| | Amino acid sequence (N' → C') |
|---|---|
| Light chain variable region (VL) | QSVLTQPPSASGTPGRRVTISCSGSSSNIGNNYVTWYQQLPG TAPKLLIYADSHRPSGVPDRFSGSKSGTSASLAISGLRSEDEA DYYCATWDYSLSGYVFGCGTKLTVL (SEQ ID NO: 33) |
| Linker | GGGGSGGGGSGGGGSGGGGS (SEQ ID NO: 87) |
| Heavy chain variable region (VH) | EVQLLESGGGLVQPGGSLRLSCAASGFTFSSYDMSWVRQAP GKCLEWVSWISYSGGSIYYADSVKGRFTISRDNSKNTLYLQMN SLRAEDTAVYYCARDGQRNSMREFDYWGQGTLVTVSS (SEQ ID NO: 24) |

TABLE 15

1A10 M4 (scFv)

| | Amino acid sequence (N'→C') |
|---|---|
| Light chain variable region (VL) | QSVLTQPPSASGTPGRRVTISCSGSSSNIGNNY VTWYQQLPGTAPKLLIYADSHRPSGVPDRFSGS KSGTSASLAISGLRSEDEADYYCATWDYSLSGY VFGCGTKLTVL (SEQ ID NO: 33) |
| Linker | GGGGSGGGGSGGGGSGGGGS (SEQ ID NO: 87) |
| Heavy chain variable region (VH) | EVQLLESGGGLVQPGGSLRLSCAASGFTFSSYD MSWVRQAPGKCLEWVSWISYSGGSIYYADSVKG RFTISRDNSKNTLYLQMNSLRAEDTAVYYCARD AQRNSMREFDYWGQGTLVTVSS (SEQ ID NO: 25) |

TABLE 16

1A10 M12 (scFv)

| | Amino acid sequence (N'→C') |
|---|---|
| Light chain variable region (VL) | QSVLTQPPSASGTPGQRVTISCSGSSSNIGNNYV TWYQQLPGTAPKLLIYADSHRPSGVPDRFSGSKS GTSASLAISGLRSEDEADYYCATWDYSLSGYVFG CGTKLTVL (SEQ ID NO: 34) |
| Linker | GGGGSGGGGSGGGGSGGGGS (SEQ ID NO: 87) |
| Heavy chain variable region (VH) | EVQLLESGGGLVQPGGSLRLSCAASGFTFSSYDM SWVRQAPGKCLEWVSWISYSGGSIYYADSVKGRF TISRDNSKNTLYLQMNSLRAEDTAVYYCARDAQR NSMREFDYWGQGTLVTVSS (SEQ ID NO: 25) |

TABLE 17

1A12 (scFv)

| | Amino acid sequence (N'→C') |
|---|---|
| Light chain variable region (VL) | QSVLTQPPSASGTPGRRVTISCSGSSSNIGNNYV TWYQQLPGTAPKLLIYADSHRPSGVPDRFSGSKS GTSASLAISGLRSEDEADYYCATWDYSLSGYVFG CGTKLTVL (SEQ ID NO: 33) |
| Linker | GGGGSGGGGSGGGGSGGGGS (SEQ ID NO: 87) |
| Heavy chain variable region (VH) | EVQLLESGGGLVQPGGSLRLSCAASGFTFSGYDM SWVRQAPGKCLEWVSVIYPDDGNTYYADSVKGRF TISRDNSKNTLYLQMNSLRAEDAAVYYCAKHGGQ KPTTKSSSAYGMDGWGQGTLVTVSS (SEQ ID NO: 27) |

TABLE 18

1A12 M1 (scFv)

| | Amino acid sequence (N'→C') |
|---|---|
| Light chain variable region (VL) | QSVLTQPPSASGTPGQRVTISCSGSSSNIGNNYV TWYQQLPGTAPKLLIYADSHRPSGVPDRFSGSKS GTSASLAISGLRSEDEADYYCATWDYSLSGYVFG CGTKLTVL (SEQ ID NO: 34) |
| Linker | GGGGSGGGGSGGGGSGGGGS (SEQ ID NO: 67) |
| Heavy chain variable region (VH) | EVQLLESGGGLVQPGGSLRLSCAASGFTFSGYDM SWVRQAPGKCLEWVSVIYPDDGNTYYADSVKGRF TISRDNSKNTLYLQMNSLRAEDTAVYYCAKHGGQ KPTTKSSSAYGMDGWGQGTLVTVSS (SEQ ID NO: 28) |

TABLE 19

AB41 (scFv)

| | Amino acid sequence (N'→C') |
|---|---|
| Light chain variable region (VL) | DIVMTQSPAFLSVTPGEKVTITCRASQTISDYLH WYQQKPDQAPKLLIKYASQSISGIPSRFSGSGSG TDFTFTISSLEAEDAATYYCQDGHSFPPTFGCGT KLEIKR (SEQ ID NO: 88) |
| Linker | GGGGSGGGGSGGGGSGGGGS (SEQ ID NO: 67) |
| Heavy chain variable region (VH) | QVQLQQSGAEVIKPGASVKLSCKASGYTFSSYWM HWVRQAPGQCLEWIGEINPGNGHTNYNEKFKSRA TLTGDTSTSTVYMELSSLRSEDTAVYYCARSFTT ARAFAYWGQGTLVTVSS (SEQ ID NO: 29) |

1.3. Antigen Binding Abilities of Anti-4-1BB Antibodies (Full-Length IgG Form) to Human 4-1BB (1) Antigen Binding Activity Measured by ELISA To evaluate the antigen binding activity, the antibody candidates prepared in Example 1.1 were subjected to ELISA test. Briefly, microtiter plates were coated with human 4-1BB-Fc protein (Sino Biological) at 0.1 µg/ml in PBS, 100 µl/well at 4° C. overnight, and then blocked with 100 µl/well of 5% (v/v) BSA. Five-fold dilutions of humanized antibodies (1A10, 1A12, and AB41) starting from 10 µg/ml were added to each well and incubated for 1-2 hours at room temperature (RT). The plates were washed with PBS/Tween and then incubated with goat-anti-human IgG antibody conjugated with Horse Radish Peroxidase (HRP) (Thermo) for 1 hour at RT. After washing, the plates were developed with TMB substrate and analyzed by spectrophotometer at OD 450-630 nm.

The obtained results are shown in FIG. 1a. As shown in FIG. 1a, all the anti-4-1 BB antibodies tested show 4-1 BB binding abilities.

(2) Cell Binding Activity Measured by FACS

To evaluate the cell binding activity, the antibody candidates were analyzed for its binding to mammalian expressed 4-1 BB by fluorescence-activated cell sorting (FACS). Briefly, GloResponse™ NFκ13-luc2/4-1BB Jurkat cell line (Promega; 3×10⁵ of cells), which are Jurkat cells expressing 4-1BB on their surface, were incubated with antibodies (1A10 and 1A12; each 10 ug/mL). After wash by FACS buffer (1% (v/v) BSA in PBS), the FITC-anti-human IgG antibody (Sigma, F9512, concentration: 2.0 mg/ml) was added to each well and incubated at 4° C. for 1 hour. The mean fluorescence intensity (MFI) of FITC was evaluated by FACSCalibur (BD Biosciences).

The obtained results are shown in FIG. 1b. As shown in FIG. 1b, all the anti-4-1 BB antibodies tested show binding abilities to 4-1 BB which expressed on cell surface and can efficiently bind to 4-1 BB expressed on mammalian cells.

Example 2. Preparation of Anti-HER2 Antibodies

As a HER2 targeting moiety for anti-HER2/Anti-4-1 BB bispecific antibodies, trastuzumab (Genentech; hereinafter indicated as "HER2(WT)", DrugBank Accession No. DB00072; human IgG1 Kappa monoclonal antibody), or its antigen-binding fragment, such as scFv, was employed.

The sequences of HER2(WT) were summarized in following Table 20.

The constant region of the anti-HER2 antibody contained in the bispecific antibody can be modified by introducing more than one mutation or change into human IgG1, one exemplary embodiment, HER2(NA or N297A) being presented in Table 20 below:

TABLE 20

| HER2(WT) | Sequence |
| --- | --- |
| Heavy Chain | EVQLVESGGGLVQPGGSLRLSCAASGFNIKDTYIHWVR QAPGKGLEWVARIYPTNGYTRYADSVKGRFTISADTSK NTAYLQMNSLRAEDTAVYYCSRWGGDGFYAMDYWGQGT LVTVSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVV VDVSHEDPEVKFNWYVDGVEVHNAKTKPREEQYNSTYR VVSVLTVLHQDWLNGKEYKCKVSNKALPAPIEKTISKA KGQPREPQVYTLPPSREEMTKNQVSLTCLVKGFYPSDI AVEWESNGQPENNYKTTPPVLDSDGSFFLYSKLTVDKS RWQQGNVFSCSVMHEALHNHYTQKSLSLSPGK (SEQ ID NO: 73) |
| Light Chain | DIQMTQSPSSLSASVGDRVTITCRASQDVNTAVAWYQQ KPGKAPKLLIYSASFLYSGVPSRFSGSRSGTDFTLTIS SLQPEDFATYYCQQHYTTPPTFGQGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 75) |
| HER2(NA) (N297A) | Sequence |
| Heavy Chain | EVQLVESGGGLVQPGGSLRLSCAASGFNIKDTYIHWVR QAPGKGLEWVARIYPTNGYTRYADSVKGRFTISADTSK NTAYLQMNSLRAEDTAVYYCSRWGGDGFYAMDYWGQGT LVTVSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVV VDVSHEDPEVKFNWYVDGVEVHNAKTKPREEQYASTYR VVSVLTVLHQDWLNGKEYKCKVSNKALPAPIEKTISKA KGQPREPQVYTLPPSREEMTKNQVSLTCLVKGFYPSDI AVEWESNGQPENNYKTTPPVLDSDGSFFLYSKLTVDKS RWQQGNVFSCSVMHEALHNHYTQKSLSLSPGK (SEQ ID NO: 74) |

TABLE 20-continued

| Light Chain | DIQMTQSPSSLSASVGDRVTITCRASQDVNTAVAWYQQ KPGKAPKLLIYSASFLYSGVPSRFSGSRSGTDFTLTIS SLQPEDFATYYCQQHYTTPPTFGQGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 75) |
| --- | --- |

Example 3. Preparation of Anti-HER2/Anti-4-1BB Bispecific Antibodies

Various anti-HER2/Anti-4-1 BB bispecific antibody candidates were prepared in full-length IgG (anti-HER2 antibody)-scFv(anti-4-1 BB antibody) format or in full-length IgG (anti-4-1 BB antibody)-scFv(anti-HER2 antibody) format: In this example, the anti-HER2 IgG and 4-1 BB scFv clones prepared in Example 2 and Example 1.2, respectively, were exemplarily selected, to prepare anti-HER2/anti-4-1 BB bispecific antibodies in a IgG-scFv fusion form (an scFv antibody fragment of one antigen is fused to c-terminal of IgG of another antigen). When HER2 is placed in full IgG part, IgG1 with ADCC reduced mutant backbone (N297A mutation; Cancer Cell, vol. 19, issue 1, pp. 101-113, etc.) was used, and when 4-1 BB is placed in full IgG part, IgG4 was used.

A DNA segment 1 having a nucleotide sequence encoding a heavy chain of an IgG antibody of the anti-HER2/anti-4-1 BB bispecific antibody was inserted into pcDNA 3.4 (Invitrogen, A14697; plasmid 1), and a DNA segment 2 having a nucleotide sequence encoding a light chain of an IgG antibody of the anti-HER2/anti-4-1 BB bispecific antibody was inserted into pcDNA 3.4 (Invitrogen, A14697; plasmid 2). Thereafter, a DNA segment 3 encoding a scFv was fused at a part of the DNA segment 1 corresponding to the c-terminus of the Fc region of the IgG antibody inserted into the plasmid 1, using a DNA segment 4 encoding a linker peptide having 15 amino acid lengths consisting of (GGGGS)3 or using a DNA segment 5 encoding a linker peptide having 18 amino acid lengths consisting of (GS)9, to construct vectors for the expression of bispecific antibodies. Furthermore, in order to stabilize scFv, as described in Example 1.2, additional modification was applied to generate disulfide bridge fusing VL103-VH44(VL103: VL having G→C mutation at the position 103; VH 44: VH having G→C mutation at the position 44) to C-terminus of light chain and C-terminus of heavy chain, respectively.

Among the prepared bispecific antibodies, sequences of the heavy chains, light chains, scFvs and DNA segments used in preparing several exemplary bispecific antibodies are illustrated in Tables 21 to 29. One or more than one point mutations in amino acid sequences can be applied in the antibodies presented below, for the purpose of improved stability and potency, decreased immunogenicity, and etc.

TABLE 21

| HER2 (NA) x1A10 bispecific antibody-1 | | |
| --- | --- | --- |
| | | Amino acid sequence (N'→C') |
| Heavy component | ① Heavy chain of anti-HER2 antibody | EVQLVESGGGLVQPGGSLRLSCAASGFNIKDTYIHWVR QAPGKGLEWVARIYPTNGYTRYADSVKGRFTISASTSK NTAYLQMNSLRAEDTAVYYCSRWGGDGFYAMDYWGQGT LVTVSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVV DVSHEDPEVKFNWYVDGVEVHNAKTKPREEQYASTYRV VSVLTVLHQDWLNGKEYKCKVNSKALPAPIEKTISKAK GQPREPQVYTLPPSREEMTKNQVSLTCLVKGFYPSDIA |

TABLE 21-continued

HER2 (NA)x1A10 bispecific antibody-1

Amino acid sequence (N'→C')

|  |  |  |  |
|---|---|---|---|
|  |  |  | VEWESNGQPENNYKTTPPVLDSDGSFFLYSKLTVDKSR<br>WQQGNVFSCSVMHEALHNHYTQKSLSLSPGK<br>(SEQ ID NO: 74) |
|  | ② Linker |  | GSGSGSGSGSGSGSGS<br>(SEQ ID NO: 86) |
|  | ③ scFv<br>of anti-<br>4-1BB<br>antibody | VL | QSVLTQPPSASGTPGRVVTISCSGSSSNIGNNYVTWYQ<br>QLPGTAPKLLIYADSHRPSGVPDRFSGSKSGTSASLAI<br>SGLRSEDEADYYCATWDYSLSGYVFGCGTKLTVL<br>(SEQ ID NO: 33) |
|  |  | Linker | GGGGSGGGGSGGGGSGGGGS<br>(SEQ ID NO: 87) |
|  |  | VH | EVQLLESGGGLVQPGGSLRLSCAASGFTFSSYDMSWVR<br>QAPGKCLEWVSWISYSGGSIYYADSVKGRFTISRDNSK<br>NTLYLQMNSLRAEDTAVYYCARDGQRNSMREFDYWGQG<br>TLVTVSS<br>(SEQ ID NO: 24) |
|  | Heavy<br>component<br>(① + ② + ③) |  | EVQLVESGGGLVQPGGSLRLSCAASGFNIKDTYIHWVR<br>QAPGKGLEWVARIYPTNGYTRYADSVKGRFTISADTSK<br>NTAYLQMNSLRAEDTAVYYCSRWGGDGFYAMDYWGQGT<br>LVTVSSASTKGPSVFPLAPSSKSTSGGTAALGCLVKDY<br>FPEPVTVSWNSGALTSGVHTFPAVLQSSLGYSLSSVVT<br>VPSSSLGTQTYICNVNHKPSNTKVDKKVEPKSCDKTHT<br>CPPCPAPELLGGPSVFLFPPKPKDTLMISRTPEVTCVV<br>VDVSHEDPEVKDNWYVDGVEVHNAKTKPREEQYASTYR<br>VVSVLTVLHQDWLNGKEYKCKVSNKALPAPIEKTISKA<br>KGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLSPGKGSGSGS<br>GSGSGSGSGSGSGSQSVLTQPPSASGTPGRRVTISCSGSS<br>SNIGNNYVTWYQQLPGTAPKLLIYADSHRPSGVPDRFS<br>GSKSGTSASLAISGLRSEDEADYYCATWDYSLSGYVFG<br>CGTKLTVLGGGGSGGGGSGGGGSGGGGSEVQLLESGGG<br>LVQPGGSLRLSCAASGFTFSSYDMSWVRQAPGKCLEWV<br>SWISYSGGSIYYADSVKGRFTISRDNSKNTLYLQMNSL<br>RAEDTAVYYCARDGQRNSMREFDYWGQGTLVTVSS<br>(SEQ ID NO: 77) |
| Light<br>component | Light chain of<br>anti-HER22<br>antibody |  | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQHYTTPPTFGQGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC<br>(SEQ ID NO: 75) |

TABLE 22

HER2 (NA)x1A10 bispecific antibody-2

Amino acid sequence (N'→C')

|  |  |  |  |
|---|---|---|---|
| Heavy<br>component | ① Heavy chain of<br>anti-HER2<br>antibody |  | EVQLVESGGGLVQPGGSLRLSCAASGFNIKDTYIHWVR<br>QAPGKGLEWVARIYPTNGYTRYADSVKGRFTISADTSK<br>NTAYLQMNSLRAEDTAVYYCSRWGGDGFYAMDYWGQGT<br>LVTVSSASTKGPSVFPLAPSSKSTSGGTAALGCLVKD<br>YFPEPVTVSWNSGALTSGVHTFPAVLQSSLGYSLSSVV<br>TVPSSSLGTQTYICNVNHKPSNTKVDKKVEPKSCDKTH<br>TCPPCPAPELLGGPSVFLFPPKPKDTLMISRTPEVTCV<br>VVDVSHEDPEVKFNWYVDGVEVHNAKTKPREEQYASTY<br>RVVSVLTVLHQDWLNGKEYKCKVSNKALPAPIEKTISK<br>AKGQPREPQVYTLPPSREEMTKNQVSLTCLVKGFYPSD<br>IAVEWESNGQPENNYKTTPPVLDSDGSFFLYSKLTVDK<br>SRWQQGNVFSCSVMHEALHNHYTQKSLSLSPGK<br>(SEQ ID NO: 74) |
|  | ② Linker |  | GSGSGSGSGSGSGSGS<br>(SEQ ID NO: 86) |
|  | ③ scFv<br>of anti-<br>4-1BB<br>antibody | VL | QSVLTQPSASGTPGRRVTISCSGSSSNIGNNYVTWYQQ<br>LPGTAPKLLIYADSHRPSGVPDRFSGSKSGTSASLAIS<br>GLRSEDEADYYCATWDYSLSGYVFGCGTKLTVL<br>(SEQ ID NO: 33) |
|  |  | Linker | GGGGSGGGGSGGGGSGGGGS<br>(SEQ ID NO: 87) |

TABLE 22-continued

HER2 (NA)x1A10 bispecific antibody-2

Amino acid sequence (N'→C')

| | | |
|---|---|---|
| | VH | EVQLLESGGGLVQPGGSLRLSCAASGFTFSSYDMSWVR<br>QAPGKCLEWVSWISYSGGSIYYADSVKGRFTISRDNSK<br>NTLYLQMNSLRAEDTAVYYCARDGQRNSMREFDYWGQG<br>TLVTVSS<br>(SEQ ID NO: 24) |
| | Heavy component<br>(① + ② + ③) | EVLQVESGGGLVQPGGSLRLSCAASGFNIKDTYIHWVR<br>QAPGKGLEWVARIYPTNGYTRYADSVKGRFTISADTSK<br>NTAYLQMNSLRAEDTAVYYCSRWGGDGFYAMDYWGQGT<br>LVTVSSASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVV<br>VDVSHEDPEVKFNWYVDGVEVHNAKTKPREEQYASTYR<br>VVSVLTVLHQDWLNGKEYKCKVSNKALPAPIEKTISKA<br>KGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLSPGKGSGSGS<br>GSGSGSGSGSGSGSQSVLTQPPSASGTPGRRVTISCSGSSS<br>NIGNNYVTWYQQLPGTAPKLLIYADSHRPSGVPDRFSG<br>SKSGTSASLAISGLRSEDEADYYCATWDYSLSGYVFGC<br>GTKLTVLGGGGSGGGGSGGGGSGGGGSEVQLLESGGGL<br>VQPGGSLRLSCAASGFTFSSYDMSWVRQAPGKCLEWVS<br>WISYSGGSIYYADSVKGRFTISRDNSKNTLYLQMNSLR<br>AEDTAVYYCARDGQRNSMREFDYWGQGTLVTVSS<br>(SEQ ID NO: 77) |
| Light<br>component | Light chain of<br>anti-HER2<br>antibody | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQHYTTPPTFGQGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC<br>(SEQ ID NO: 75) |

TABLE 23

HER2 (NA)x1A10 M4 bispecific antibody

Amino acid sequence (N'→C')

| | | |
|---|---|---|
| Heavy<br>component | ① Heavy chain<br>of anti-HER2<br>antibody | EVQLVESGGGLVQPGGSLRLSCAASGFNIKDTYIHWVR<br>QAPGKGLEWVARIYPTNGYTRYADSVKGRFTISADTSK<br>NTAYLQMNSLRAEDTAVYYCSRWGGDGFYAMDYWGQGT<br>LVTVSSASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVV<br>VDVSHEDPEVKFNWYVDGVEVHNAKTKPREEQYASTYR<br>VVSVLTVLHQDWLNGKEYKCKVSNKALPAPIEKTISKA<br>KGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLSPGK<br>(SEQ ID NO: 74) |
| | ② Linker | GSGSGSGSGSGSGSGSGS<br>(SEQ ID NO: 86) |
| | ③ scFv VL<br>of anti-<br>4-1BB<br>antibody | QSVLTQPPSASGTPGRRVTISCSGSSSNIGNNYVTWYQ<br>QLPGTAPKLLIYADSHRPSGVPDRFSGSKSGTSASLAI<br>SGLRSEDEADYYCATWDYSLSGYVFGCGTKLTVL<br>(SEQ ID NO: 33) |
| | VH | EVQLLESGGGLVQPGGSLRLSCAASGFTFSSYDMSWVR<br>QAPGKCLEWVSWISYSGGSIYYADSVKGRFTISRDNSK<br>NTLYLQMNSLRAEDTAVYYCARDAQRNSMREFDYWGQG<br>TLVTVSS<br>(SEQ ID NO: 25) |
| | Heavy component<br>(① + ② + ③) | EVQLVESGGGLVQPGGSLRLSCAASGFNIKDTYIHWVR<br>QAPGKGLEWVARIYPTNGYTRYADSVKGRFTISASTSK<br>NTAYLQMNSLRAEDTAVYYCSRWGGDGFYAMDYWGQGT<br>LVTVSSASTKGPSVFPLAPSSKSTSGGTAALGCLVKDY<br>FPEPVTVSWNSGALTSGVHTFPAVLQSSLGYSLSSVVT<br>VPSSSLGTQTYICNVNHKPSNTKVDKKVEPKSCDKTHT<br>CPPCPAPELLGGPSVFLFPPKPKDTLMISRTPEVTCVV<br>VDVSHEDPEVKFNWYVDGVEVHNAKTKPREEQYASTYR<br>VVSVLTVLHQDWLNGKEYKCKVSNKALPAPIEKTISKA |

TABLE 23-continued

HER2 (NA)x1A10 M4 bispecific antibody

Amino acid sequence (N'→C')

|  |  |  |
|---|---|---|
|  |  | KGQPREPQVYTLPPSREEMTKNQVSLTLVKGFYPSDIA VEWESNGQPENNYKTTPPVLDSDGSFFLYSKLTVDKSR WQQGNVFSCSVMHEALHNHYTQKSLSLSPGKGSGSGSG SGSGSGSGSGSQSVLTQPPSASGTPGRVVTISCSGSSS NIGNNYVTWYQQLPGTAPKLLIYADSHRPSGVPDWYQQ LPGTAPKLLIYADSHRPSGVPDRFSGSKSGTSASLAIS GLRSEDEADYYCATWDYSLSGYVFGCGTKLTVLGGGGS GGGGSGGGGSGGGGSEVQLLESGGGLVQPGGSLRLSCA ASGFTFSSYDMSWVRQAPGKCLEWVSWISYSGGSIYYA DSVKGRFTISRDNSKNTLYLQMNSLRAEDTAVYYCARD AQRNSMREFDYWGQGTLVTVSS (SEQ ID NO: 78) |
| Light component | Light chain of anti-HER2 antibody | DIQMTQSPSSLSASVGDRVTITCRASQDVNTAVAWYQQ KPGKAPKLLIYSASFLYSGVPSRFSGSRSGTDFTLTIS SLQPEDFATYYCQQHYTTPPTFGQGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 75) |

TABLE 24

HER2 (NA)x1A10 M12 bispecific antibody

Amino acid sequence (N'→C')

| | | | |
|---|---|---|---|
| Heavy component | ① Heavy chain of anti-HER2 antibody | | EVQLVESGGGLVQPGGSLRLSCAASGFNIKDTYIHWVR QAPGKGLEWVARIYPTNGYTRYADSVKRFTISADTSKN TAYLQMNSLRAEDTAVYYCSRWGGDGFYAMDYWGQGTL VTVSSASTKGPSVFPLAPSSKSTSGGTAALGCLVKDYF PEPVTVSWNSGALTSGVHTFPAVLQSSGLYSLSSVVTV PSSSLGTQTYICNVNHKPSNTKVDKKVEPKSCDKTHTC PPCPAPELLGGPSVFLFPPKPKDTLMISRTPEVTCVVV DVSHEDPEVKFNWYVDGVEVHNAKTKPREEQYASTYRV VSVLTVLHQDWLNGKEYKCKVSNKALPAPIEKTISKAK GQPREPQVYTLPPSREEMTKNQVSLTCLVKGFYPSDIA VEWESNGQPENNYKTTPPVLDSDGSFFLYSKLTVDKSR WQQGNVFSCSVMHEALHNHYTQKSLSLSPGK (SEQ ID NO: 74) |
| | ② Linker | | GSGSGSGSGSGSGSGSGS (SEQ ID NO: 86) |
| | ③ scFv of anti-4-1BB antibody | VL | QSVLTQPPSASGTPGQRVTISCSGSSSNIGNNYVTWYQ QLPGTAPKLLIYADSHRPSGVPDRSGSKSGTSASLAIS GLRSEDEADYYCATWDYSLSGYVFGCGTKLTVL (SEQ ID NO: 34) |
| | | Linker | GGGGSGGGGSGGGGSGGGGS (SEQ ID NO: 87) |
| | | VH | EVQLLESGGGLVQPGGSLRLSCAASGFTFSSYDMSWVR QAPGKCLEWVSWISYSGGSIYYADSVKGRFTISRDNSK NTLYLQMNSLRAEDTAVYYCARDAQRNSMREFDYWGQG TLVTVSS (SEQ ID NO: 25) |
| | Heavy component (①+②+③) | | EVQLVESGGGLVQPGGSLRLSCAASGFNIKDTYIHWVR QAPGKGLEWVARIYPTNGYTRYADSVKRFTISADTSK NTAYLQMNSLRAEDTAVYYCSRWGGDGFYAMDYWGQGT LVTVSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVV VDVSHEDPEVKFNWYVDGVEVHNAKTKPREEQYASTYR VVSVLTVLHQDWLNGKEYKCKVSNKALPAPIEKTISKA KGQPREPQVYTLPPSREEMTKNQVSLTCLVKGFYPSDI AVEWESNGQPENNYKTTPPVLDSDGSFFLYSKLTVDKS RWQQGNVFSCSVMHEALHNHYTQKSLSLSPGKGSGSGS GSGSGSGSGSGSQSVLTQPPSASGTPGQRVTISCSGSS SNIGNNYVTWYQQLPGTAPKLLIYADSHRPSGVPDRFS GSKSGTSASLAISGLRSEDEADYYCATWDYSLSGYVFG CGTKLTVLGGGGSGGGGSGGGGSGGGGSEVQLLESGGG LVQPGGSLRLSCAASGFTFSSYDMSWVRQAPGKCLEWV SWISYSGGSIYYADSVKGRFTISRDNSKNTLYLQMNSL RAEDTAVYYCARDAQRNSMREFDYWGQGTLVTVSS (SEQ ID NO: 79) |

TABLE 24-continued

HER2 (NA)x1A10 M12 bispecific antibody

Amino acid sequence (N'→C')

| | | |
|---|---|---|
| Light component | Light chain of anit-HER2 antibody | DIQMTQSPSSLSASVGDRVTITCRASQDVNTAVAWYQQ KPGKAPKLLIYSASFLYSGVPSRFSGSRSGTDFTLTIS SLPEDFATYYCQQHYTTPPTFGQGTKVEIKRTVAAPSV FIFPPSDEQLKSGTASVVCLLNNFYPREAKVQWKVDNA LQSGNSQESVTEQDSKDSTYSLSSTLTLSKADYEKHKV YACEVTHQGLSSPVTKSFNRGEC (SEQ ID NO: 75) |

TABLE 25

HER2 (NA)x1A12 bispecific antibody-1

Amino acid sequence (N'→C')

| | | | |
|---|---|---|---|
| Heavy component | ① Heavy chain of anti-HER2 antibody | | EVQLVESGGGLVQPGGSLRLSCAASGFNIKDTYIHWVR QAPGKGLEWVARIYPTNGYTRYADSVKGRFTISADTSK NTAYLQMNSLRAEDTAVYYCSRWGGDGFYAMDYWGQGT LVTVSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVV VDVSHEDPEVKFNWYVDGVEVHNAKTKPREEQYASTYR VVSVLTVLHQDWLNGKEYKCKVSNKALPAPIEKTISKA KGQPREPQVYTLPPSREEMTKNQVSLTCLVKGFYPSDI AVEWESNGQPENNYKTTPPVLDSDGSFFLYSKLTVDKS RWQQGNVFSCSVMHEALHNHYTQKSLSLSPGK (SEQ ID NO: 74) |
| | ② Linker | | GGGGSGGGGSGGGGS (SEQ ID NO: 85) |
| | ③ scFv of anti-4-1BB antibody | VL | QSVLTQPPSASGTPGRRVTISCSGSSSNIGNNYVTWYQ QLPGTAPKLLIYADSHRPSGVPDRFSGSKSGTSASLAI SGLRSEDEADYYCATWDYSLSGYVFGCGTKLTVL (SEQ ID NO: 33) |
| | | Linker | GGGGSGGGGSGGGGSGGGGS (SEQ ID NO: 87) |
| | | VH | EVQLLESGGGLVQPGGSLRLSCAASGFTFSGYDMSWVR QAPGKCLEWVSVIYPDDGNTYYADSVKGRFTISRDNSK NTLYLQMNSLRAEDAAVYYCAKHGGQKPTTKSSSAYGM DGWGQGTLVTVSS (SEQ ID NO: 27) |
| | Heavy component (① + ② + ③) | | EVQLVESGGGLVQPGGSLRLSCAASGFNIKDTYIHWVR QAPGKGLEWVARIYPTNGYTRYADSVKGRFTISADTSK NTAYLQMNSLRAEDTAVYYCSRWGGDGFYAMDYWGQGT LVTVSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVV VDVSHEDPEVKFNWYVDGVEVHNAKTKPREEQYASTYR VVSVLTVLHQDWLNGKEYKCKVSNKALPAPIEKTISKA KGQPREPQVYTLPPSREEMTKNQVSLTCLVKGFYPSDI AVEWESNGQPENNYKTTPPVLDSDGSFFLYSKLTVDKS RWQQGNVFSCSVMHEALHNHYTQKSLSLSPGKGGGGSG GGGSGGGGSQSVLTQPPSASGTPGRRVTISCSGSSSNI GNNYVTWYQQLPGTAPKLLIYADSHRPSGVPDRFSGSK SGTSASLAISGLRSEDEADYYCATWDYSLSGYVFGCGT KLTVLGGGGSGGGGSGGGGSGGGGSEVQLLESGGGLVQ PGGSLRLSCAASGFTFSGYDMSWVRQAPGKCLEWVSVI YPDDGNTYYADSVKGRFTISRDNSKNTLYLQMNSLRAE DAAVYYCAKHGGQKPTTKSSSAYGMDGWGQGTLVTVSS (SEQ ID NO: 80) |
| Light component | Light chain of anti-HER2 antibody | | DIQMTQSPSSLSASVGDRVTITCRASQDVNTAVAWYQQ KPGKAPKLLIYSASFLYSGVPSRFSGSRSGTDFTLTIS SQPEDFATYYCQQHYTTPPTFGQGTKVEIKRTVAAPSV FIFPPSDEQLKSGTASVVCLLNNFYPREAKVQWKVDNA LQSGNSQESVTEQDSKDSTYSLSSTLTLSKADYEKHKV YACEVTHQGLSSPVTKSFNRGEC (SEQ ID NO: 75) |

TABLE 26

HER2 (NA)×1A12 bispecific antibody-2

Amino acid sequence (N'→C')

| Heavy component | ① Heavy chain of anti-HER2 antibody | EVQLVESGGGLVQPGGSLRLSCAASGFNIKDTYIHWVR QAPGKGLEWVARIYPTNGYTRYADSVKGRFTISADTSK NTAYLQMNSLRAEDTAVYYCSRWGGDGFYAMDYWGQGT LVTVSSASTKGPSVFPLAPSSKSTSGGTAALGCLVKDY FPEPVTVSWNSGALTSGVHTFPAVLQSSLGYSLSSVVT VPSSSLGTQTYICNVNHKPSNTKVDKKVEPKSCDKTHT CPPCPAPELLGGPSVFLFPPKPKDTLMISRTPECTCVV VDVSHEDPEVKFNWYVDGVEVHNAKTKPREEQYASTYR VVSVLTVLHQDWLNGKEYKCKVSNKALPAPIEKTISKA KGQPREPQVYTLPPSREEMTKNQVSLTCLVKGFYPSDI AVEWESNGQPENNYKTTPPVLDSDGSFFLYSKLTVDKS RWQQGNVFSCSVMHEALHNHYTQKSLSLSPGK (SEQ ID NO: 74) |
|---|---|---|
| | ② Linker | GSGSGSGSGSGSGSGS (SEQ ID NO: 86) |
| | ③ scFv of anti-4-1BB antibody  VL | QSVLTQPPSASGTPGRRVTISCSGSSSNIGNNYVTWYQ QLPGTAPKLLIY<u>ADSHRPS</u>GVPRFSGSKSGTSASLAIS GLRSEDEADYYC<u>ATWDYSLSGYV</u>FGCGTKLTVL (SEQ ID NO: 33) |
| | Linker | GGGGSGGGGSGGGGSGGGGS (SEQ ID NO: 87) |
| | VH | EVQLLESGGGLVQPGGSLRLSCAASGFTFS<u>GYDMS</u>WVR QAPGKCLEWVS<u>VIYPDDGNTYYADSVKGRF</u>TISRDNSK NTLYLQMNSLRAEDAAVYYCAK<u>HGGQKPTTKSSSAYGM DG</u>WGQGTLVTVSS (SEQ ID NO: 27) |
| | Heavy component (①+②+③) | EVQLVESGGGLVQPGGSLRLSCAASGFNIKDTYIHWVR QAPGKGLEWVARIYPTNGYTRYADSVKGRFTISADTSK NTAYLQMNSLRAEDTAVYYCSRWGGDGFYAMDYWGQGT LVTVSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVV VDVSHEDPEVKFNWYVDGVEVHNAKTKPREEQYASTYR VVSVLTVLHQDWLNGKEYKCKVSNKALPAPIEKTISKA KGQPREPQVYTLPPSREEMTKNQVSLTCLVKGFYPSDI AVEWESNGQPENNYKTTPPVLDSDGSFFLYSKLTVDKS RWQQGNVFSCSVMHEALHNHYTQKSLSLSPGKGSGSGS GSGSGSGSGSGSQSVLTQPPSASGTPGRRVTISC<u>SGSS SNIGNNYVT</u>WYQQLPGTAPKLLIY<u>ADSHRPS</u>GVPDRFS GSKSGTSASLAISGLRSEDEADYYC<u>ATWDYSLSGYV</u>FG CGTKLTVLGGGGSGGGGSGGGGSGGGGSEVQLLESGGG LVQPGGSLRLSCAASGFTFS<u>GYDMS</u>WVRQAPGKCLEWV S<u>VIYPDDGNTYYADSVKGRF</u>TISRDNSKNTLYLQMNSL RAEDAAVYYCAK<u>HGGQKPTTKSSSAYGMDG</u>WGQGTLVT VSS (SEQ ID NO: 81) |
| Light component | Light chain of a anti-HER2 antibody | DIQMTQSPSSLSASVGDRVTITCRASQDVNTAVAWYQQ KPGKAPKLLIYSASFLYSGVPSRFSGSRSGTDFTLTIS SLQPEDFATYYCQQHYTTPPTFGQGTKVEIKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC (SEQ ID NO: 75) |

TABLE 27

HER2 (NA)×1A12 M1 bispecific antibody

Amino acid sequence (N'→C')

| Heavy component | ① Heavy chain of anti-HER2 antibody | EVLQVESGGGLVQPGGSLRLSCAASGFNIKDTYIHWVR QAPGKGLEWVARIYPTNGYTRYADSVKGRFTISADTSK NTAYLQMNSLRAEDTAVYYCSRWGGDGFYAMDYWGQGT LVTVSSASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSCDKTHT CPPCPAPELLGGPSVFLFPPKPKDTLMISRTPEVTCVV VDVSHEDPEVKFNWYVDGVEVHNAKTKPREEQYASTYR VVSVLTVLHQDWLNGKEYKCKVSNKALPAPIEKTISKA |
|---|---|---|

TABLE 27-continued

HER2 (NA)x1A12 M1 bispecific antibody

Amino acid sequence (N'→C')

| | | |
|---|---|---|
| | | KGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLSPGK<br>(SEQ ID NO: 74) |
| | ② Linker | GSGSGSGSGSGSGSGS<br>(SEQ ID NO: 86) |
| | ③ scFv of anti-4-1BB antibody | VL | QSVLTQPPSASGTPGQRVTISCSGSSSNIGNNYVTWYQ<br>QLPGTAPKLLIYADSHRPSGVPDRFSGSKSGTSASLAI<br>SGLRSEDEADYYCATWDYSLSGYVFGCGTKLTVL<br>(SEQ ID NO: 34) |
| | Linker | GGGGSGGGGSGGGGSGGGGS<br>(SEQ ID NO: 87) |
| | VH | EVQLLESGGGLVQPGGSLRLSCAASGFTFSGYDMSWVR<br>QAPGKCLEWVSVIYPDDGNTYYADSVKGRFTISRDNSK<br>NTLYLQMNSLRAEDTAVYYCAKHGGQKPTTKSSSAYGM<br>DGWGQGTLVTVSS<br>(SEQ ID NO: 28) |
| | Heavy component (① + ② + ③) | EVQLVESGGGLVQPGGSLRLSCAASGFNIKDTYIHWVR<br>QAPGKGLEWVARIYPTNGYTRYADSVKGRFTISADTSK<br>NTAYLQMNSLRAEDTAVYYCSRWGGDGFYAMDYWGQGT<br>LVTVSSASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVV<br>VDVSHEDPEVKFNWYVDGVEVHNAKTKPREEQYASTYR<br>VVSVLTVLHQDWLNGKEYKCKVSNKALPAPIEKTISKA<br>KGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLSPGKGSGSGS<br>GSGSGSGSGSGSGSQSVLTQPPSASGTPGQRVTISCSGSS<br>SNIGNNYVTWYQQLPGTAPKLLIYADSHRPSGVPDRFS<br>GSKSGTSASLAISGLRSEDEADYYCATWDYSLSGYVFG<br>CGTKLTVLGGGGSGGGGSGGGGSGGGGSEVQLLESGGG<br>LVQPGGSLRLSCAASGFTFSGYDMSWVRQAPGKCLEWV<br>SVIYPDDGNTYYADSVKGRFTISRDNSKNTLYLQMNSL<br>RAEDTAVYYCAKHGGQKPTTKSSSAYGMDGWGQGTLVT<br>VSS<br>(SEQ ID NO: 82) |
| Light component | Light chain of anti-HER2 antibody | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQHYTTPPTFGQGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC<br>(SEQ ID NO: 75) |

TABLE 28

HER2 (WT)x1A10 M12 bispecific antibody

Amino acid sequence (N'→C')

| | | |
|---|---|---|
| Heavy component | ① Heavy chain of anti-HER2 antibody | EVQLVESGGGLVQPGGSLRLSCAASGFNIKDTYIHWVR<br>QAPGKGLEWVARIYPTNGYTRYADSVKGRFTISADTSK<br>NTAYLQMNSLRAEDTAVYYCSRWGGDGFYAMDYWGQGT<br>LVTVSSASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVV<br>VDVSHEDPEVKFNWYVDGVEVHNAKTKPREEQYNSTYR<br>VVSVLTVLHQDWLNGKEYKCKVSNKALPAPIEKTISKA<br>KGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLSPGK<br>(SEQ ID NO: 73) |
| | ② Linker | GSGSGSGSGSGSGSGS<br>(SEQ ID NO: 86) |
| | ③ scFv of anti-4-1BB antibody | VL | QSVLTQPPSASGTPGQRVTISCSGSSSNIGNNYVTWYQ<br>QLPGTAPKLLIYADSHRPSGVPDRFSGSKSGTSASLAI<br>SGLRSEDEADYYCATWDYSLSGYVFGCGTKLTVL<br>(SEQ ID NO: 34) |

TABLE 28-continued

HER2 (WT)x1A10 M12 bispecific antibody

Amino acid sequence (N'→C')

| | | |
|---|---|---|
| | Linker | GGGGSGGGGSGGGGSGGGGS<br>(SEQ ID NO: 87) |
| | VH | EVQLLESGGGLVQPGGSLRLSCAASGFTFSSYDMSWVR<br>QAPGKCLEWVSWISYSGGSIYYADSVKGRFTISRDNSK<br>NTLYLQMNSLRAEDTAVYYCARDAQRNSMREFDYWGQG<br>TLVTVSS<br>(SEQ ID NO: 25) |
| | Heavy component<br>(① + ② + ③) | EVQLVESGGGLVQPGGSLRLSCAASGFNIKDTYIHWVR<br>QAPGKGLEWVARIYPTNGYTRYADSVKGRFTISADTSK<br>NTAYLQMNSLRAEDTAVYYCSRWGGDGFYAMDYWGQGT<br>LVTVSSASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVV<br>VDVSHEDPEVKFNWYVDGVEVHNAKTKPREEQYNSTYR<br>VVSVLTVLHQDWLNGKEYKCKVSNKALPAPIEKTISKA<br>KGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLSPGKGSGSGS<br>GSGSGSGSGSGSQSVLTQPPSASGTPGQRVTISCSGSS<br>SNIGNNYVTWYQQLPGTAPKLLIYADHSRPSGVPDRFS<br>GSKSGTSASLAISGLRSEDEADYYCATWDYSLSGYVFG<br>CGTKLTVLGGGGSGGGGSGGGGSGGGGSEVQLLESGGG<br>LVQPGGSLRLSCAASGFTFSSYDMSWVRQAPGKCLEWV<br>SWISYSGGSIYYADSVKGRFTISRDNSKNTLYLQMNSL<br>RAEDTAVYYCARDAQRNSMREFDYWGQGLTVTVSS<br>(SEQ ID NO: 83) |
| Light<br>component | Light chain of<br>anti-HER2<br>antibody | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQHYTTPPTFGQGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC<br>(SEQ ID NO: 75) |

TABLE 29

HER2 (WT)x1A12 M1 bispecific antibody

Amino acid sequence (N'→C')

| | | |
|---|---|---|
| Heavy<br>component | ① Heavy chain<br>of anti-HER2<br>antibody | EVQLVESGGGLVQPGGSLRLSCAASGFNIKDTYIHWVR<br>QAPGKGLEWVARIYPTNGYTRYADSVKGRFTISADTSK<br>NTAYLQMNSLRAEDTAVYYCSRWGGDGFYAMDYWGQGT<br>LVTVSSASTKGPSVFPLAPSSKSTSGGTAALGCLVKDY<br>FPEPVTVSWNSGALTSGVHTFPAVLQSSGLYSLSSVVT<br>VPSSSLGTQTYICNVNHKPSNTKVDKKVEPKSCDKTHT<br>CPPCPAPELLGGPSVFLFPPKPKDTLMISRTPEVTCVV<br>VDVSHEDPEVKFNWYVDGVEVHNAKTKPREEQYNSTYR<br>VVSVLTVLHQDWLNGKEYKCKVSNKALPAPIEKTISKA<br>KGQPREPQVYTLPPSREEMTKNQVSLTCLVKGFYPSDI<br>AVEWESNGQPENNYKTTPPVLDSDGSFFLYSKLTVDKS<br>RWQQGNVFSCSVMHEALHNHYTQKSLSLPGK<br>(SEQ ID NO: 73) |
| | ② Linker | GSGSGSGSGSGSGSGSGS<br>(SEQ ID NO: 86) |
| | ③ scFv VL<br>of anti-<br>4-1BB<br>antibody | QSVLTQPPSASGTPGQRVTISCSGSSSNIGNNYVTWYQ<br>QLPGTAPKLLIYADSHRPSGVPDRFSGSKSGTSASLAI<br>SGLRSEDEADYYCATWDYSLSGYVFGCGTKLTVL<br>(SEQ ID NO: 34) |
| | Linker | GGGGSGGGGSGGGGSGGGGS<br>(SEQ ID NO: 87) |
| | VH | EVQLLESGGGLVQPGGSLRLSCAASGFTFSGYDMSWVR<br>QAPGKCLEWVSVIYPDDGNTYYADSVKGRFTISRDNSK<br>NTLYLQMNSLRAEDTAVYYCAKHGGQKPTTKSSSAYGM<br>DGWGQGTLVTVSS<br>(SEQ ID NO: 28) |
| | Heavy component<br>(① + ② + ③) | EVQLVESGGGLVQPGGSLRLSCAASGFNIKDTYIHWVR<br>QAPGKGLEWVARIYPTNGYTRYADSVKGRFTISADTSK<br>NTAYLQMNSLRAEDTAVYYCSRWGGDGFYAMDYWGQGT<br>LVTVSSASTKGPSVFPLAPSSKSTSGGTAALGCLVKDY<br>FPEPVTVSWNSGALTSGVHTFPAVLQSSGLYSLSSVVT |

TABLE 29-continued

HER2 (WT)x1A12 M1 bispecific antibody

Amino acid sequence (N'→C')

|  |  |  |
|---|---|---|
|  |  | VPSSSLGTQTYICNVNHKPSNTKVDKKVEPKSCDKTHT<br>CPPCPAPELLGGPSVFLFPPKPKDTLMISRTPECTCVV<br>VDVSHEDPEVKFNWYVDGVEVHNAKTKPREEQYNSTYR<br>VVSVLTVLHQDWLNGKEYKCKVSNKALPAPIEKTISKA<br>KGQPREPQVYTLPPSREEMTKNQVSLTCLVKGFYPSDI<br>AVEWESNGQPENNKYTTPPVLDSDGSFFLYSKLTVDKS<br>RWQQGNVFSCSVMHEALHNHYTQKSLSLSPGKGSGSGS<br>GSGSGSGSGSGSQSVLTQPPSASGTPGQRVTISC<u>SGSS</u><br><u>SNIGNNYVTWYQQLPGTAPKLLIYADSHRPSGVPDRFS</u><br><u>GSKSGTSASLAISGLRSEDEADYYCATWDYSLSGYVFG</u><br>CGTKLTVLGGGGSGGGGSGGGGSGGGGSEVQLLESGGG<br>LVQPGGSLRLSCAASGFTFS<u>GYDMS</u>WVRQAPGKCLEWV<br>S<u>VIYPDDGNTYYADSVKG</u>RFTISRDNSKNTLYLQMNSL<br>RAEDTAVYYCAK<u>HGGQKPTTKSSSAYGMD</u>WGQGTLVT<br>VSS<br>(SEQ ID NO: 84) |
| Light<br>component | Light chain of<br>anti-HER2<br>antibody | DIQMTQSPSSLSASVGDRVTITCRASQDVNTAVAWYQQ<br>KPGKAPKLLIYSASFLYSGVPSRFSGSRSGTDFTLTIS<br>SLQPEDFATYYCQQHYTTPPTFGQGTKVEIKRTVAAPS<br>VFIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC<br>(SEQ ID NO: 75) |

Example 4. Test of Binding Affinity of Bispecific Antibodies (BsAbs)

4.1. Binding to Human HER2

The HER2 binding affinity of the bispecific antibodies were conducted by ELISA referring to Example 1.3(1). In brief, 96-well microtiter plates (Nunc-Immuno Plates, NUNC) were coated with human HER2-His protein (Sino Biological, 10004-H08H) at 1 µg/ml in PBS, 100 µl/well at 4° C. overnight, and then blocked with blocking buffer (200 µl/well of 1% (v/v) BSA (bovine serum albumin (Gibco, 30063572)) in PBS) for 2 hours at 37° C. Serial dilutions (starting from 0.1 µM) of anti-HER2/anti-4-1 BB bispecific antibodies prepared in Example 3 and anti-HER2 antibody (HER2(NA)) as a control were added to each well and incubated for 1 hour at 37° C. The plates were washed with PBS/0.05% Tween20 and incubated with HRP-conjugated Fab antibody (Pierce, 31414) for 1 hour at 37° C. After washing, the plates were developed with TMB (Tetramethylbenzidine, Sigma, T0440) substrate and analyzed by spectrophotometer at OD 450-650 nm.

The obtained results are shown in FIGS. 2a and 2b. As shown in FIGS. 2a and 2b, all the anti-HER2/anti-4-1BB bispecific antibodies tested can bind to human HER2 proteins with high affinity, which is similar to that of the control anti-HER2 antibody (NA).

4.2. Binding to Human 4-1BB

The 4-1 BB binding affinity of the bispecific antibodies were conducted by ELISA referring to Example 1.3(1). Briefly, 96-well microtiter plates (Nunc-Immuno Plates, NUNC) were coated with human 4-1BB-His protein (Sino Biological, 10041-H08H) at 1 µg/ml in PBS, 100 µl/well at 4° C. overnight, and then blocked with blocking buffer with blocking buffer (200 µl/well of 1% (v/v) BSA (bovine serum albumin (Gibco, 30063572)) in PBS) for 2 hours at 37° C. Serial dilutions (starting from 0.1 µM) of anti-HER2/anti-4-1 BB bispecific antibodies prepared in Example 3 and anti-HER2 antibody (HER2(NA)) as a control were added to each well and incubated for 1 hour at 37° C. The plates were washed with PBS/0.05% Tween20 and incubated with HRP-conjugated Fab antibody (Pierce, 31414) for 1 hour at 37° C. After washing, the plates were developed with TMB substrate and analyzed by spectrophotometer at OD 450-650 nm.

The obtained results are shown in FIGS. 3a and 3b. As shown in FIGS. 3a and 3b, all the anti-HER2/anti-4-1BB bispecific antibodies tested can bind to human 4-1 BB protein with high affinity, whereas the anti-HER2 antibody does not bind to human 4-1 BB protein.

The results of FIGS. 2a, 2b, 3a, and 3b are quantified and summarized in following Table 30:

TABLE 30

| EC50 (nM) | HER2 | 4-1BB |
|---|---|---|
| HER2(NA) | 0.134 | N/A |
| HER2(WT)x1A10 M12 | 0.159 | 0.027 |
| HER2(NA)x1A10 | 0.135 | 0.033 |
| HER2(NA)x1A10 M4 | 0.148 | 0.025 |
| HER2(NA)x1A10 M12 | 0.161 | 0.031 |
| HER2(WT)x1A12 M1 | 0.174 | 0.051 |
| HER2(NA)x1A12 | 0.148 | 0.043 |
| HER2(NA)x1A12 M1 | 0.143 | 0.048 |

As shown in Table 30, all the anti-HER2/anti-4-1 BB bispecific antibodies tested can bind to both human HER2 and human 4-1BB proteins with high affinities.

4.3. Binding to Various Cell Surface Expressed Human HER2

The binding affinities of the bispecific antibodies to various cells expressing HER2 on their surface were conducted by FACS analysis referring to Example 1.3(2).

Various tumor cell lines as listed in Table 31 were used. After disassociating each cell lines and washing in PBS, the number of cells was counted and set as $2 \times 10^5$ cells/100 µl FACS buffer, and then anti-HER2 antibody or anti-HER2/anti-4-1 BB bispecific antibodies were treated in 10 µg/mL, and they were reacted at 4° C. for 1 hour. After reaction, cells were washed in FACS buffer, and then the FITC labeled constant region (Fc)-specific antibody (Goat anti-human IgG FITC conjugate, Fc specific, Sigma, F9512, concentration: 2.0 mg/ml) was suspended in 2 μl/2×10$^5$ cells/100 μl FACS buffer, and it was reacted at 4° C. for 1 hour. After reaction, cells were washed in FACS buffer, it was analyzed using a FACSCalibur device. The negative control group was treated only with the FITC-labeled constant region (Fc)-specific antibody. To compare the expression degrees of HER2 among the cancer cell lines, the value of the result for the peak shift in the experimental group was divided by the result for the peak shift in the negative control group (Mean Fluorescence intensity Ratio=MFI Ratio: MFI of test antibody/MFI of 2nd Ab).

The obtained results are shown in following Table 31:

TABLE 31

| Cell line | | | MFI ratio | | |
|---|---|---|---|---|---|
| | | | anti-HER2 | HER2x1A10 | HER2x1A12 |
| NCI-N87 | Gastric | ATCC, CRL-5822 | 104 | 139 | 145 |
| BT-474 | Breast | ATCC, HTB-20 | 81 | 102 | 90 |
| Calu-3 | Lung | ATCC, HTB-55 | 74 | 82 | 82 |
| HCC1954 | Breast | ATCC, CRL-2338 | 32 | 40 | 42 |
| JIMT1 | Breast | DSMZ, ACC 589 | 26 | 27 | 25 |
| HT29 | Colon | ATCC, HTB-38 | 6.1 | 6.0 | 7.4 |
| MCF-7 | Breast | ATCC, HTB-22 | 5.2 | 4.9 | 5.8 |
| MDA-MB231 | Breast | ATCC, HTB-26 | 1.2 | 1.4 | 1.6 |
| H929 | MM | ATCC, CRL-9068 | 0.9 | 1.4 | 1.4 |
| Jurkat | ALL | ATCC, TIB-152 | 1.0 | 1.3 | 1.6 |

(MFI Ratio: MFI of 1$^{st}$ Ab/MFI of 2$^{nd}$ Ab)

As shown in Table 31, all the anti-HER2/anti-4-1 BB bispecific antibodies tested can bind to cell surface expressed human HER2 proteins.

Example 5. Binding Affinity of BsAbs to 4-1BB (SPR)

In the SPR experiment, the anti-HER2/anti-4-1 BB bispecific antibodies were individually captured on flow-cells 2, 3 and 4, keeping the flow-cell 1 as reference, on a Biocore® Series S Sensor Chip CM5 (GE Healthcare, BR100530) on which an anti-human Fab antibody (GE Healthcare, 28958325) had been immobilized by amine coupling. Recombinant Human 4-1BB protein (ACROBiosystems, 41B-H5227) was flowed across the chip at concentration of 400, 200, 100, 50, 25, 12.5, 6.25, 3.13, 1.56 and 0.78 nM at 30 μl/min for 300 seconds, followed by a dissociation phase of 400 seconds. Regeneration was performed with 10 mM Glycine-HCl (pH 2.0) (GE Healthcare, BR100355).

The obtained results are shown in following Table 32:

TABLE 32

| Antibody | KD (M) | kon(1/Ms) | kdis(1/s) |
|---|---|---|---|
| HER2(WT)x1A10 M12 | 2.11E−09 | 2.55E+05 | 5.38E−04 |
| HER2(NA)x1A10 M12 | 2.35E−09 | 2.69E+05 | 6.33E−04 |
| HER2(WT)x1A12 M1 | 1.24E−08 | 6.57E+04 | 8.11E−04 |
| HER2(NA)x1A12 M1 | 1.38E−08 | 6.74E+04 | 9.27E−04 |

As shown in Table 32, the anti-HER2/anti-4-1 BB bispecific antibodies tested show high 4-1 BB binding affinities.

Example 6. 4-1BB Signal Activation 6.1. BsAbs Vs. Monospecific Antibodies

In this example, for measuring 4-1BB signal activation, GloResponse™ NFκB-luc2/4-1 BB Jurkat cell line (Promega), genetically modified to stably express human 4-1 BB and luciferase downstream of a response element, was used as effector cell and cancer cells expressing or not expressing HER2 were used as target cells. In brief, as cancer cells, NCI-N87 (expressing HER2; 2.5×10$^4$ cells) or MDA-MB-231 (not expressing HER2; 2.5×10$^4$ cells) were plated in a 96-well assay plate and cultured overnight. On the day of assay, the anti-HER2/anti-4-1 BB bispecific antibodies (Example 3) to be tested and effector Jurkat cells (2.5×10$^4$ cells) were added to the plate. After 6 hrs incubation, Bio-Glo™ Reagent (Promega) was added and luminescence was measured using a microplate reader.

The obtained results are shown in following FIGS. 4a (NCI-N87 cell line) and 4b (MDA-MB-231 cell line). In FIGS. 4a and 4b, BMUR (BMS's Urelumab, U.S. Pat. No. 7,288,638) indicates an anti-4-1 BB antibody used for comparing agonistic activity. As shown in FIGS. 4a and 4b, anti-HER2/anti-4-1 BB bispecific antibodies lead to strong activation of 4-1BB signal only when co-cultured with HER2 high expressing cell. Fc crosslinked anti-4-1BB monoclonal antibodies showed minimal activity.

6.2. 4-1BB Activation in Various HER2-Expressing Cells (I)

In this example, for measuring 4-1BB signal activation, GloResponse™ NFκB-luc2/4-1 BB Jurkat cell line (Promega), genetically modified to stably express human 4-1 BB and luciferase downstream of a response element, was used as effector cell, and cancer cells expressing or not expressing HER2 were used as target cells. In brief, HER2-expressing (NCI-N87, Calu-3, HCC1954, JIMT1, ZR-75-1) or HER2-non-expressing (MDA-MB231, MCF-7, A431, BxPC-3) cancer cells (each 2.5×10$^4$ cells/well) were plated in a 96-well assay plate and cultured overnight. On the day of assay, the anti-HER2/anti-4-1 BB bispecific antibodies (Example 3; 15 nM, 4-fold or 20 nM, 5-fold or 100 nM, 5-fold dilution) to be tested and effector Jurkat cells (each 2.5×10$^4$ cells/well) were added to the plate. After 6 hours of incubation, Bio-Glo™ Reagent was added and luminescence was measured using a microplate reader.

The obtained results are shown in FIGS. 5a-5i. As shown in FIGS. 5a-5i, anti-HER2/anti-4-1BB bispecific antibodies lead to strong activation of 4-1BB signal only when co-cultured with HER2-expressing cells.

6.3. 4-1BB Activation in Various HER2-Expressing Cells (II)

In this example, for measuring 4-1BB signal activation, GloResponse™ NFκB-luc2/4-1 BB Jurkat cell line (Promega), genetically modified to stably express human 4-1 BB and luciferase downstream of a response element, was used as effector cell. In brief, HER2-expressing target cells (Calu-3 or HCC1954; 2.5×10$^4$ cells/well) were plated in a 96-well assay plate and cultured overnight. On the day of assay, the anti-HER2/anti-4-1 BB bispecific antibodies (Example 3; 20 nM, 5-fold or 133 nM, 6-fold dilution) to be tested and effector Jurkat cells (2.5×10$^4$ cells/well) were added to the plate. After 6 hours incubation, Bio-Glo™ Reagent was added and luminescence was measured using a microplate reader.

The obtained results are shown in FIGS. 6a and 6b. As shown in FIGS. 6a and 6b, all the anti-HER2/anti-4-1 BB bispecific antibodies tested lead to strong activation of 4-1 BB signal only when co-cultured with HER2 high expressing cell.

6.4. HER2 Quantitation

HER2 cell surface expression level was quantified on various cancer cell lines using QIFIKIT quantification kit (Dako) according to manufacturer's recommendation. Briefly, cells were stained with unlabeled anti-HER2 mouse monoclonal antibody(R&D systems) or purified mouse IgG2b isotype control(R&D systems) at saturating concentration. After washing, the stained cells and calibration beads from the kit were simultaneously labeled with the same FITC-conjugated goat anti-mouse IgG secondary antibody from the kit. Labeled cells and calibration beads were analyzed on a flow cytometer. A linear regression was performed using MFI values from the calibration beads. ABC (Antibody-Binding Capacity) was extrapolated from this regression line and sABC (specific ABC) was determined by subtracting ABC of the isotype control antibody from ABC of anti-HER2 antibody.

The obtained results are shown in Table 33.

TABLE 33

| Cell lines | | HER2 sABC |
| --- | --- | --- |
| NCI-N87 | ATCC, CRL-5822 | 1,755,033 |
| Calu-3 | ATCC, HTB-55 | 734,348 |
| HCC1954 | ATCC, CRL-2338 | 497,805 |
| JIMT1 | DSMZ, ACC 589 | 93,113 |
| ZR-75-1 | ATCC, CRL-1500 | 25,360 |
| A431 | ATCC, CRL-1555 | 13,130 |
| MCF-7 | ATCC, HTB-22 | 8,525 |
| MDA-MB231 | ATCC, HTB-26 | 3,841 |
| BxPC-3 | ATCC, CRL-1687 | 2,013 |

As shown in Table 33, the sABC of 9 cancer cell lines was determined.

6.5. Correlation Between the HER2 sABC and 4-1BB-Induced NF-kB Signaling

The HER2 levels measured in Example 6.4 were standardized to HER2 levels expressed by HCC1954. The levels of 4-1BB activation by the bispecific antibody were determined as maximum level of fold change compared with control in 4-1 BB NF-kB luciferase reporter assay of Example 6.2. Shared area indicates confidence interval for a linear fit.

The obtained results are shown in FIG. 7. As shown in FIG. 7, 4-1BB activation by anti-HER2/anti-4-1 BB bispecific antibody showed a strong correlation with HER2 cell surface expression.

Example 7. T Cell Immune Response 7.1. Effect on Release of Cytokine

To test the ability of bispecific antibodies to stimulated human peripheral blood mononuclear cells (PBMCs) response, the concentration of IFN-gamma in supernatant was measured. Human PBMCs were co-cultured with HCC1954 cancer cells expressing HER2 in the presence of anti-human CD3 antibody (BioLegend, 5 ug/mL) and the bispecific antibodies (Example 3; 3 ug/mL, 4-fold dilution) to be tested. After culture in a humidified chamber with 5% $CO_2$ at 37° C. for 72 hours, the concentration of IFN-gamma in supernatant was measured by Human IFN-gamma Quantikine Kit (R&D system, SIF50).

The obtained results are shown in FIGS. 8a-8d. As shown in FIGS. 8a-8d, all the tested bispecific antibodies induced cytokine release more than the combination of each monoclonal antibody in presence of HER2 high expressing cells.

7.2. Effect on Target Cell Growth

To test the ability of bispecific antibodies to stimulated human PBMCs response, target cell lysis assay was used. Human PBMCs were co-cultured with HCC1954 cancer cells expressing HER2 in the presence of anti-human CD3 antibody (BioLegend, 5 ug/mL) and the bispecific antibodies (Example 3; 3 ug/mL, 4-fold dilution) to be tested. After culture in a humidified chamber with 5% $CO_2$ at 37° C. for 72 hours, the survival of HCC1954 was measured by cell counting kit-8 (Dojindo, CK04-20).

The obtained results are shown in FIGS. 9a-9d. As shown in FIGS. 9a-9d, all the tested bispecific antibodies showed superior cancer cell death activities compared to the combination of each monospecific antibody in presence of HER2 high expressing cells.

Example 8. In Vivo Anti-Tumor Efficacy in HCC1954 Bearing hPBMC Engrafted Mice 8.1. Anti-Tumor Activity To test in vivo anti-tumor efficacy of anti-HER2/anti-4-1 BB bispecific antibodies, PBMC-humanized NSG mice were used. 7-week-old NSG mice (The Jackson Laboratory) were intravenously injected with $1 \times 10^7$ human PBMC and HCC1954 cancer cells ($1 \times 10^7$ cells/mouse in PBS:Matrigel=1:1 solution) were inoculated into right flank of the mice. HCC1954 bearing humanized mice were assigned to each test group (n=12/group) at day 2 post tumor implantation. The mice were intravenously administrated with human IgG1 control antibody, anti-4-1 BB antibody or anti-HER2/anti-4-1BB bispecific antibody twice a week at doses of 10 mg/kg or 7.5 mg/kg for 4 weeks. Antibodies were injected twice a week and the tumor size was measured with a digital caliper.

The obtained results are shown in FIG. 10. As shown in FIG. 10, all the tested bispecific antibodies showed superior anti-tumor activity to benchmark anti-4-1 BB antibody (Urelumab, BMS) as well as the control antibody.

8.2. Analysis of Tumor-Infiltrating Lymphocytes (TIL)

To evaluate TIL, formalin-fixed, paraffin-embedded tumor tissue sections from HCC1954 bearing hPBMC engrafted mice were immunostained with anti-hCD45 antibody (human leukocyte marker, Cell Signaling Technology), anti-hCD4 antibody (human helper T-lymphocyte marker, Cell Signaling Technology), anti-hCD8 antibody (human cytotoxic T-lymphocyte marker, Cell Signaling Technology), and anti-hCD16 antibody (human natural killer cell marker, Cell Signaling Technology). The immunohistochemical technique was performed by applying the avidin-biotin detection kit (Vector Laboratories), to measure each marker positive cells. Briefly, Formalin-fixed paraffin-embedded tumoral tissue sections were deparaffinized and rehydrated. Antigen retrieval from rehydrated tissue sections were performed by placing sections in EDTA buffer (pH 9.0). After washing with phosphate-buffered saline (PBS) and incubation with blocking solution for 30 min, sections were incubated with primary antibodies at 4° C. overnight. Vectastain Elite ABC kit (Vector Lab) and the protocol provided by the manufacturer were used for the immunostaining. Sections were then counterstained with hematoxylin, dehydrated using graded alcohols and xylene, and mounted with Permount.

The obtained result is shown in FIG. 11. As shown in FIG. 11, Her2×41-BB bispecific antibodies effectively enhanced infiltration of immune cells including $CD45^+$ cells, $CD4^+$ T cells, CD8⁺ T cells, and NK cells into tumor tissues, compared to BMUR (Urelumab).

Example 9. In Vivo Anti-Tumor Efficacy in 4-1BB Knock-in Mice 9.1. The Anti-Tumor Activity In vivo anti-tumor efficacy of anti-HER2/anti-4-1 BB bispecific antibodies was evaluated in human HER2/MC38 tumor (Biocytogen) bearing 4-1 BB knock-in mice (Biocytogen). Tumor bearing humanized mice were randomized to each test group (n=5/group) at day 4 post tumor implantation based on tumor volume (approximately 80 mm³). Human IgG1 antibody, Trastuzumab (anti-HER2 antibody), and anti-HER2/anti-4-1 BB bispecific antibodies (HER2(WT)× 1A10 M12, HER2(NA)×1A10 M12) were respectively intra peritoneally administered twice a week at dose of 10 mg/kg or 7.5 mg/kg into the mice for 4 weeks. Tumor size was measured with a digital caliper.

The obtained results are shown in FIG. 12. As shown in FIG. 12, anti-HER2/anti-4-1 BB bispecific antibodies showed superior anti-tumor efficacy compared to Trastuzumab in human HER2/MC38 tumor. Especially, the tumors of all mice that were treated with HER2(WT)×1A10 M12 have been cured.

9.2. Evaluation on the Effect of Tumor Specific Memory T Cell

The mice cured by HER2(WT)×1A10 M12 were re-challenged with human HER2/MC38 tumor cells (Biocytogen) and B16 F10 tumor cells (ATCC) in both flanks at 63 days post tumor injection. Mice were not administered with any drug during re-challenge study period. Tumor size was measured with a digital caliper.

The obtained results are shown in FIG. 13. As shown in FIG. 13, human HER2/MC38 tumor development was not observed, whereas B16 F10 tumor was grown in mice cured by HER2(WT)×1A10 M12 treatment.

Example 10. Antibody-Dependent Cellular Cytotoxicity (ADCC) Activity (NA Backbone Vs. WT)

10.1. NK Cell-Mediated ADCC

In this example, human peripheral blood-derived CD56⁺ NK cells were used as effector cells and CellTrace Violet (Thermo Fisher Scientific)-labeled HCC1954 cells expressing HER2 were used as target cells. Cells were co-cultured at an effector:target ratio of 5:1 with 50 nM of anti-HER2/anti-4-1BB bispecific antibodies (Example 3) at 37° C. After 4 hours, cells were stained with Fixable Viability Dye (eBioscience™) and then the ratio of dead target cells was analyzed by flow cytometry.

The obtained results are shown in following FIG. 14. As shown in FIG. 14, IgG1 type (WT) of anti-HER2/anti-4-1 BB bispecific antibodies showed a prominent ADCC effect mediated by NK cells.

10.2. 4-1BB Signal Activation Dependent on FcγRIIb Engagement

In this example, CHO-K1 cells expressing FcγRIIb (Promega) were plated in a 96-well assay plate and cultured overnight. On the day of assay, Jurkat/4-1BB cells (Promega) were plated in 96 well plate. Cells were incubated with a titration of anti-HER2/anti-4-1 BB bispecific antibodies in the presence (FcγRIIb dependent) or absence (FcγRIIb independent) of CHO-K1 cells expressing FcγRIIb (Promega). After 6 hours of induction, Bio-Glo™ Luciferase Assay reagent was added and luminescence was determined using a SpectraMax L luminometer (Molecular Devices). Four-parameter logistic curve analysis was performed with GraphPad Prism® software.

The obtained results are shown in following Tables 34 (FcγRIIb-dependent 4-1BB bioassay) and 35 (FcγRIIb-independent 4-1BB bioassay), and FIGS. 15a (FcγRIIb-dependent 4-1 BB bioassay) and 15b (FcγRIIb-independent 4-1 BB bioassay).

TABLE 34

| FcγRIIb-dependent 4-1BB bioassay | | |
|---|---|---|
| | Fold of induction (RLU) | $EC_{50}$ (nM) |
| Urelumab | 195.5 | 0.2364 |
| HER2(WT)X1A10 M12 | <2 | Not applicable |
| HER2(NA)X1A10 M12 | <2 | Not applicable |
| HER2(WT)X1A12 M1 | <2 | Not applicable |
| HER2(NA)X1A12 M1 | <2 | Not applicable |

TABLE 35

| FcγRIIb-independent 4-1BB bioassay | | |
|---|---|---|
| | Fold of induction (RLU) | $EC_{50}$ (nM) |
| Urelumab | 15.57 | 0.5196 |
| HER2(WT)X1A10 M12 | <2 | Not applicable |
| HER2(NA)X1A10 M12 | <2 | Not applicable |
| HER2(WT)X1A12 M1 | <2 | Not applicable |
| HER2(NA)X1A12 M1 | <2 | Not applicable |

As shown in Tables 34 and 35, and FIGS. 15a and 15b, Urelumab-treated group showed 13.5-fold difference in top RLU and 2.2-fold difference in $EC_{50}$ according to the presence of FcγRIIb CHO-K1 cells. Four anti-HER2/anti-4-1BB bispecific antibodies showed very low RLU compared to Urelumab regardless of the presence or absence of FcγRIIb CHO-K1 cells. These data showed that all the tested anti-HER2/anti-4-1 BB bispecific antibodies have potential benefits compared to urelumab, which has severe toxicity in clinical studies (NCT00309023, NCT00612664, NCT014712210).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and "one or more" and similar referents in the context of describing the invention (especially in the context of the following claims) are to be construed to cover both the singular and the plural, unless otherwise indicated herein or clearly contradicted by context. The use of the term "at least one" (or "one or more") followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "comprising, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An anti-4-1 BB/anti-HER2 bispecific antibody comprising:
    (a) an anti-4-1 BB antibody or an antigen-binding fragment thereof, wherein the anti-4-1 BB antibody or the antigen-binding fragment thereof is an anti-4-1 BB scFv of the anti-4-1 BB antibody, and
    (b) an anti-HER2 antibody or an antigen-binding fragment thereof, wherein the anti-HER2 antibody or an antigen-binding fragment thereof is a full-length form of the anti-HER2 antibody, and the anti-4-1 BB scFv is linked at its N-terminus to the C-terminus of a heavy chain of the anti-HER2 antibody,
        wherein the anti-4-1 BB antibody or the antigen-binding fragment thereof comprises:
    (1) a heavy chain variable region comprising the amino acid sequence of SEQ ID NO: 18 and a light chain variable region comprising the amino acid sequence of SEQ ID NO: 30, or
    a heavy chain variable region comprising the amino acid sequence of SEQ ID NO: 24 and a light chain variable region comprising the amino acid sequence of SEQ ID NO: 33;
    (2) a heavy chain variable region comprising the amino acid sequence of SEQ ID NO: 19 and a light chain variable region comprising the amino acid sequence of SEQ ID NO: 30 or 31, or
    a heavy chain variable region comprising the amino acid sequence of SEQ ID NO: 25 and a light chain variable region comprising the amino acid sequence of SEQ ID NO: 33 or 34;
    (3) a heavy chain variable region comprising the amino acid sequence of SEQ ID NO: 20 and a light chain variable region comprising the amino acid sequence of SEQ ID NO: 30 or 31; or
    (4) a heavy chain variable region comprising the amino acid sequence of SEQ ID NO: 21 and a light chain variable region comprising the amino acid sequence of SEQ ID NO: 30,
    a heavy chain variable region comprising the amino acid sequence of SEQ ID NO: 22 and a light chain variable region comprising the amino acid sequence of SEQ ID NO: 31,
    a heavy chain variable region comprising the amino acid sequence of SEQ ID NO: 27 and a light chain variable region comprising the amino acid sequence of SEQ ID NO: 33, or
    a heavy chain variable region comprising the amino acid sequence of SEQ ID NO: 28 and a light chain variable region comprising the amino acid sequence of SEQ ID NO: 34, and
    wherein the anti-HER2 antibody or an antigen-binding fragment thereof comprises:
    a heavy chain comprising the amino acid sequence of SEQ ID NO: 73; and
    a light chain comprising the amino acid sequence of SEQ ID NO: 75.

2. The anti-4-1BB/anti-HER2 bispecific antibody of claim 1, wherein the anti-4-1BB scFv further comprises a peptide linker between the heavy chain variable region and the light chain variable region.

3. The anti-4-1BB/anti-HER2 bispecific antibody of claim 1, wherein the anti-HER2 antibody is Trastuzumab, or Trastuzumab emtansine (T-DM1).

4. A pharmaceutical composition comprising the anti-4-1BB/anti-HER2 bispecific antibody of claim 1 and a pharmaceutically acceptable carrier.

5. The anti-4-1BB/anti-HER2 bispecific antibody of claim 1, wherein the anti-4-1BB/anti-HER2 bispecific antibody comprises:
    a polypeptide comprising the amino acid sequence of SEQ ID NO: 83, or 84; and
    a polypeptide comprising the amino acid sequence of SEQ ID NO: 75.

6. The anti-4-1BB/anti-HER2 bispecific antibody of claim 1, wherein the anti-4-1BB/anti-HER2 bispecific antibody comprises:
    a polypeptide comprising the amino acid sequence of SEQ ID NO: 83; and
    a polypeptide comprising the amino acid sequence of SEQ ID NO: 75.

* * * * *